(12) United States Patent
Kumagai et al.

(10) Patent No.: US 8,080,531 B2
(45) Date of Patent: Dec. 20, 2011

(54) METHODS FOR MODULATING CHECKPOINT ACTIVATION THROUGH TOPBP1

(75) Inventors: Akiko Kumagai, Altadena, CA (US); William Dunphy, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 427 days.

(21) Appl. No.: 12/220,982

(22) Filed: Jul. 30, 2008

(65) Prior Publication Data
US 2009/0098111 A1 Apr. 16, 2009

Related U.S. Application Data

(63) Continuation of application No. 11/715,597, filed on Mar. 8, 2007, now abandoned.

(60) Provisional application No. 60/808,092, filed on May 24, 2006.

(51) Int. Cl.
*C12N 15/11* (2006.01)
*C07H 21/02* (2006.01)
*C07H 21/04* (2006.01)

(52) U.S. Cl. ..... 514/44; 536/23.1; 536/24.3; 536/24.33; 536/24.5

(58) Field of Classification Search ............ 930/10, 930/240
See application file for complete search history.

(56) References Cited

OTHER PUBLICATIONS

GenBank Accession No. BAA34202 (published Nov. 6, 1998).*
Yamane et al. Eur. J. Biochem. 250 (3) 794-799 (1997).*
Yamane et al. Cancer Research, 2003 vol. 63:3049-3053.*
Yamane et al. Molecular and cellular Biology, 2002 vol. 22:555-566.*
Lu et al. (2005) in RNA Interference Technology (Cambridge, Appasani, ed.).*
Downward, J. BMJ, 2004 vol. 328:1245-1248.*
Braasch et al. Biochemistry, vol. 41, pp. 4503-4510.*
Yoo, et al., "Ataxia-telangiectasie Mutated (ATM)-dependent Activation of ATR Occurs through Phosphorylatin of TopBP1 by ATM," Journal of Biological Chemisry 282(24):17501-17506 (2007).
Ball, et al., "Function of a Converved Checkpoint Recruitment Domain in ATRIP Proteins," Molecular and Celluar Biology 27(9): 3367-3377 (2007).
Kumagia, et al., "TopBP1 Activates the ATR-ATRIP Complex," Cell 124:943-955 (2006).
Corez, et al., "ATR and ATRIP: Partners in Checkpoint Signaling," Science 294:1713-1716 (2001).
Kim, et al, "Human TipBP1 Ensures Genome Integrity During Nornal S Phase," Molecular and Cellular Biology, 25(24):10907-10915, (2005).
Braasch, et al., "Novel Antisense and Peptide Nucleic Acid Strategies for Controlling Gene Expression," Biochemistry, vol. 41 No. 14, pp. 4503-4509, (2002).
Downward, J. "Science, medicine, and the future RNA Interference," BMJ vol. 328, pp. 1245-1248; May 22, 2004.
Lu, et al., "Delivering siRNA in vivo for functional genomics and novel therapeutics," RNA Interference Technology (Cambridge, Appasani, ed.), pp. 303-317, (2005).

(Continued)

*Primary Examiner* — Terra Cotta Gibbs
(74) *Attorney, Agent, or Firm* — Ropes & Gray LLP

(57) ABSTRACT

ATR kinase is a key regulator of checkpoint responses to incompletely replicated and damaged DNA. Without this checkpoint, cells will enter mitosis prematurely, likely resulting in cell death. The invention provides methods and reagents to either block or activate the activation of the ATR kinase checkpoint, through, for example, either blocking or activating the expression of an ATR activator TopBP1. The invention also provides screening methods to identify additional ToBP1 inhibitors or activators that may be used to modulate the activity of the ATR checkpoint.

10 Claims, 10 Drawing Sheets

OTHER PUBLICATIONS

Yamane, et al., "A DNA Damage-Regulated BRCT-Containing protein, TopBP1, Is Required for Cell Survival," Molecular and Cellular Biology, vol. 22, No. 2, pp. 555-566, Jan. 2002.

Yamane, et al., "Both DNA Topoisomerase II-binding Protein 1 and BRCA1 Regulate the $G_2$-M Cell Cycle Checkpoint," Cancer Research, vol. 63, 3049-3053, Jun. 15, 2003.

* cited by examiner

Figure 8
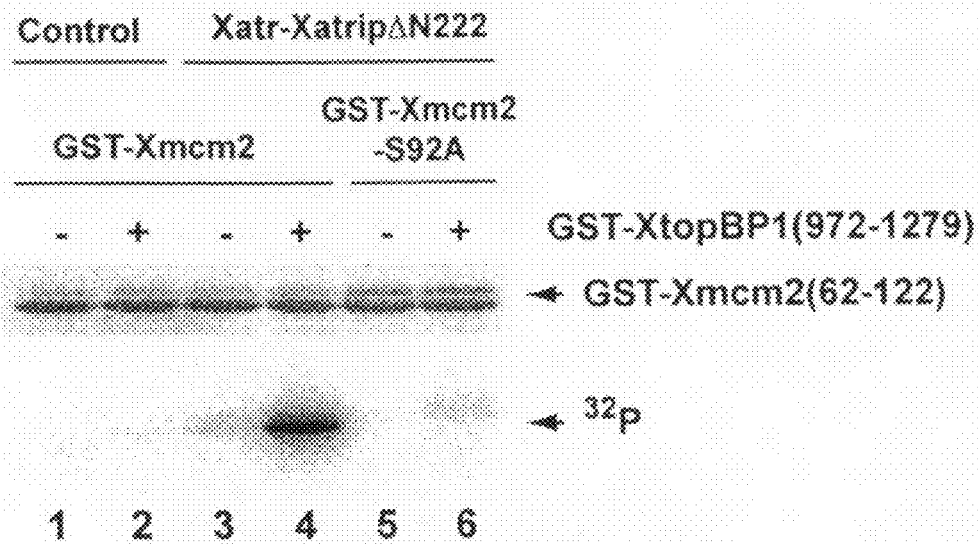
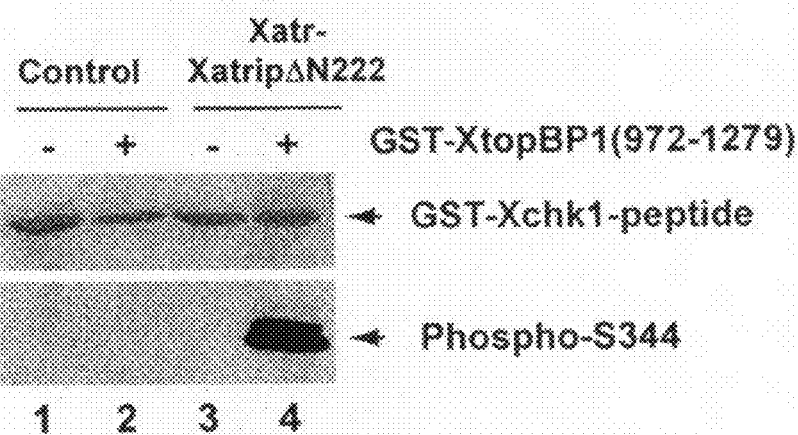
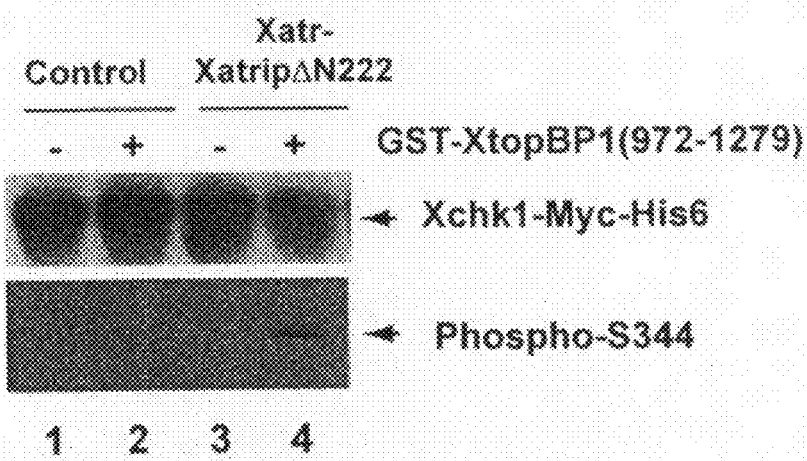

METHODS FOR MODULATING CHECKPOINT ACTIVATION THROUGH TOPBP1

REFERENCE TO RELATED APPLICATION

This application is a continuation application of U.S. Ser. No. 11/715,597, filed on Mar. 8, 2007, now abandoned, which claims the benefit of the filing date under 35 U.S.C. §119(e) of U.S. Provisional Application No. 60/808,092, filed on May 24, 2006, the entire contents of the above-referenced applications are incorporated herein by reference.

GOVERNMENT SUPPORT

Work described herein was funded, in whole or in part, by National Institute of Health Grant Nos. GM043974 and GM070891. The U.S. government has certain rights in the invention.

BACKGROUND OF THE INVENTION

Control of the cell cycle is fundamental to the growth and maintenance of eukaryotic organisms, from yeasts to mammals. Cells have evolved critical mechanisms to help protect the fidelity of DNA synthesis. One important mechanism is commonly referred to as "cell-cycle checkpoint control." Cell cycle checkpoints insure that individual steps of the cell cycle are completed before the next step occurs. In response to DNA damage or a block to DNA replication, progression through the cell cycle is delayed. This allows time for the cell to repair the DNA prior to continuing through the cell cycle, thus improving genomic stability and the fidelity of DNA synthesis (Elledge, *Science* 274: 1664-1672, 1996; O'Connell et al., *Trends Cell Biol* 10: 296-303, 2000).

The ability to coordinate cell cycle transitions in response to genotoxic and other stressors is critical to the maintenance of genetic stability and the prevention of uncontrolled cellular growth. Loss of a checkpoint gene or its proper control leads to genetic instability and the inability of cells to deal with genomic insults such as those suffered as a result of the daily exposure to ultraviolet radiation. The loss of negative growth control and improper monitoring of the fidelity of DNA replication are common features of tumor cells. Compromise of the checkpoints, e.g., by mutation or other means, either in the checkpoint genes themselves, or their upstream modulators and/or downstream effectors, frequently leads to such detrimental results as cell death, infidelity in chromosome transmission, and/or increased susceptibility to deleterious environmental factors (e.g., DNA-damaging agents).

Many components of the checkpoint pathways that respond to DNA damage have been identified in various species from yeast to vertebrates (Elledge, *Science* 274: 1664-1672, 1996). The response is believed to involve sensor proteins which respond to DNA damage/replication stress. The sensor proteins transmit a signal (via transducer proteins), which induces one or more effects in a cell. Such effects allow the cell to appropriately cope with the DNA damage by, for example, inducing a cell cycle delay to allow time for the DNA damage to be repaired. Other possible responses of a cell to DNA damage include cell death, for example, if the DNA damage is too great to be repaired (recently reviewed in Zhou and Elledge, *Nature* 408: 433-439, 2000).

One class of sensor proteins include Rad3/ATR proteins (Bentley et al., *EMBO Journal* 15: 6641-6651, 1996; O'Connell et al., *Trends Cell Biol* 10: 296-303, 2000; Cimprich et al., *PNAS* 93: 2850-2855, 1996; Keegan et al., *Genes & Development* 10: 2423-2437, 1996). This family of sensor proteins actually is part of a larger family of phosphoinositide kinase (PIK)-related protein kinases. This family of PIK-kinases (PIKK) are characterized by a C-terminal kinase domain, and include ATM/Tell (Lavin and Shiloh, *Annu. Rev Immunology* 15: 177-202, 1997; Sanchez et al., *Science* 271: 357-360, 1996) and DNA-PKcs (Smith and Jackson, *Genes & Dev.* 13: 916-34, 1999).

Following detection of DNA damage or a replication block, a signal is transduced to effector proteins. These include Chk1 and Cds1 (Elledge, *Science* 274: 1664-1672, 1996). However, the molecular nature of how this signal is transduced is not well understood. Based on previous work, it appears that various sensors induce cell cycle delay in response to different types of DNA damage, and that different sensors signal through effector proteins to cause downstream biological effects. Also, it appears that the general machinery for checkpoint control in response to DNA damage is evolutionarily conserved.

Given the importance of proper checkpoint control in maintaining genomic stability and insuring the fidelity of DNA replication, a better understanding of the molecular mechanisms underlying this process, such as how ATR is activated by its upstream regulators, has tremendous value. Specifically, such an understanding allows for the development of rational screens for agents which can modulate checkpoint control in response to DNA damage. Such agents provide novel therapies for various proliferative disorders including all forms of cancer.

Thus, there remains a need to identify upstream modulators of the checkpoint control genes, such as modulators of ATR, to develop methods of screening for agents which modulate the activation of ATR, and to use such agents as therapeutic agents for treating various disorders, such as proliferative disorders.

SUMMARY OF THE INVENTION

The present invention describes the specific activation of ATR (but not the related ATM) by the ATR activator TopBP1 and its related proteins.

One aspect of the invention provides a method for modulating ATR activation by TopBP1, comprising administering one or more modulator of TopBP1 activity.

In certain embodiments, the modulator affects the transcription and/or expression of TopBP1.

In certain embodiments, the modulator affects the binding of TopBP1 to the ATR-ATRIP complex.

In certain embodiments, the modulator affects the activation of the ATR kinase activity by TopBP1.

In certain embodiments, the modulator is an inhibitor of TopBP1 activity. For example, the inhibitor may be one or more of: an siRNA, a microRNA, a shRNA, an antisense oligonucleotide, a ribozyme, a DNA enzyme, a Morpholino antisense, a small molecule inhibitor, an antibody or functional fragment thereof, a peptide, a dominant negative mutant TopBP1 or fragment thereof, or a peptidomimetic.

In certain embodiments, the modulator is an activator of TopBP1 activity. For example, the activator may be one or more of: a TopBP1 activator (e.g., oligonucleotide duplex AT70), a TopBP1 transcriptional activator, a TopBP1 stabilizer, or an ATR activation domain of TopBP1.

In certain embodiments, the method further comprises contacting ATR with one or more modulators of ATR activity.

In certain embodiments, ATR and TopBP1 are inside a cell.

In certain embodiments, the cell is a vertebrate cell.

In certain embodiments, ATR is at least about 90% identical to human or *Xenopus* ATR.

In certain embodiments, TopBP1 is at least about 90% identical to human or *Xenopus* TopBP1.

Another aspect of the invention provides a method to screen for a modulator of ATR activation by TopBP1, the method comprising: (1) providing a mixture comprising TopBP1 and ATR; (2) contacting the mixture with a candidate compound; (3) determining the binding of TopBP1 to ATR, and/or the activation of the kinase activity of ATR; wherein a statistically significant change either in the binding of TopBP1 to ATR or the activation of the kinase activity of ATR or both in the presence of the test compound compared to those in the absence of the test compound is indicative that the test compound is a modulator of TopBP1 activation of ATR.

In certain embodiments, the method further comprises determining the extent of ATR activity change by the test compound in the absence of TopBP1 in the mixture.

In certain embodiments, the modulator is an inhibitor.

In certain embodiments, the modulator is an activator.

In certain embodiments, TopBP1 and ATR form a complex in the mixture.

In certain embodiments, the complex further comprises ATRIP.

In certain embodiments, the kinase activity of ATR is determined by the degree of phosphorylation of one or more substrates by ATR.

In certain embodiments, the degree of phosphorylation is measured by immunoassay and/or Western blot.

In certain embodiments, the one or more substrates include Chk1, MCM2, Rad1, Hus1, Rad17, Nbs1, Smc1, H2AX, PHAS-I, and/or a functional fragment thereof.

In certain embodiments, TopBP1 is a full length protein, or a functional fragment comprising amino acid sequences between the sixth and seventh BRCT domains of TopBP1.

In certain embodiments, ATR is a full length protein, or a fragment comprising a functional kinase domain.

In certain embodiments, TopBP1 or ATR is from human or *Xenopus*.

In certain embodiments, the method is an in vivo assay.

Another aspect of the invention provides a method for treating cancer, comprising administering to a patient in need thereof an effective amount of a therapeutic composition comprising an inhibitor of ATR activation by TopBP1.

In certain embodiments, the inhibitor is an inhibitor of TopBP1 activity.

In certain embodiments, the method further comprises administering an inhibitor of ATR activity.

In certain embodiments, the method further comprises administering a treatment and/or an agent that damages DNA and/or inhibits DNA replication.

In certain embodiments, the treatment is ionizing radiation.

In certain embodiments, the agent is a chemotherapeutic agent.

Another aspect of the invention provides an ATR activator comprising a polypeptide at least about 90% identical to the ATR activation domain of TopBP1, said ATR activator activates the kinase activity of ATR.

In certain embodiments, the ATR activation domain of TopBP1 comprises residues 1050-1192 of human TopBP1.

It is contemplated that all embodiments of the invention, including embodiments described under different aspects of the invention, may be combined with any other embodiments of the invention as appropriate.

BRIEF DESCRIPTION OF THE DRAWINGS

FIG. 1A shows isolation of Xatr-Xatrip complexes. Control buffer (lane 1), His6-XatripΔN222-FLAG (lane 2), and full-length His6-Xatrip-FLAG (lane 3) were added to egg extracts containing anti-FLAG antibody beads. After incubation, the beads were reisolated, washed, and eluted with 3×-FLAG peptide. The eluates were immunoblotted with anti-Xatr (top) and anti-FLAG antibodies (bottom). FIG. 1B shows preparation of His6-XtopBP1. The protein was purified from Sf9 cells and stained with Coomassie blue. FIG. 1C shows the kinase activity of isolated Xatr-Xatrip is greatly increased in the presence of His6-XtopBP1. Control eluate (lanes 1 and 2) and eluates containing either Xatr-XatripΔN222 (lanes 3 and 4) or Xatr-Xatrip complexes (lanes 5 and 6) from FIG. 1A were incubated in kinase buffer with $^{32}$P-ATP and PHAS-I in the absence (lanes 1, 3, and 5) or presence of His6-XtopBP1 (lanes 2, 4, and 6). Reactions were subjected to SDS-PAGE. The gel was stained with Coomassie blue (top), and $^{32}$P incorporation into PHAS-I was detected by phosphorimaging (bottom). FIG. 1D shows that His6-XtopBP1 induces the kinase activity of Xatr in a dose-dependent manner. Xatr-XatripΔN222 (lanes 1-7) and control eluate (lane 8) were incubated either without XtopBP1 (lane 1) or with different amounts of XtopBP1 (0.5-30 µg/ml) (lanes 2-8) in the presence of $^{32}$P-ATP and PHAS-I. Reactions were processed for staining with Coomassie blue (top) and phosphorimaging (bottom). FIG. 1E shows quantitation of $^{32}$P-incorporation into PHAS-I from FIG. 1D.

In FIG. 2A, egg extracts were left untreated (lanes 1-4) or subjected to an immunodepletion procedure with either control (lane 5) or anti-Xatr antibodies (lane 6). Extracts were incubated with anti-FLAG beads in the absence (lanes 1 and 2) or presence of XatripΔN222-FLAG (lanes 3-6). The beads were reisolated and eluted with 3×-FLAG peptide. Eluates were incubated with $^{32}$P-ATP and PHAS-I in the absence (lanes 1 and 3) or presence of His6-XtopBP1 (lanes 2 and 4-6). After SDS-PAGE, the top portion of the gel was immunoblotted with anti-Xatr and anti-FLAG antibodies (top two panels). The bottom portion was stained with Coomassie blue (second panel from bottom) and analyzed with phosphorimager (bottom panel). FIG. 2B shows quantitation of the data in FIG. 2A. Data are represented as mean±standard deviation. FIG. 2C shows that the kinase activity of the activated form of Xatr is sensitive to caffeine. Xatr-XatripΔN222 was activated by His6-XtopBP1 and assayed for kinase activity toward PHAS-I in the absence (lane 1) or presence of 0.04, 0.2, 1, and 5 mM caffeine (lanes 2-5) as in FIG. 2A. FIG. 2D is a plot of the data in FIG. 2C. Data are represented as mean±standard deviation.

FIG. 3A shows domains of XtopBP1. Roman numerals indicate BRCT domains, as designated in the literature. Fragments containing the indicated amino acids of XtopBP1 (1-348, 333-646, 623-984, 972-1279, and 1197-1513) were produced as GST fusion proteins in bacteria. The Δ993-1196 mutant was produced as a His6 fusion in Sf9 cells. In FIG. 3B, Xatr-XatripΔN222 complex (lanes 1-6) and control eluate (lane 7) were incubated in the absence (lane 1) or presence (lanes 2-6) of GST fusion proteins containing the indicated segments of XtopBP1 at a final concentration of 40 µg/ml in kinase buffer containing $^{32}$P-ATP and PHAS-I. Reactions were subjected to SDS-PAGE. GST fusion proteins and PHAS-I were stained with Coomassie blue (top and middle panels). Incorporation of $^{32}$P into PHAS-I was detected by phosphorimaging (bottom panel). FIG. 3C shows that the ATR-activating function is conserved in human TopBP1. The Xatr-XatripΔN222 complex (lanes 1-3) was incubated with buffer alone (lane 1), XtopBP1 (972-1279) (lane 2), or human GST-TopBP1 (978-1192) (lane 3) and assayed for kinase activity toward PHAS-I. FIG. 3D shows preparations of His6-XtopBP1 and His6-XtopBP1Δ993-1196 from Sf9 cells (stained with Coomassie blue). In FIG. 3E, control eluate (lanes 1-3) and Xatr-XatripΔN222 complex (lanes 4-6) were incubated with buffer alone (lanes 1 and 4), full-length His6-XtopBP1 (lanes 2 and 5), or His6-XtopBP1Δ993-1196 (lanes 3 and 6) and assayed for kinase activity toward PHAS-I. FIG. 3F shows that XtopBP1 activates Xatr but not Xatm. Egg extracts were immunoprecipitated with control (lanes 1 and 2), anti-Xatr antibodies (lanes 3 and 4), or anti-Xatm antibodies (lanes 5 and 6). The immunoprecipitates were incubated in the absence (lanes 1, 3, and 5) or presence of GST-XtopBP1 (972-1279) (lanes 2, 4, and 6) in kinase buffer containing 32P-ATP and PHAS-I. The samples were subjected SDS-PAGE and immunoblotted with anti-Xatm (top) and anti-Xatr antibodies (middle). Kinase activity was determined by $^{32}P$ incorporation into PHAS-I (bottom).

FIG. 4A shows that GST-XtopBP1 (972-1279) associates with Xatr-Xatrip. Egg extracts (lane 1) were incubated with no recombinant protein (lane 2), GST-XtopBP1 (972-1279) (lane 3), or GST-XtopBP1 (1197-1513) (lane 4). The extracts were filtered through a G25 Sephadex column to remove endogenous glutathione and incubated with glutathione agarose beads. The beads were isolated and immunoblotted for Xatr (top) and Xatrip (bottom). In FIG. 4B, egg extracts (lane 1) were immunodepleted with control (lane 2) or anti-Xatrip antibodies (lanes 3 and 4). For lane 4, recombinant XatripΔN222-FLAG was added back later. Extracts were immunoblotted with anti-Xatr (top) and anti-Xatrip antibodies (bottom). In FIG. 4C, control buffer (lane 1) and GST-XtopBP1 (972-1279) (lanes 2-4) were incubated with the indicated extracts from FIG. 4B. Binding of Xatr to glutathione beads was determined by immunoblotting as in FIG. 4A. In FIG. 4D, Xatr was immunoprecipitated from mock-depleted (lanes 1 and 2) and Xatrip-depleted extracts (lanes 3 and 4). Twice as much Xatrip-depleted extract was immunoprecipitated due to its reduced content of Xatr. The immunoprecipitates were incubated with control buffer (lanes 1 and 3) or GST-XtopBP1 (972-1279) (lanes 2 and 4) and assayed for kinase activity toward PHAS-I (bottom). Samples were also immunoblotted for Xatr (top) and Xatrip (middle).

FIG. 5A shows alignment of residues 993-1196 from the ATR-activating domain of XtopBP1 (SEQ ID NO: 12) with corresponding segments of human (SEQ ID NO:13), chicken (SEQ ID NO:14), and zebrafish (SEQ ID NO: 15) TopBP1. Two conserved sequences (RQLQ (SEQ ID NO: 1) and WDDP (SEQ ID NO: 2)) are marked with lines, and a conserved tryptophan (W1138 in XtopBP1) is denoted with an asterisk. In FIG. 5B, Xatr-XatripAN222 was incubated with GST-XtopBP1(1197-1513) (lane 1) or wild-type (lane 2), W1138R (lane 3), AWDDP (lane 4), and ARQLQ (lane 5) versions of GST-XtopBP1(972-1279) in the presence of PHAS-I and 32P-ATP. Reactions were stained with Coomassie blue to detect GST fusions (top) and PHAS-I (middle), and were analyzed with a phosphorimager (bottom). FIG. 5C shows isolation of recombinant human ATR proteins. Protein G-magnetic beads containing no antibody (lane 1) or anti-FLAG antibodies (lanes 2 and 3) were incubated in nuclear extracts of the GW33 and GK41 U2OS cell lines that were induced to express either wild-type (WT) (lanes 1 and 2) or kinase-deficient (KD) FLAG-ATR (lane 3), respectively. The beads were reisolated and eluted with 3x-FLAG peptide. The whole preparations (beads plus eluates) were immunoblotted with anti-FLAG antibodies. FIG. 5D shows activation of recombinant human ATR. Mock preparations (lanes 1-3) and preparations containing either WT (lanes 4-6) or KD FLAG-ATR (lanes 7-9) from C were incubated with control buffer (lanes 1, 4, and 7), GST-XtopBP1(972-1279) (lanes 2, 5, and 8), or GST-XtopBP1 (972-1279)-W1138R (lanes 3, 6, and 9) in the presence of GST-Xmcm2(62-122). Samples were subjected to SDS-PAGE and processed for staining with Coomassie blue (top) and immunoblotting with anti-phospho-S92 of Xmcm2 antibodies (bottom). FIG. 5C shows isolation of recombinant human ATR proteins. Protein G-magnetic beads containing no antibody (lane 1) or anti-FLAG antibodies (lanes 2 and 3) were incubated in nuclear extracts of the GW33 and GK41 U2OS cell lines that were induced to express either wild-type (WT) (lanes 1 and 2) or kinase-deficient (KD) FLAG-ATR (lane 3), respectively. The beads were reisolated and eluted with 3x-FLAG peptide. The whole preparations (beads plus eluates) were immunoblotted with anti-FLAG antibodies. FIG. 5D shows activation of recombinant human ATR. Mock preparations (lanes 1-3) and preparations containing either WT (lanes 4-6) or KD FLAG-ATR (lanes 7-9) from C were incubated with control buffer (lanes 1, 4, and 7), GST-XtopBP1 (972-1279) (lanes 2, 5, and 8), or GST-XtopBP1 (972-1279)-W1138R (lanes 3, 6, and 9) in the presence of GST-Xmcm2 (62-122). Samples were subjected to SDS-PAGE and processed for staining with Coomassie blue (top) and immunoblotting with anti-phospho-S92 of Xmcm2 antibodies (bottom).

In FIG. 6A, control buffer (lane 1), GST-XtopBP1 (972-1279) at a final concentration of either 50 μg/ml (lane 2) or 100 μg/ml (lane 3), and 100 μg/ml GST-XtopBP1 (1197-1513) (lane 4) were added to interphase egg extracts. Extracts were incubated for 90 min in the presence of 35S-Xchk1 and 3 μM tautomycin. Reactions were subjected to SDS-PAGE and phosphorimaging. In FIG. 6B, Phosphorylation of $^{35}S$-Xchk1 was determined in egg extracts that were incubated with control buffer (lane 1), GST-XtopBP1 (972-1279) (lane 2), or the indicated mutants of the 972-1279 fragment as described in A. All GST fusion proteins were added at a final concentration of 100 μg/ml. In FIG. 6C, human 293T cells were transfected with plasmids encoding EGFP (lane 1), wild-type EGFP-NLS-TopBP1 (978-1286) (lane 2), and EGFP-NLS-TopBP1 (978-1286)-W1145R (lane 3). In addition, untransfected cells were incubated in the absence (lane 4) or presence of 2 mM hydroxyurea for 18 hr (lane 5). Lysates from the cells were immunoblotted with antibodies against phospho-S108 of human Mcm2 (top) or the Mcm2 protein (bottom). In FIG. 6D, 293T cells were transfected with the indicated plasmids. Cells were processed for indirect immunofluorescence with anti-phospho-S108 antibodies and Alexa 568 conjugated goat anti-rabbit antibodies. In addition, cells were examined for fluorescence of EGFP and stained for DNA with Hoechst 33258. FIG. 6E shows quantitation (with the ImageJ program) of the immunofluorescent signal of phospho-S108 from the cells in D as well as from cells transfected with EGFP alone. Signals were compared between expressing and non-expressing cells. Data are represented as mean±standard deviation.

In FIG. 7A, preparations of wild-type (lane 1) and W1138R mutant (lane 2) versions of full-length His6-XtopBP1 were stained with Coomassie blue. In FIG. 7B, kinase reactions with control buffer (lane 1), wild-type His6-XtopBP1 (lanes 2 and 4), and His6-XtopBP1-W1138R (lanes 3 and 5) were conducted with PHAS-I and $^{32}$P-ATP in the presence (lanes 1-3) or absence (lanes 4 and 5) of the Xatr-XatripΔN222 complex. Samples were stained with Coomassie blue (top) or analyzed with a phosphorimager (bottom). FIG. 7C shows immunodepletion of XtopBP1. Egg extracts were left untreated (lane 1) or immunodepleted with control (lane 2) or anti-XtopBP1 antibodies (lanes 3-5). In some cases, either wild-type (lane 4) or W1138R His6-XtopBP1 (lane 5) was added back to the extracts. Extracts were immunoblotted for XtopBP1. In FIG. 7D, untreated (lanes 1 and 2), mock-depleted (lane 3), and XtopBP1-depleted extracts containing control buffer (lane 4), wild-type His6-XtopBP1 (lane 5), or W1138R His6-XtopBP1 (lane 6) were incubated with $^{35}$S-Xchk1 in the absence (lane 1) or presence of aphidicolin (lanes 2-6). Nuclear fractions were subjected to SDS-PAGE and immunoblotted with anti-phospho-S344 of Xchk1 antibodies (top). Samples were also analyzed by phosphorimaging (bottom). In FIG. 7E, DNA replication was measured in a 2 hr incubation by incorporation of $^{32}$P into chromosomal DNA in XtopBP1-depleted extracts to which either wt (lane 1) or W1138R His6-XtopBP1 (lane 2) had been added back.

FIGS. 8A-8C show that XtopBP1 stimulates the activity of Xatr toward a variety of different substrates. In FIG. 8A, control eluate (lanes 1 and 2) and Xatr-XatripΔN222 complex (lanes 3-6) were incubated in the absence (lanes 1, 3, and 5) or presence of GST-XtopBP1 (972-1279) (lanes 2, 4, and 6) in kinase buffer containing $^{32}$P-ATP and either GST-Xmcm2 (62-122) (lanes 1-4) or GST-Xmcm2 (62-122)-S92A (lanes 5 and 6). Reactions were subjected to SDS-PAGE and both stained with Coomassie blue (top) and analyzed by phosphorimaging (bottom). In FIG. 8B, control eluate (lanes 1 and 2) and Xatr-XatripΔN222 complex (lanes 3 and 4) were incubated in the absence (lanes 1 and 3) or presence of GST-XtopBP1 (972-1279) (lanes 2 and 4) in kinase buffer containing 1 mM nonradioactive ATP and GST-Xchk1 (306-352). Reactions were subjected to SDS-PAGE and both stained with Coomassie blue (top) and immunoblotted with antibodies against phospho-S344 of Xchk1 (bottom). In FIG. 8C, control eluate (lanes 1 and 2) and Xatr-XatripΔN222 complex (lanes 3 and 4) were incubated in the absence (lanes 1 and 3) or presence of GST-XtopBP1 (972-1279) (lanes 2 and 4) in kinase buffer containing 1 mM nonradioactive ATP and Xchk1-Myc-His6. Reactions were processed for immunoblotting with anti-Myc antibodies (top) and antibodies against phospho-S344 of Xchk1 (bottom).

DETAILED DESCRIPTION OF THE INVENTION

(i) Overview

Figure 1:
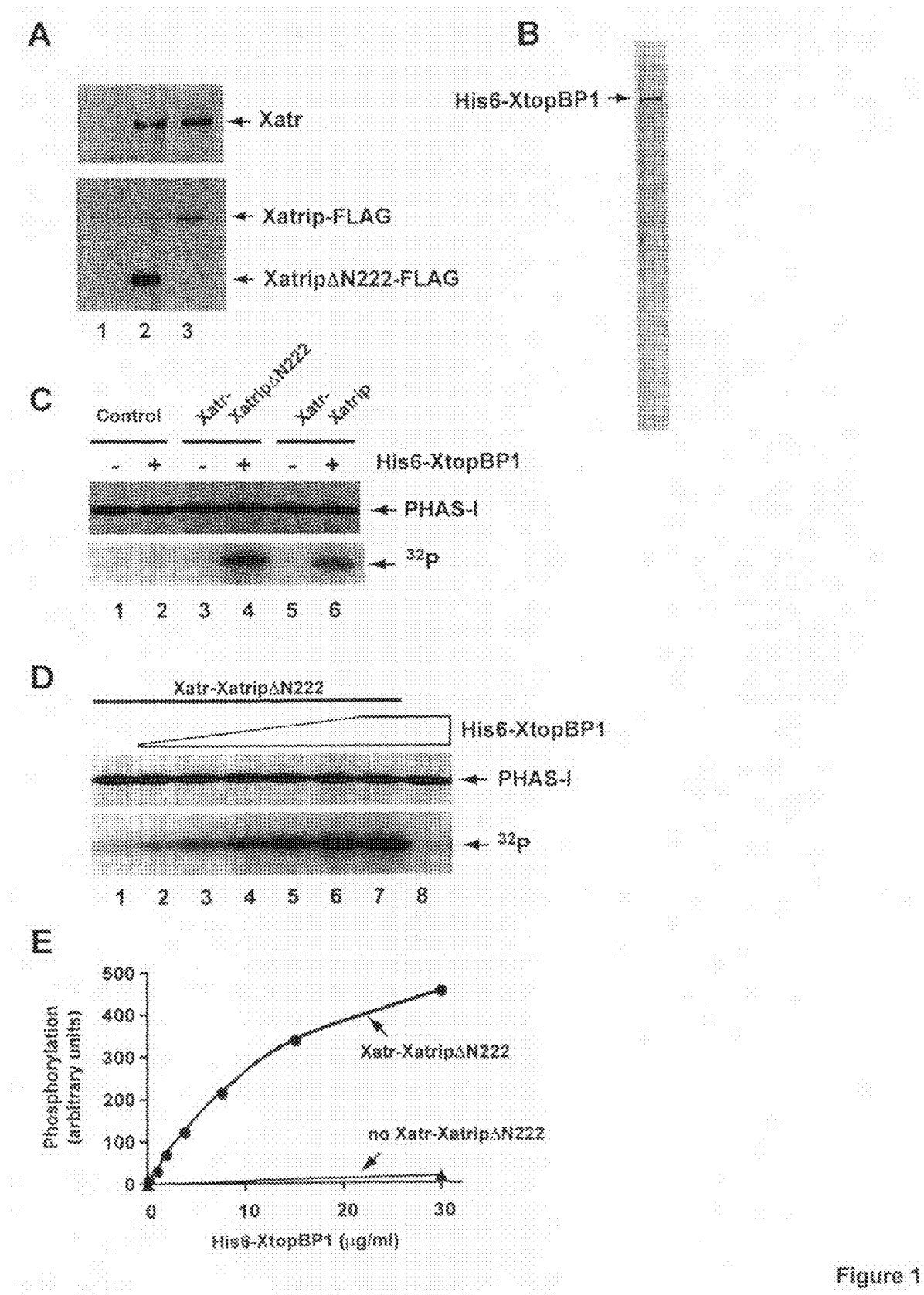
FIGS. 1A-1E show that recombinant XtopBP1 induces activation of the Xatr-Xatrip complex.

The present invention describes the use of specific modulators to modulate the activation of ATR (but not the related ATM) by TopBP1 and its related proteins. The invention is partly based on the serendipitous discovery that the TopBP1 family of proteins directly activates the checkpoint control protein ATR (but not its closely related ATM protein). The invention is also partly based on the finding that a unique fragment of the TopBP1 protein, the ATR activation domain (AAD), is necessary and sufficient for ATR activation.

Thus in one aspect, the invention provides a method for modulating (e.g., increasing or decreasing) ATR activation by TopBP1, comprising administering one or more modulator (e.g., activator or inhibitor) of TopBP1 activity. The modulator may affect the transcription and/or expression of TopBP1, affect the binding of TopBP1 to ATR or the ATR-ATRIP complex, and/or affect the activation of the ATR kinase activity by TopBP1.

The effect of the modulator on TopBP1 transcription/translation, binding to ATR or ATR-ATRIP complex, and/or activation of ATR kinase activity can be verified using any art recognized techniques, such as Northern blot, Western blot, various protein binding assays (Immuno-precipitation-Western etc.), ATR kinase assay, but to name a few.

In certain embodiments, the modulator is an inhibitor of TopBP1 activity. Such inhibitors can be any type of molecules, such as (without limiting): an siRNA (small interfering RNA), an shRNA (short hairpin RNA), an antisense oligonucleotide, a ribozyme, a peptide, a DNA enzyme, a Morpholino antisense, a small molecule inhibitor, an antibody or functional fragment thereof, a dominant negative mutant TopBP1 or fragment thereof, or a peptidomimetic.

In certain other embodiments, the modulator is an activator of TopBP1 activity. Representative activators include (without limiting): a TopBP1 activator (e.g., oligonucleotide duplex AT70), a TopBP1 transcriptional activator, a TopBP1 stabilizer, or a polypeptide comprising an ATR activation domain of TopBP1 (infra).

Details of these specific classes of modulators are described below.

In certain embodiments, only one TopBP1 modulator is used, while in other embodiments, more than one TopBP1 modulators are used (e.g., all activators, or all inhibitors).

In certain embodiments, the method further comprises contacting ATR with one or more modulators of ATR activity. For example, ATRIP and RPA (replication protein A) may be used as modulators of ATR function.

The methods of the invention may be carried out in vitro as well as in vivo. For example, when carried out in vitro, the modulators may be added to a reaction mixture (such as cell or embryo lysate, or test tube with defined components) comprising ATR and TopBP1. Alternatively, when carried out in vivo, the modulators may be administered to cells or animals, and upon entering the cells, the modulator may regulate the activation of ATR by TopBP1.

In a preferred embodiment, the cell is a vertebrate cell, such as a mammalian cell, a bird cell (such as a chicken cell or embryo), a fish cell (such as zebrafish), or a *Xenopus* cell or embryo. A preferred mammalian cell is a human cell, or a cell from a non-human mammal (such as mouse, rat, rabbit, hamster, cat, dog, cattle, pig, sheep, goat, horse, monkey or other non-human primates).

In certain embodiments, the ATR protein is a human ATR. An exemplary human ATR protein has the NCBI RefSeq ID of NP_001175 (incorporated by reference), which sequence is listed below. Other human ATR with polymorphism or other minor sequence variations are also within the scope of the invention.

```
MGEHGLELASMIPALRELGSATPEEYNTVVQKPRQILCQFIDRILTDVNVVAVELVKKTDSQPTSVMLLDFIQ    (SEQ ID NO: 3)
HIMKSSPLMFVNVSGSHERKGSCIEFSNWIITRLLRIAATPSCHLLHKKICEVICSLLFLFKSKSPAIFGVLT
KELLQLFEDLVYLHRRNVMGHAVEWPVVMSRFLSQLDEHMGYLQSAPLQLMSMQNLEFIEVTLLMVLTRIIAI
VFFRRQELLLWQIGCVLLEYGSPKIKSLAISFLTELFQLGGLPAQPASTFFSSFLELLKHLVEMDTDQLKLYE
EPLSKLIKTLFPFEAEAYRNIEPVYLNNLLEKLCVMFEDGVLMRLKSDLLKAALCHLLQYFLKFVPAGYESAL
QVRKVYVRNICKALLDVLGIEVDAEYLLGPLYAALKMESMEIIEEIQCQTQQENLSSNSDGISPKRRRLSSSL
NPSKRAPKQTEEIKHVDMNQKSILWSALKQKAESLQISLEYSGLKNPVIEMLEGIAVVLQLTALCTVHCSHQN
MNCRTFKDCQHKSKKKPSVVITWMSLDFYTKVLKSCRSLLESVQKLDLEATIDKVVKIYDALIYMQVNSSFED
HILEDLCGMLSLPWIYSHSDDGCLKLTTFAANLLTLSCRISDSYSPQAQSRCVFLLTLFPRRIFLEWRTAVYN
WALQSSHEVIRASCVSGFFILLQQQNSCNRVPKILIDKVKDDSDIVKKEFASILGQLVCTLHGMFYLTSSLTE
PFSEHGHVDLFCRNLKATSQHECSSSQLKASVCKPFLFLLKKKIPSPVKLAFIDNLHHLCKHLDFREDETDVK
AVLGTLLNLMEDPDKDVRVAFSGNIKHILESLDSEDGFIKELFVLRMKEAYTHAQISRNNELKDTLILTTGDI
GRAAKGDLVPFALLHLLHCLLSKSASVSGAAYTEIRALVAAKSVKLQSFFSQYKKPICQFLVESLHSSQMTAL
PNTPCQNADVRKQDVAHQREMALNTLSEIANVFDFPDLNRFLTRTLQVLLPDLAAKASPAASALIRTLGKQLN
VNRREILINNFKYIFSHLVCSCSKDELERALHYLKNETEIELGSLLRQDFQGLHNELLLRIGEHYQQVFNGLS
ILASFASSDDPYQGPRDIISPELMADYLQPKLLGILAFFNMQLLSSSVGIEDKKMALNSLMSLMKLMGPKHVS
SVRVKMMTTLRTGLRFKDDFPELCCRAWDCFVRCLDHACLGSLLSHVIVALLPLIHIQPKETAAIFHYLIIEN
RDAVQDFLHEIYFLPDHPELKKIKAVLQEYRKETSESTDLQTTLQLSMKAIQHENVDVRIHALTSLKETLYKN
QEKLIKYATDSETVEPIISQLVTVLLKGCQDANSQARLLCGECLGELGAIDPGRLDFSTTETQGKDFTFVTGV
EDSSFAYGLLMELTRAYLAYADNSRAQDSAAYAIQELLSIYDCREMETNGPGHQLWRRFPEHVREILEPHLNT
RYKSSQKSTDWSGVKKPIYLSKLGSNFAEWSASWAGYLITKVRHDLASKIFTCCSIMMKHDFKVTIYLLPHIL
VYVLLGCNQEDQQEVYAEIMAVLKHDDQHTINTQDIASDLCQLSTQTVFSMLDHLTQWARHKFQALKAEKCPH
SKSNRNKVDSMVSTVDYEDYQSVTRFLDLIPQDTLAVASFRSKAYTRAVMHFESFITEKKQNIQEHLGFLQKL
YAAMHEPDGVAGVSAIRKAEPSLKEQILEHESLGLLRDATACYDRAIQLEPDQIIHYHGVVKSMLGLGQLSTV
ITQVNGVHANRSEWTDELNTYRVEAAWKLSQWDLVENYLAADGKSTTWSVRLGQLLLSAKKRDITAFYDSLKL
VRAEQIVPLSAASFERGSYQRGYEYIVRLHMLCELEHSIKPLFQHSPGDSSQEDSLNWVARLEMTQNSYRAKE
PILALRRALLSLNKRPDYNEMVGECWLQSARVARKAGHHQTAYNALLNAGESRLAELYVERAKWLWSKGDVHQ
ALIVLQKGVELCFPENETPPEGKNMLIHGRAMLLVGRFMEETANFESNAIMKKYKDVTACLPEWEDGHFYLAK
YYDKLMPMVTDNKMEKQGDLIRYIVLHFGRSLQYGNQFIYQSMPRMLTLWLDYGTKAYEWEKAGRSDRVQMRN
DLGKINKVITEHTNYLAPYQFLTAFSQLISRICHSHDEVFVVLMEIIAKVFLAYPQQANWMMTAVSKSSYPMR
VNRCKEILNKAIHMKKSLEKFVGDATRLTDKLLELCNKPVDGSSSTLSMSTHFKMLKKLVEEATFSEILIPLQ
SVMIPTLPSILGTHANHASHEPFPGHWAYIAGFDDMVEILASLQKPKKISLKGSDGKFYIMMCKPKDDLRKDC
RLMEFNSLINKCLRKDAESRRRELHIRTYAVIPLNDECGIIEWVNNTAGLRPILTKLYKEKGVYMTGKELRQC
```

-continued

```
MLPKSAALSEKLKVFREFLLPRHPPIFHEWFLRTFPDPTSWYSSRSAYCRSTAVMSMVGYILGLGDRHGENIL
FDSLTGECVHVDFNCLFNKGETFEVPEIVPFRLTHNMVNGMGPMGTEGLFRRACEVTMRLMRDQREPLMSVLK
TFLHDPLVEWSKPVKGHSKAPLNETGEVVNEKAKTHVLDIEQRLQGVIKTRNRVTGLPLSIEGHVHYLIQEAT
DENLLCQMYLGWTPYM
```

A corresponding human ATR mRNA sequence is represented in RefSeq ID NM_001184 (incorporated by reference):

```
GCCTCCACACGGCTCCGTCGGGCGCCGCGCTCTTCCGGCAGCGGTACGTTTGGAGACGCCGGGAACCCGCGTT    (SEQ ID NO: 4)
GGCGTGGTTGACTAGTGCCTCGCAGCCTCAGCATGGGGGAACATGGCCTGGAGCTGGCTTCCATGATCCCCGC
CCTGCGGGAGCTGGGCAGTGCCACACCAGAGGAATATAATACAGTTGTACAGAAGCCAAGACAAATTCTGTGT
CAATTCATTGACCGGATACTTACAGATGTAAATGTTGTTGCTGTAGAACTTGTAAAGAAAACTGACTCTCAGC
CAACCTCCGTGATGTTGCTTGATTTCATCCAGCATATCATGAAATCCTCCCCACTTATGTTTGTAAATGTGAG
TGGAAGCCATGAGCGCAAAGGCAGTTGTATTGAATTCAGTAATTGGATCATAACGAGACTTCTGCGGATTGCA
GCAACTCCCTCCTGTCATTTGTTACACAAGAAAATCTGTGAAGTCATCTGTTCATTATTATTTCTTTTTAAAA
GCAAGAGTCCTGCTATTTTTGGGGTACTCACAAAAGAATTATTACAACTTTTTGAAGACTTGGTTTACCTCCA
TAGAAGAAATGTGATGGGTCATGCTGTGGAATGGCCAGTGGTCATGAGCCGATTTTTAAGTCAATTAGATGAA
CACATGGGATATTTACAATCAGCTCCTTTGCAGTTGATGAGTATGCAAAATTTAGAATTTATTGAAGTCACTT
TATTAATGGTTCTTACTCGTATTATTGCAATTGTGTTTTTTAGAAGGCAAGAACTCTTACTTTGGCAGATAGG
TTGTGTTCTGCTAGAGTATGGTAGTCCAAAAATTAAATCCCTAGCAATTAGCTTTTTAACAGAACTTTTTCAG
CTTGGAGGACTACCAGCACAACCAGCTAGCACTTTTTTCAGCTCATTTTTGGAATTATTAAAACACCTTGTAG
AAATGGATACTGACCAATTGAAACTCTATGAAGAGCCATTATCAAAGCTGATAAAGACACTATTTCCCTTTGA
AGCAGAAGCTTATAGAAATATTGAACCTGTCTATTTAAATATGCTGCTGGAAAAACTCTGTGTCATGTTTGAA
GACGGTGTGCTCATGCGGCTTAAGTCTGATTTGCTAAAAGCAGCTTTGTGCCATTTACTGCAGTATTTCCTTA
AATTTGTGCCAGCTGGGTATGAATCTGCTTTACAAGTCAGGAAGGTCTATGTGAGAAATATTTGTAAAGCTCT
TTTGGATGTGCTTGGAATTGAGGTAGATGCAGAGTACTTGTTGGGCCCACTTTATGCAGCTTTGAAAATGGAA
AGTATGGAAATCATTGAGGAGATTCAATGCCAAACTCAACAGGAAAACCTCAGCAGTAATAGTGATGGAATAT
CACCCAAAAGGCGTCGTCTCAGCTCGTCTCTAAACCCTTCTAAAAGAGCACCAAAACAGACTGAGGAAATTAA
ACATGTGGACATGAACCAAAAGAGCATATTATGGAGTGCACTGAAACAGAAAGCTGAATCCCTTCAGATTTCC
CTTGAATACAGTGGCCTAAAGAATCCTGTTATTGAGATGTTAGAAGGAATTGCTGTTGTCTTACAACTGACTG
CTCTGTGTACTGTTCATTGTTCTCATCAAAACATGAACTGCCGTACTTTCAAGGACTGTCAACATAAATCCAA
GAAGAAACCTTCTGTAGTGATAACTTGGATGTCATTGGATTTTTACACAAAAGTGCTTAAGAGCTGTAGAAGT
TTGTTAGAATCTGTTCAGAAACTGGACCTGGAGGCAACCATTGATAAGGTGGTGAAAATTTATGATGCTTTGA
TTTATATGCAAGTAAACAGTTCATTTGAAGATCATATCCTGGAAGATTTATGTGGTATGCTCTCACTTCCATG
GATTTATTCCCATTCTGATGATGGCTGTTTAAAGTTGACCACATTTGCCGCTAATCTTCTAACATTAAGCTGT
AGGATTTCAGATAGCTATTCACCACAGGCACAATCACGATGTGTGTTTCTTCTGACTCTGTTTCCAAGAAGAA
TATTCCTTGAGTGGAGAACAGCAGTTTACAACTGGGCCCTGCAGAGCTCCCATGAAGTAATCCGGGCTAGTTG
TGTTAGTGGATTTTTTATCTTATTGCAGCAGCAGAATTCTTGTAACAGAGTTCCCAAGATTCTTATAGATAAA
GTCAAAGATGATTCTGACATTGTCAAGAAAGAATTTGCTTCTATACTTGGTCAACTTGTCTGTACTCTTCACG
GCATGTTTTATCTGACAAGTTCTTTAACAGAACCTTTCTCTGAACACGGACATGTGGACCTCTTCTGTAGGAA
CTTGAAAGCCACTTCTCAACATGAATGTTCATCTTCTCAACTAAAAGCTTCTGTCTGCAAGCCATTCCTTTTC
```

-continued

```
CTACTGAAAAAAAAAATACCTAGTCCAGTAAAACTTGCTTTCATAGATAATCTACATCATCTTTGTAAGCATC
TTGATTTTAGAGAAGATGAAACAGATGTAAAAGCAGTTCTTGGAACTTTATTAAATTTAATGGAAGATCCAGA
CAAAGATGTTAGAGTGGCTTTTAGTGGAAATATCAAGCACATATTGGAATCCTTGGACTCTGAAGATGGATTT
ATAAAGGAGCTTTTTGTCTTAAGAATGAAGGAAGCATATACACATGCCCAAATATCAAGAAATAATGAGCTGA
AGGATACCTTGATTCTTACAACAGGGGATATTGGAAGGGCCGCAAAAGGAGATTTGGTACCATTTGCACTCTT
ACACTTATTGCATTGTTTGTTATCCAAGTCAGCATCTGTCTCTGGAGCAGCATACACAGAAATTAGAGCTCTG
GTTGCAGCTAAAAGTGTTAAACTGCAAAGTTTTTTCAGCCAGTATAAGAAACCCATCTGTCAGTTTTTGGTAG
AATCCCTTCACTCTAGTCAGATGACAGCACTTCCGAATACTCCATGCCAGAATGCTGACGTGCGAAAACAAGA
TGTGGCTCACCAGAGAGAAATGGCTTTAAATACGTTGTCTGAAATTGCCAACGTTTTCGACTTTCCTGATCTT
AATCGTTTTCTTACTAGGACATTACAAGTTCTACTACCTGATCTTGCTGCCAAAGCAAGCCCTGCAGCTTCTG
CTCTCATTCGAACTTTAGGAAAACAATTAAATGTCAATCGTAGAGAGATTTTAATAAACAACTTCAAATATAT
TTTTTCTCATTTGGTCTGTTCTTGTTCCAAAGATGAATTAGAACGTGCCCTTCATTATCTGAAGAATGAAACA
GAAATTGAACTGGGGAGCCTGTTGAGACAAGATTTCCAAGGATTGCATAATGAATTATTGCTGCGTATTGGAG
AACACTATCAACAGGTTTTTAATGGTTTGTCAATACTTGCCTCATTTGCATCCAGTGATGATCCATATCAGGG
CCCGAGAGATATCATATCACCTGAACTGATGGCTGATTATTTACAACCCAAATTGTTGGGCATTTTGGCTTTT
TTTAACATGCAGTTACTGAGCTCTAGTGTTGGCATTGAAGATAAGAAAATGGCCTTGAACAGTTTGATGTCTT
TGATGAAGTTAATGGGACCCAAACATGTCAGTTCTGTGAGGGTGAAGATGATGACCACACTGAGAACTGGCCT
TCGATTCAAGGATGATTTTCCTGAATTGTGTTGCAGAGCTTGGGACTGCTTTGTTCGCTGCCTGGATCATGCT
TGTCTGGGCTCCCTTCTCAGTCATGTAATAGTAGCTTTGTTACCTCTTATACACATCCAGCCTAAAGAAACTG
CAGCTATCTTCCACTACCTCATAATTGAAAACAGGGATGCTGTGCAAGATTTTCTTCATGAAATATATTTTTT
ACCTGATCATCCAGAATTAAAAAAGATAAAAGCCGTTCTCCAGGAATACAGAAAGGAGACCTCTGAGAGCACT
GATCTTCAGACAACTCTTCAGCTCTCTATGAAGGCCATTCAACATGAAAATGTCGATGTTCGTATTCATGCTC
TTACAAGCTTGAAGGAAACCTTGTATAAAAATCAGGAAAAACTGATAAAGTATGCAACAGACAGTGAAACAGT
AGAACCTATTATCTCACAGTTGGTGACAGTGCTTTTGAAAGGTTGCCAAGATGCAAACTCTCAAGCTCGGTTG
CTCTGTGGGGAATGTTTAGGGGAATTGGGGGCGATAGATCCAGGTCGATTAGATTTCTCAACAACTGAAACTC
AAGGAAAAGATTTTACATTTGTGACTGGAGTAGAAGATTCAAGCTTTGCCTATGGATTATTGATGGAGCTAAC
AAGAGCTTACCTTGCGTATGCTGATAATAGCCGAGCTCAAGATTCAGCTGCCTATGCCATTCAGGAGTTGCTT
TCTATTTATGACTGTAGAGAGATGGAGACCAACGGCCCAGGTCACCAATTGTGGAGGAGATTTCCTGAGCATG
TTCGGGAAATACTAGAACCTCATCTAAATACCAGATACAAGAGTTCTCAGAAGTCAACCGATTGGTCTGGAGT
AAAGAAGCCAATTTACTTAAGTAAATTGGGTAGTAACTTTGCAGAATGGTCAGCATCTTGGGCAGGTTATCTT
ATTACAAAGGTTCGACATGATCTTGCCAGTAAAATTTTCACCTGCTGTAGCATTATGATGAAGCATGATTTCA
AAGTGACCATCTATCTTCTTCCACATATTCTGGTGTATGTCTTACTGGGTTGTAATCAAGAAGATCAGCAGGA
GGTTTATGCAGAAATTATGGCAGTTCTAAAGCATGACGATCAGCATACCATAAATACCCAAGACATTGCATCT
GATCTGTGTCAACTCAGTACACAGACTGTGTTCTCCATGCTTGACCATCTCACACAGTGGGCAAGGCACAAAT
TTCAGGCACTGAAAGCTGAGAAATGTCCACACAGCAAATCAAACAGAAATAAGGTAGACTCAATGGTATCTAC
TGTGGATTATGAAGACTATCAGAGTGTAACCCGTTTTCTAGACCTCATACCCCAGGATACTCTGGCAGTAGCT
TCCTTTCGCTCCAAAGCATACACACGAGCTGTAATGCACTTTGAATCATTTATTACAGAAAAGAAGCAAAATA
TTCAGGAACATCTTGGATTTTTACAGAAATTGTATGCTGCTATGCATGAACCTGATGGAGTGGCCGGAGTCAG
TGCAATTAGAAAGGCAGAACCATCTCTAAAAGAACAGATCCTTGAACATGAAAGCCTTGGCTTGCTGAGGGAT
GCCACTGCTTGTTATGACAGGGCTATTCAGCTAGAACCAGACCACAGATCATTCATTATCATGGTGTAGTAAAGT
CCATGTTAGGTCTTGGTCAGCTGTCTACTGTTATCACTCAGGTGAATGGAGTGCATGCTAACAGGTCCGAGTG
```

-continued

```
GACAGATGAATTAAACACGTACAGAGTGGAAGCAGCTTGGAAATTGTCACAGTGGGATTTGGTGGAAAACTAT
TTGGCAGCAGATGGAAAATCTACAACATGGAGTGTCAGACTGGGACAGCTATTATTATCAGCCAAAAAAGAG
ATATCACAGCTTTTTATGACTCACTGAAACTAGTGAGAGCAGAACAAATTGTACCTCTTTCAGCTGCAAGCTT
TGAAAGAGGCTCCTACCAACGAGGATATGAATATATTGTGAGATTGCACATGTTATGTGAGTTGGAGCATAGC
ATCAAACCACTTTTCCAGCATTCTCCAGGTGACAGTTCTCAAGAAGATTCTCTAAACTGGGTAGCTCGACTAG
AAATGACCCAGAATTCCTACAGAGCCAAGGAGCCTATCCTGGCTCTCCGGAGGGCTTTACTAAGCCTCAACAA
AAGACCAGATTACAATGAAATGGTTGGAGAATGCTGGCTGCAGAGTGCCAGGGTAGCTAGAAAGGCTGGTCAC
CACCAGACAGCCTACAATGCTCTCCTTAATGCAGGGGAATCACGACTCGCTGAACTGTACGTGGAAAGGGCAA
AGTGGCTCTGGTCCAAGGGTGATGTTCACCAGGCACTAATTGTTCTTCAAAAAGGTGTTGAATTATGTTTTCC
TGAAAATGAAACCCCACCTGAGGGTAAGAACATGTTAATCCATGGTCGAGCTATGCTACTAGTGGGCCGATTT
ATGGAAGAAACAGCTAACTTTGAAAGCAATGCAATTATGAAAAAATATAAGGATGTGACCGCGTGCCTGCCAG
AATGGGAGGATGGGCATTTTTACCTTGCCAAGTACTATGACAAATTGATGCCCATGGTCACAGACAACAAAAT
GGAAAAGCAAGGTGATCTCATCCGGTATATAGTTCTTCATTTTGGCAGATCTCTACAATATGGAAATCAGTTC
ATATATCAGTCAATGCCACGAATGTTAACTCTATGGCTTGATTATGGTACAAAGGCATATGAATGGGAAAAG
CTGGCCGCTCCGATCGTGTACAAATGAGGAATGATTTGGGTAAAATAAACAAGGTTATCACAGAGCATACAAA
CTATTTAGCTCCATATCAATTTTTGACTGCTTTTTCACAATTGATCTCTCGAATTTGTCATTCTCACGATGAA
GTTTTTGTTGTCTTGATGGAAATAATAGCCAAAGTATTTCTAGCCTATCCTCAACAAGCAATGTGGATGATGA
CAGCTGTGTCAAAGTCATCTTATCCCATGCGTGTGAACAGATGCAAGGAAATCCTCAATAAAGCTATTCATAT
GAAAAAATCCTTAGAGAAGTTTGTTGGAGATGCAACTCGCCTAACAGATAAGCTTCTAGAATTGTGCAATAAA
CCGGTTGATGGAAGTAGTTCCACATTAAGCATGAGCACTCATTTTAAAATGCTTAAAAAGCTGGTAGAAGAAG
CAACATTTAGTGAAATCCTCATTCCTCTACAATCAGTCATGATACCTACACTTCCATCAATTCTGGGTACCCA
TGCTAACCATGCTAGCCATGAACCATTTCCTGGACATTGGGCCTATATTGCAGGGTTTGATGATATGGTGGAA
ATTCTTGCTTCTCTTCAGAAACCAAAGAAGATTTCTTTAAAAGGCTCAGATGGAAAGTTCTACATCATGATGT
GTAAGCCAAAAGATGACCTGAGAAAGGATTGTAGACTAATGGAATTCAATTCCTTGATTAATAAGTGCTTAAG
AAAAGATGCAGAGTCTCGTAGAAGAGAACTTCATATTCGAACATATGCAGTTATTCCACTAAATGATGAATGT
GGGATTATTGAATGGGTGAACAACACTGCTGGTTTGAGACCTATTCTGACCAAACTATATAAAGAAAAGGGAG
TGTATATGACAGGAAAAGAACTTCGCCAGTGTATGCTACCAAAGTCAGCAGCTTTATCTGAAAAACTCAAAGT
ATTCCGAGAATTTCTCCTGCCCAGGCATCCTCCTATTTTTCATGAGTGGTTTCTGAGAACATTCCCTGATCCT
ACATCATGGTACAGTAGTAGATCAGCTTACTGCCGTTCCACTGCAGTAATGTCAATGGTTGGTTATATTCTGG
GGCTTGGAGACCGTCATGGTGAAAATATTCTCTTTGATTCTTTGACTGGTGAATGCGTACATGTAGATTTCAA
TTGTCTTTTCAATAAGGGAGAAACCTTTGAAGTTCCAGAAATTGTGCCATTTCGCCTGACTCATAATATGGTT
AATGGAATGGGTCCTATGGGAACAGAGGGTCTTTTTCGAAGAGCATGTGAAGTTACAATGAGGCTGATGCGTG
ATCAGCGAGAGCCTTTAATGAGTGTCTTAAAGACTTTTCTACATGATCCTCTTGTGGAATGGAGTAAACCAGT
GAAAGGGCATTCCAAAGCGCCACTGAATGAAACTGGAGAAGTTGTCAATGAAAAGGCCAAGACCCATGTTCTT
GACATTGAGCAGCGACTACAAGGTGTAATCAAGACTCGAAATAGAGTGACAGGACTGCCGTTATCTATTGAAG
GACATGTGCATTACCTTATACAAGAAGCTACTGATGAAAACTTACTATGCCAGATGTATCTTGGTTGGACTCC
ATATATGTGAAATGAAATTATGTAAAAGAATATGTTAATAATCTAAAAGTAATGCATTTGGTATGAATCTGTG
GTTGTATCTGTTCAATTCTAAAGTACAACATAAATTTACGTTCTCAGCAACTGTTATTTCTCTCTGATCATTA
ATTATATGTAAAATAATATACATTCAGTTATTAAGAAATAAACTGCTTTCTTAATAAAAAAAAAAAAAAAAAA
AAAAAAAAAAAAAAA
```

In certain embodiments, the ATR protein is a *Xenopus* ATR. An exemplary *Xenopus* ATR protein has the SwissProt Accession ID of Q9DE14 (incorporated by reference), which sequence is listed below. Other *Xenopus* ATR with polymorphism or other minor sequence variations are also within the scope of the invention.

```
MATDPGLEMASMIPALRELASAGAEEYNTTVQKPRQILCQFIDRILTDVDVVAVELSKNTDSQPSSVMLLDFI    (SEQ ID NO: 5)
QHIMKSTPLMFLSANNGDQSAETNQNCVAFSNWIISRLLRIGATPSCKALHRKIAEVIRSLLFLFKNKSSFLF
GVFTKDLLHLFEDLIYIHEQNMEKSVVWPVTISRFLSNASENQTYLRCTQFQLLNMQNIEPLESTLLMVLMDN
EHDISPVFFQRQNLLLWGIGCSLLDYGSTPLKIQALHFLRQLIKLGGPPEQGAYFFFIVFFGILTCIKDMDLE
EVSLYEMPLLKLVKVLFPFESKSYLNIEPVYLNMLLEKLAALFDGGILSNIQSAPLKEALCYMVHYFLSIVPP
GYESAKEVREAHVRCICRAFVDVLGLQSKQEYLVCPLHEALRIENLVFMQQQRMQPLSTDSEGGGSSSSDEVQ
EKRPRLSLTAKPLRRNTPSVPAPVDMKTKSILWKAVSAKFSSILCKLEGDEVTDEEMVSLLEGLNTTVRVAAL
NTVHIFTNDSTDTDQLVSDLSNTSGIQSVEIVPHVFWLSPEDILKILKICRKVLDSAHQRANINDILMKIIKI
FDAILYIHAGNRLNDQTLKDLCSMISLPWLQNHSNHASFKVASFDPTLMTISERIGQHYSPEIQSQLVFLLCL
FPKMLCPEWRLAVYQWALDSPHEIVRARCIKGFPVLLCNVSQQGYGPIPKILIDCLNDASELVKKELANSVGM
FASGLACGFELQYSPTAPTAAESEFLCSSLTVTALPSSKLSRMTASALKPFLALLNRNMPSSVKMAFIENMPM
LFAHLSLEKDDLDSRTVIESLLNLMEDPDKDVRTAFSGNIKHLLACADCEDGYLKEIVVSRMKKAYTDAKMSR
DNEMKDTLILTTGDIGRAAKGELVPFALLHLLHCLLSKSPCVAGASYTEIRSLAAAKSTSLHIFFSQYKKPIC
QFLIESLHSSQAALLTNTPGRSSEMQKQEATHHREAALDILSEIANVFDFPDLNRFLTRTLQLLLPYLAAKAS
PTASTLIRTIAKQLNVNRREILINNFKYIFSHLVCSCTKDELEKSLHYLKNETEIELGSLLRQDYQGLHNELL
LRLGEHYQQVFSGLSILATYASNDDPYQGPRNFAKPEIMADYLQPKLLGILAFFNMHLLSSSIGIEDKKMALN
SLVSLMKLMGPKHISSVRVKMMTTLRTGLRYKEEFPGLCCSAWDLFVRCLDQAYLGPLLSHVIVALLPLLHIQ
PKETVAVFRYLIVENRDAVQDFLHEIYFLPDHPELKEIQKVLQEYRKETTKSTDLQTAMQLSIRAIQHENVDV
RMHALTSLKETLYKNQAKLLQYSTDSETVEPVISQLVTVLLIGCQDANPQARLFCGECLGQLGAIDPGRLDFS
PSETQGKGFTFVSGVEDSDFAYELLTEQTRAFLAYADNVRAQDSAAYAIQELLSIFECKEGRTDCPGRRLWRR
FPEHVQEILEPHLNTRYKSSRKAVNWSRVKKPIYLSKLGNNFADWSATWAGYLITKVRHELARRVFSCCSIMM
KHDFKVTIYLLPHILVYVLLGCNKEDQQEVYAEIMAVLKHEDPLMRRLQDSASDLSQLSTQTVFSMLDHLTQW
AREKFQALNAEKTNPKPGTRGEPKAVSNEDYGEYQNVTRFLDLIPQDTLAVASFRSKAYTRALMHFESFIMEK
KQEIQEHLGFLQKLYAAMHEPDGVAGVSAIRKKEASLKEQILEHESIGLLRDATACYDRAIQLKPEEIIHYHG
VVKSMLGLGQLSTVITQVNGILNSRSEWTAELNTYRVEAAWKLSQWDLVEEYLSADRKSTTWSIRLGQLLLSA
KKGERDMFYETLKVVRAEQIVPLSAASFERGSYQRGYEYIVRLHMLCELEHSVKMFLQKPSVEPAVDSLNLPA
RLEMTQNSYRAREPILAVRRALQTINKRPNHADMIGECWLQSARVARKAGHHQTAYNALLNAGESRLSELNVE
RAKWLWSKGDVHQALIVLQKGAELFLSSTSAPPEQQLIHGRAMLLVGRLMEETANFESNAVMKKYKDVTALLP
EWEDGHFYLAKYYDKLMPMVTDNKMEKQGDLIRYIVLHFGRSLQFGNQYIYQSMPRMLSLWLDFGAKVYEWEK
AGRADRLQMKNELMKINKVISDHKNQLAPYQFLTAFSQLISRICHSHDEVFAVLMEIVAKVFVAYPQQAMWMM
TAVSKSSYPMRVNRCKEILEKAIHMKPSLGKFIGDATRLTDKLLELCNKPVDGNTSTLSMNIHFKMLKKLVEE
TTFSEILIPLQSVMIPTLPSTAGKRDHADHDPFPGHWAYLSGFDDAVEILPSLQKPKKISLKGSDGKSYIMMC
KPKDDLRKDCRLMEFNSLINKCLRKDAESRRRELHIRTYAVIPLNDECGIIEWVNNTAGFRNILIKLYKEKGI
YMGGKELRQCMLPKSAPLQEKLKVFKEALLPRHPPLFHEWFLRTFPDPTSWYNSRSAYCRSTAVMSMVGYILG
LGDRHGENILFDSLTGECVHVDFNCLFNKGETFEVPEIVPFRLTHNMVNGMGPMGTEGLFRRACEVIMRLMRE
QRESLMSVLKPFLHDPLVEWSKPARGSSKGQVNETGEVMNEKAKTHVLDIEQRLQGVIKTRNRVKGLPLSIEG
HVHYLIQEATDENLLSQMYLGWAPYM
```

A representative *Xenopus* ATR mRNA sequence is represented in GenBank Accession No. AF320125 (incorporated by reference):

```
TTCTAGCTCTGGGACTGAGCTGCTACCATGGCTACTGACCCCGGTCTTGAAATGGCCTCTATGATCCCGGCCT    (SEQ ID NO: 6)
TGCGTGAACTTGCCAGTGCCGGGGCAGAGGAATATAACACAACTGTTCAGAAACCAAGACAAATCCTTTGCCA
GTTTATAGACCGGATTCTGACAGATGTGGACGTTGTTGCTGTGGAGCTTTCAAAGAATACTGATTCTCAGCCA
AGTTCTGTGATGTTGCTGGATTTTATTCAACACATTATGAAATCTACCCCATTAATGTTTCTCAGTGCAAATA
ACGGTGATCAGTCTGCTGAAACCAATCAGAACTGTGTTGCATTTAGCAACTGGATCATTTCCCGGCTCTTACG
CATTGGGGCTACGCCAAGCTGCAAAGCTTTGCATAGAAAAATCGCTGAAGTCATCCGCTCCCTGCTTTTTCTT
TTCAAAAACAAGAGTTCCTTTCTATTTGGTGTTTTTACTAAAGATTTATTACATCTCTTTGAAGATCTTATCT
ACATACATGAACAAAACATGGAGAAATCCGTAGTTTGGCCTGTGACCATTTCTAGATTTTTAAGCAATGCATC
AGAAAACCAAACTTACTTAAGATGCACTCAATTTCAGTTGTTGAACATGCAGAACATTGAGCCTTTAGAATCC
ACTCTGCTAATGGTTTTGATGGATAACGAACATGATATTTCTCCAGTGTTTTTCCAAAGGCAGAACCTCCTCC
TCTGGGCATTGGGTGCTCCCTCTTGGACTATGGAAGTACACCACTGAAGATACAGGCATTGCATTTTTTAAG
ACAACTAATAAAATTAGGTGGTCCACCAGAACAGGGTGCATATTTTTCTTCATTGTGTTTTTTGGGATACTA
ACTTGTATAAAAGACATGGATTTAGAAGAAGTGTCTCTTTATGAGATGCCACTGTTGAAATTGGTAAAGGTTT
TGTTCCCATTTGAATCAAAATCTTACCTAAACATTGAACCTGTCTATCTGAATATGTTGCTGGAGAAACTTGC
TGCTCTCTTTGATGGAGGTATCTTGAGTAATATTCAGTCAGCTCCCTTGAAAGAAGCTCTTTGCTATATGGTC
CATTACTTCCTTAGCATTGTGCCTCCGGGCTATGAATCTGCCAAAGAAGTCCGAGAGGCACATGTTCGCTGCA
TCTGTAGAGCTTTTGTTGATGTCCTTGGACTTCAGAGCAAGCAAGAATACTTGGTCTGCCCCCTTCATGAAGC
ATTAAGAATAGAAAACCTGGTGTTCATGCAGCAGCAGCGCATGCAGCCCCTAAGCACAGACTCAGAGGGTGGT
GGGAGCAGCAGCAGCGATGAAGTCAAGAGAAACGACCACGTTTGAGTCTAACTGCAAAGCCTCTAAGAAGAA
ACACACCATCAGTGCCTGCTCCTGTGGATATGAAGACAAAGAGCATACTATGGAAAGCAGTGAGTGCGAAATT
CTCCTCTATTTTGTGCAAACTGGAAGGTGACGAAGTTACAGATGAAGAGATGGTTTCTTTATTGGAGGGTCTT
AATACAACTGTACGTGTTGCTGCTCTCAATACAGTTCATATCTTCACTAATGATTCCACAGATACTGATCAGT
TAGTATCTGACTTGAGCAATACTTCTGGCATTCAGTCGGTAGAAATAGTACCTCACGTTTTCTGGCTCAGTCC
AGAGGATATTCTAAAAATACTTAAAATTTGTAGAAAGGTTCTTGATTCTGCACACCAGAGAGCCAATATAAAT
GACATTCTGATGAAGATAATAAAAATATTTGATGCAATACTCTACATTCATGCAGGAAACAGATTAAATGACC
AAACTCTTAAGGATTTGTGCAGCATGATCTCATTACCCTGGCTTCAGAATCATTCAAATCATGCTTCCTTTAA
AGTGGCATCATTTGACCCAACATTGATGACCATAAGTGAGCGGATTGGCCAACATTACTCACCTGAAATTCAG
TCTCAACTTGTTTTCCTCCTGTGCCTGTTTCCAAAAATGTTATGCCCTGAGTGGAGATTAGCTGTGTACCAAT
GGGCATTGGATAGCCCACATGAGATTGTTCGTGCCCGTTGCATCAAAGGATTCCCTGTTCTTCTGTGCAATGT
TAGCCAGCAGGGTATGGTCCAATTCCCAAGATTTTAATCGACTGTTTGAATGATGCCTCTGAGCTGGTGAAG
AAGGAGTTAGCCAACTCAGTGGGTATGTTTGCCTCCGGCCTTGCTTGCGGTTTTGAGCTGCAATATTCCCCAA
CGGCACCTACTGCAGCAGAATCTGAGTTCCTTTGTAGCAGCCTGACAGTTACTGCTTTACCCTCATCGAAACT
TTCTCGTATGACCGCCTCTGCATTAAAACCATTCCTGGCACTGCTTAATCGAAACATGCCAAGCTCCGTCAAA
ATGGCATTTATTGAAAATATGCCCATGCTGTTTGCTCACCTCTCTCTTGAGAAAGATGATTTGGATTCCCGAA
CTGTGATTGAATCATTGTTAAACCTAATGGAGGACCCAGACAAGGATGTAAGGACAGCTTTCAGTGGGAACAT
CAAACACCTGTTGGCGTGTGCAGACTGTGAGGACGGATATCTAAAGGAGATTGTAGTCTCAAGGATGAAAAAA
GCATATACAGATGCCAAGATGTCGCGTGACAATGAGATGAAGGACACTCTCATTCTTACAACTGGGGATATAG
GAAGGGCAGCAAAAGGAGAGTTGGTACCATTTGCACTGTTGCATCTGCTGCATTGCCTGCTGTCTAAATCCCC
```

-continued

```
ATGTGTGGCAGGTGCTTCTTACACAGAAATCCGATCTCTTGCAGCAGCAAAGTCCACCAGTCTGCATATCTTT
TTTAGCCAGTACAAGAAACCGATTTGTCAGTTCCTTATAGAATCGCTTCACTCAAGCCAGGCAGCCCTTCTGA
CCAACACACCTGGCCGCAGCAGTGAAATGCAGAAGCAGGAGGCAACACATCATAGGGAAGCTGCACTTGACAT
CTTATCCGAAATAGCAAATGTATTTGATTTCCCAGACTTAAACCGCTTTTTAACGAGGACTTTGCAACTTTTG
CTTCCATATCTTGCTGCCAAAGCTAGTCCAACAGCCTCTACTCTGATAAGAACGATTGCCAAACAACTTAATG
TGAATCGAAGGGAGATCCTGATCAATAACTTCAAGTATATATTCTCTCACTTGGTTTGTTCTTGCACAAAAGA
TGAGCTGGAAAAGTCGCTTCATTACCTAAAGAATGAAACAGAAATTGAGCTGGGTAGTTTACTGAGACAGGAC
TACCAGGGACTGCACAATGAACTACTTTTGCGCCTGGGTGAGCACTATCAGCAGGTCTTTAGTGGGCTGTCCA
TATTAGCAACATATGCATCCAACGATGATCCATATCAGGGACCTAGGAATTTTGCAAAGCCAGAAATAATGGC
AGATTATTTGCAACCAAAGCTTTTAGGAATTTTGGCTTTCTTTAATATGCACCTGTTGAGCTCCAGCATTGGC
ATTGAAGACAAGAAAATGGCCTTGAACAGTCTGGTTTCTTTAATGAAACTGATGGGACCAAAGCATATAAGTT
CCGTTAGGGTCAAGATGATGACGACCTTGAGAACTGGCCTACGTTATAAAGAGGAATTTCCGGGGCTTTGCTG
CAGTGCATGGGACTTGTTTGTTCGCTGCCTGGATCAAGCCTATCTGGGCCCGCTCCTCAGTCATGTGATTGTT
GCACTGTTGCCTCTGTTGCACATCCAGCCTAAAGAAACTGTTGCTGTGTTCCGCTATCTCATAGTAGAGAACA
GGGATGCTGTTCAGGATTTCCTTCATGAAATATATTTTCTGCCTGATCATCCAGAATTGAAAGAAATCCAGAA
GGTTCTACAAGAATACAGGAAAGAAACCACCAAAAGCACAGATCTGCAGACAGCCATGCAGCTGTCTATTCGA
GCCATTCAGCATGAAAATGTGGATGTTCGCATGCATGCCCTTACTAGTCTGAAAGAAACACTCTACAAGAACC
AGGCTAAACTGTTGCAGTATTCAACAGACAGTGAAACTGTAGAACCAGTTATCTCCCAGCTGGTAACAGTTCT
CTTAATTGGATGCCAAGATGCCAATCCACAAGCCCGTCTATTTTGTGGTGAATGCCTTGGCCAACTTGGAGCC
ATTGATCCTGGGAGATTGGATTTCTCACCCAGTGAAACACAAGGGAAAGGTTTTACTTTTGTTTCAGGAGTTG
AAGATTCAGACTTTGCCTATGAGTTGCTCACAGAGCAAACTAGAGCATTTCTTGCCTATGCTGATAATGTCCG
CGCCCAGGACTCTGCTGCCTATGCTATACAGGAGCTTCTCTCTATCTTCGAGTGCAAAGAAGGAAGGACTGAT
TGTCCTGGGCGTAGGCTGTGGAGGAGATTCCCAGAACATGTTCAAGAAATATTGGAGCCACATCTTAATACTA
GATACAAGAGTTCCAGAAAGGCTGTAAACTGGTCCAGAGTGAAAAAGCCCATTTATTTGAGCAAGTTAGGAAA
TAACTTTGCAGACTGGTCAGCAACATGGGCAGGTTACCTCATAACTAAGGTTCGACATGAGCTTGCCAGGAGA
GTTTTCAGCTGTTGTAGTATAATGATGAAGCATGACTTCAAAGTGACCATTTATCTGCTCCCACATATTTTGG
TCTATGTTTTGTTGGGATGTAACAAAGAAGATCAGCAAGAGGTATATGCAGAAATTATGGCAGTGTTAAAGCA
TGAAGATCCACTAATGCGTCGGTTACAGGACAGCGCCTCAGATCTGAGTCAGCTCAGCACCCAAACAGTCTTT
TCAATGCTTGATCATCTTACTCAGTGGGCACGGGAGAAATTCCAGGCACTAAATGCTGAGAAAACAAACCCCA
AACCAGGAACCAGAGGGGAACCAAAGGCAGTGTCTAATGAAGACTATGGAGAGTATCAGAATGTAACAAGGTT
TTTAGATCTTATACCGCAGGATACTTTGGCTGTTGCTTCCTTTCGTTCCAAAGCTTATACTAGAGCTCTCATG
CATTTTGAATCCTTTATAATGGAAAAGAAACAAGAAATTCAGGAGCACCTTGGATTTCTTCAGAAACTGTATG
CTGCTATGCATGAGCCAGATGGAGTAGCTGGGGTAAGCGCCATTCGCAAGAAAGAAGCTTCTCTGAAAGAACA
GATCTTGGAGCATGAAAGTATTGGTCTGTTGAGAGATGCCACTGCTTGCTATGATAGAGCTATTCAGCTAAAG
CCTGAGGAGATAATTCACTATCATGGGGTAGTGAAATCTATGCTTGGTCTTGGCCAGTTGTCTACTGTAATTA
CGCAAGTTAACGGCATTTTGAATAGCAGGTCGGAATGGACAGCTGAACTAAGCACATACAGAGTAGAAGCAGC
ATGGAAACTCTCACAGTGGGATTTAGTGGAGGAATACTTATCTGCAGACAGAAAATCTACCACATGGAGCATT
AGGCTGGGGCAACTCCTGCTTTCAGCTAAAAGGGGGAGAGATATGTTTATGAAACGCTCAAAGTAGTCC
GAGCCGAACAAATTGTTCCACTGTCTGCTGCCAGCTTTGAGAGGGCTCCTACCAACGAGGATATGAGTACAT
AGTAAGGTTGCACATGTTATGTGAGTTGGAGCACAGTGTAAAAATGTTTCTTCAGAAACCTTCTGTTGAGCCT
GCAGTAGACTCTTTAAACTTGCCAGCACGGCTAGAAATGACACAGAATTCCTACAGAGCAAGAGAGCCCATTT
```

-continued

```
TGGCAGTTCGCAGGGCACTACAAACAATCAACAAAAGGCCTAATCATGCAGATATGATTGGTGAGTGTTGGCT

GCAAAGTGCTCGAGTTGCGCGTAAGGCTGGGCATCACCAGACTGCTTACAATGCTCTGCTTAATGCTGGGGAG

TCCAGACTGTCTGAGCTCAATGTTGAACGGGCGAAGTGGCTCTGGTCCAAGGGTGATGTACATCAAGCTCTCA

TTGTTCTCCAGAAGGGAGCAGAACTGTTCCTGTCAAGTACCAGCGCTCCACCAGAACAGCAGCTTATCCATGG

CAGAGCCATGCTGCTGGTGGGCCGTTTGATGGAAGAGACTGCCAACTTTGAAAGCAACGCTGTGATGAAGAAA

TATAAAGATGTAACAGCACTGTTGCCTGAATGGGAAGATGGCCATTTTTATCTTGCCAAGTACTATGACAAAC

TCATGCCAATGGTTACTGATAACAAGATGGAGAAGCAAGGAGACTTGATACGATATATAGTACTTCACTTTGG

AAGGTCTTTACAGTTCGGAAACCAATATATTTATCAATCGATGCCACGTATGCTTTCACTTTGGCTGGATTTT

GGAGCTAAAGTTTATGAATGGGAAAAAGCTGGTCGTGCTGACAGATTACAAATGAAAAATGAATTGATGAAAA

TAAATAAGGTCATATCTGACCATAAAAACCAGCTTGCTCCTTATCAGTTCCTTACAGCTTTCTCACAGCTAAT

CTCCAGAATATGTCACTCTCATGATGAGGTGTTTGCTGTGTTGATGGAAATTGTGGCTAAGGTGTTTGTGGCA

TACCCCCAGCAGGCAATGTGGATGATGACTGCTGTGTCTAAGTCATCATATCCAATGCGTGTAAACAGATGCA

AAGAGATACTCGAGAAGGCCATACATATGAAGCCATCCCTAGGAAAATTTATTGGAGATGCAACTCGCCTCAC

TGATAAACTACTAGAGCTCTGCAATAAGCCGGTGGATGGAAATACTAGCACCCTCAGTATGAATATCCACTTC

AAAATGCTGAAGAAACTAGTAGAAGAAACAACATTTAGTGAAATCCTTATTCCTCTACAGTCCGTGATGATTC

CCACCCTACCGTCTACTGCAGGGAAGCGTGACCATGCTGATCATGATCCATTCCCTGGCCACTGGGCTTACCT

CTCAGGCTTTGATGACGCGGTAGAGATTCTGCCTTCTCTCCAGAAACCAAAGAAAATTTCTCTAAAGGGATCA

GACGGTAAATCATACATTATGATGTGTAAACCAAAAGATGATCTTAGAAAGGACTGCCGGCTGATGGAATTTA

ACTCTTTAATCAACAAGTGTTTACGCAAAGATGCAGAATCACGAAGGAGAGAGCTTCATATTCGAACCTATGC

TGTCATTCCACTGAATGATGAATGTGGAATCATAGAGTGGGTGAATAATACTGCAGGATTCCGGAACATATTG

ATCAAGCTGTACAAGGAAAAAGGCATTTACATGGGTGGAAAGGAACTGCGGCAGTGTATGCTTCCCAAGAACG

CACCACTACAAGAAAAGCTGAAAGTCTTTAAGGAGGCCCTACTGCCTCGTCACCCCCCATTGTTCCATGAATG

GTTTTTAAGAACATTTCCTGATCCTACTTCTTGGTATAACAGCAGATCAGCCTATTGCCGTTCCACTGCTGTG

ATGTCTATGGTAGGTTACATACTGGGCCTAGGGGACCGCCATGGAGAAAACATTCTTTTTGACTCGCTTACTG

GGGAATGTGTCCATGTGGATTTTAACTGCCTCTTCAACAAGGGTGAAACATTTGAAGTTCCAGAGATCGTCCC

CTTCCGACTAACACATAACATGGTCAATGGTATGGGCCCCATGGGGACGGAGGGACTTTTTCGACGTGCATGT

GAGGTCATCATGAGGTTAATGAGAGAACAGAGGGAGTCACTTATGAGTGTGCTGAAACCCTTTTTACATGATC

CTTTGGTGGAATGGAGTAAACCAGCAAGAGGGAGTAGTAAAGGTCAAGTCAACGAGACAGGAGAAGTGATGAA

TGAAAAGGCCAAAACACATGTGCTTGACATAGAGCAGAGGCTACAAGGTGTGATTAAGACCAGGAATCGTGTA

AAGGGACTTCCGCTGTCCATTGAAGGACATGTCCATTACCTGATCCAAGAAGCCACAGATGAGAACCTTCTCA

GCCAGATGTACTTGGGGTGGGCTCCGTATATGTGATGCTGCTCATGTGGAACATCTCCCATTCTGTCAGAGAA

TAAGTACATTTGTAAATAACTGTAGGTGTATATTTGTATGAATACATTTATTATACAATTGCAGGACAAAAAA

ATGTCCAATAGGTAGTTTTATTTTGATGGAGGAGTCATGCATCTGTTTATATAAAACATTTTGTATACTATTT

TCTATTACCACCATTTATGTAGCCATTAATTGGTTTGGAATACTTTTTTGAAAAATAAATATTGTTATTTCTT

GTACGTTTAAAAAAAAAAAAAAAA
```

In certain embodiments, the ATR protein is about 80%, 85%, 90%, 95%, 97%, 99%, or nearly 100% identical to human or *Xenopus* ATR, and retains at least one of the following functions: (1) ability to be activated by TopBP1 from the same or the closest related species, (2) ability to bind TopBP1 and/or ATRIP from the same or the closest related species, (3) ability to phosphorylate one or more of the ATR kinase substrates, such as Chk1, MCM2, Rad1, Hus1, Rad17, Nbs1, Smc1, H2AX, PHAS-I, and/or a functional fragment thereof, (4) ability to at least partially rescue the phenotype of a cell/organism that is deficient for ATR, etc.

In certain embodiments, the ATR protein is encoded by a polynucleotide that is about 80%, 85%, 90%, 95%, 97%, 99%, or nearly 100% identical (or hybridize under high stringency condition as defined herein) to human or *Xenopus* ATR mRNA, and retains at least one of the following functions: (1) ability to be activated by TopBP1 from the same or the closest related species, (2) ability to bind TopBP1 and/or ATRIP from the same or the closest related species, (3) ability to phosphorylate one or more of the ATR kinase substrates, such as Chk1, MCM2, Rad1, Hus1, Rad17, Nbs1, Smc1, H2AX, PHAS-I, and/or a functional fragment thereof, (4) ability to at least partially rescue the phenotype of a cell/organism that is deficient for ATR, etc.

In certain embodiments, the TopBP1 protein is a human TopBP1. An exemplary human TopBP1 protein has the GenBank Accession No. AAI26210 (incorporated by reference), which sequence is listed below. Other human TopBP1 with polymorphism or other minor sequence variations are also within the scope of the invention.

```
MSRNDKEPFFVKFLKSSDNSKCFFKALESIKEFQSEEYLQIITEEEALKIKENDRSLYICDPFSGVVFDHLKK  (SEQ ID NO: 7)

LGCRIVGPQVVIFCMHHQRCVPRAEHPVYNMVMSDVTISCTSLEKEKREEVHKYVQMMGGRVYRDLNVSVTHL

IAGEVGSKKYLVAANLKKPILLPSWIKTLWEKSQEKKITRYTDINMEDFKCPIFLGCIICVTGLCGLDRKEVQ

QLTVKHGGQYMGQLKMNECTHLIVQEPKGQKYECAKRWNVHCVTTQWFFDSIEKGFCQDESIYKTEPRPEAKT

MPNSSTPTSQINTIDSRTLSDVSNISNINASCVSESICNSLNSKLEPTLENLENLDVSAFQAPEDLLDGCRIY

LCGFSGRKLDKLRRLINSGGGVRFNQLNEDVTHVIVGDYDDELKQFWNKSAHRPHVVGAKWLLECFSKGYMLS

EEPYIHANYQPVEIPVSHKPESKAALLKKKNSSFSKKDFAPSEKHEQADEDLLSQYENGSSTVVEAKTSEARP

FNDSTHAEPLNDSTHISLQEENQSSVSHCVPDVSTITEEGLFSQKSFLVLGFSNENESNIANIIKENAGKIMS

LLSRTVADYAVVPLLGCEVEATVGEVVTNTWLVTCIDYQTLFDPKSNPLFTPVPVMTGMTPLEDCVISFSQCA

GAEKESLTFLANLLGASVQEYFVRKSNAKKGMFASTHLILKERGGSKYEAAKKWNLPAVTIAWLLETARTGKR

ADESHFLIENSTKEERSLETEITNGINLNSDTAEHPGTRLQTHRKTVVTPLDMNRFQSKAFRAVVSQHARQVA

ASPAVGQPLQKEPSLHLDTPSKFLSKDKLFKPSFDVKDALAALETPGRPSQQKRKPSTPLSEVIVKNLQLALA

NSSRNAVALSASPQLKEAQSEKEEAPKPLHKVVVCVSKKLSKKQSELNGIAASLGADYRWSFDETVTHFIYQG

RPNDTNREYKSVKERGVHIVSEHWLLDCAQECKHLPESLYPHTYNPKMSLDISAVQDGRLCNSRLLSAVSSTK

DDEPDPLILEENDVDNMATNNKESAPSNGSGKNDSKGVLTQTLEMRENFQKQLQEIMSATSIVKPQGQRTSLS

RSGCNSASSTPDSTRSARSGRSRVLEALRQSRQTVPDVNTEPSQNEQIIWDDPTAREEPARLASNLQWPSCPT

QYSELQVDIQNLEDSPFQKPLHDSEIAKQAVCDPGNIRVTEAPKHPISEELETPIKDSHLIPTPQAPSIAFPL

ANPPVAPHPREKIITIEETHEELKKQYIFQLSSLNPQERIDYCHLIEKLGGLVIEKQCFDPTCTHIVVGHPLR

NEKYLASVAAGKWVLHRSYLEACRTAGHFVQEEDYEWGSSSILDVLTGINVQQRRLALAAMRWRKKIQQRQES

GIVEGAFSGWKVILHVDQSREAGFKRLLQSGGAKVLPGHSVPLFKEATHLFSDLNKLKPDDSGVNIAEAAAQN

VYCLRTEYIADYLMQESPPHVENYCLPEAISFIQNNKELGTGLSQKRKAPTEKNKIKRPRVH
```

A corresponding human TopBP1 mRNA sequence is represented in BC126209 (incorporated by reference):

CGAGGCTCCAACGAGTTCAGAAATGTCCAGAAATGACAAAGAACCGTTTTTGTGAAGTTTTTAAAGTCTTCA    (SEQ ID NO: 8)
GACAATTCCAAATGTTTTTTTAAAGCTCTCGAGTCCATAAAAGAATTCCAATCAGAAGAATATCTTCAGATTA
TTACAGAAGAAGAGGCATTGAAGATAAAGGAGAATGATAGATCACTTTATATCTGTGACCCTTTTAGTGGCGT
TGTCTTTGATCACCTCAAAAAGCTTGGCTGCAGAATTGTTGGTCCTCAAGTAGTCATATTTTGTATGCACCAC
CAGCGATGTGTCCCAAGAGCCGAACATCCAGTTTATAATATGGTTATGTCTGATGTAACCATATCTTGTACAA
GTCTGGAAAAGAAAAAGGGAAGAAGTTCATAAATATGTACAAATGATGGGCGGACGAGTATACAGAGACCT
TAATGTATCAGTAACTCACCTTATTGCAGGAGAAGTTGGTAGCAAAAAATATTTAGTTGCTGCAAACCTGAAG
AAACCTATTTTGCTTCCCTCTTGGATAAAAACACTTTGGGAGAAGTCACAAGAGAAAAAATAACTAGATATA
CTGATATAAACATGGAAGATTTCAAGTGTCCTATTTTTCTTGGTTGCATAATCTGTGTGACTGGCTTATGTGG
CTTAGACAGGAAAGAAGTTCAGCAACTCACAGTTAAGCATGGAGGTCAATACATGGGACAATTGAAAATGAAT
GAATGTACACACCTCATTGTGCAAGAACCAAAAGGTCAGAAGTATGAGTGTGCCAAGAGATGGAATGTACACT
GTGTGACCACACAGTGGTTTTTTGACAGTATTGAGAAAGGTTTTTGTCAGGATGAATCCATATACAAGACAGA
ACCTAGACCAGAAGCAAAGACTATGCCCAATTCTTCAACTCCTACCAGCCAGATCAACACAATTGATAGTCGT
ACTCTTTCAGATGTCAGCAATATTTCCAACATAAATGCAAGTTGCGTAAGTGAATCAATATGTAATTCACTTA
ACAGCAAACTGGAGCCTACACTTGAAAATCTAGAAAATCTGGATGTCAGTGCATTTCAAGCACCTGAAGATTT
ATTAGATGGTTGTCGGATATATCTTTGCGGTTTTAGTGGCAGAAAGCTAGATAAACTGAGAAGACTTATTAAC
AGTGGAGGTGGAGTTCGTTTTAACCAGCTAAATGAAGATGTAACTCATGTTATTGTGGGAGATTATGATGATG
AATTGAAGCAGTTTTGGAATAAATCAGCCCACAGGCCTCATGTAGTGGGAGCAAAGTGGTTGCTAGAGTGTTT
CAGTAAAGGTTATATGCTTTCTGAAGAACCATATATCCATGCTAATTACCAGCCAGTGGAAATTCCAGTTTCA
CATAAGCCTGAAAGTAAAGCAGCTCTTTTAAAAAAGAAGAACAGCAGCTTCTCTAAGAAAGACTTTGCTCCTA
GTGAAAAGCATGAGCAAGCTGATGAAGATCTGCTCTCTCAATATGAAAATGGTAGCTCCACAGTAGTTGAGGC
TAAGACGTCTGAAGCCAGGCCCTTTAATGATTCTACTCATGCTGAGCCCTTGAATGATTCTACTCACATTTCT
TTGCAAGAAGAAACCAGTCTTCTGTCAGTCATTGTGTCCCTGATGTTTCTACAATTACTGAAGAAGGCTTAT
TTAGCCAAAAGAGTTTCCTTGTTTTGGGTTTTAGTAATGAAAATGAATCTAACATCGCAAACATCATAAAAGA
AAATGCTGGGAAAATCATGTCCCTTCTGAGCAGAACTGTTGCGGATTATGCTGTGGTTCCTCTGCTGGGGTGT
GAAGTGGAAGCCACTGTGGGAGAAGTTGTTACAAATACATGGCTGGTTACTTGCATAGACTATCAGACTTTGT
TTGATCCAAAGTCGAATCCTCTCTTCACACCAGTTCCAGTAATGACAGGAATGACTCCTTTAGAGGATTGTGT
TATTTCATTTAGCCAGTGTGCTGGAGCAGAAAAAGAGTCTTTAACATTCCTAGCAAACCTCCTTGGAGCAAGT
GTTCAAGAATACTTTGTTCGCAAATCCAATGCAAAGAAAGGCATGTTTGCCAGTACTCATCTTATACTGAAAG
AACGTGGTGGCTCTAAATATGAAGCTGCAAAGAAGTGGAATTTACCTGCCGTTACTATAGCTTGGCTGTTGGA
GACTGCTAGAACGGGAAAGAGAGCAGACGAAAGCCATTTTCTGATTGAAAATTCAACTAAAGAAGAACGAAGT
TTGGAAACAGAAATAACAAATGGAATCAATCTAAATTCAGATACTGCAGAGCATCCTGGCACACGCCTGCAAA
CTCACAGAAAAACCGTCGTTACACCTTTAGATATGAACCGCTTTCAGAGTAAAGCTTTCCGTGCTGTGGTCTC
ACAACATGCCAGACAGGTCGCAGCCTCCCCAGCAGTAGGACAACCACTTCAGAAGGAGCCCTCGTTACACCTG
GATACACCATCAAAATTCCTGTCCAAGGACAAACTCTTCAAGCCTTCCTTTGATGTGAAGGATGCACTTGCAG
CCTTGGAAACTCCAGGACGTCCCAGCCAACAGAAAAGGAAACCGAGTACGCCACTCTCAGAAGTTATTGTCAA
AAACTTGCAACTTGCTTTGGCAAATAGCTCTCGAAATGCTGTCGCTCTTTCTGCCAGCCCTCAACTGAAAGAG
GCCCAGTCAGAAGGAAGAAGCCCCAAAGCCACTTCACAAAGTAGTGGTATGTGTTAGTAAAAAACTCAGTA
AGAAGCAGAGTGAACTAAATGGGATCGCAGCCTCTCTAGGAGCAGATTACAGGTGGAGTTTTGATGAAACAGT

```
GACTCATTTCATCTATCAAGGGCGGCCAAATGACACTAATCGGGAGTATAAATCTGTAAAAGAAAGAGGAGTA

CACATTGTTTCCGAGCACTGGCTTTTAGATTGTGCCCAAGAGTGTAAACATCTTCCTGAATCTCTTTATCCAC

ATACTTATAATCCCAAAATGAGCTTGGATATCAGCGCAGTGCAAGATGGCCGGCTCTGTAATAGTCGACTACT

CTCAGCTGTGTCTTCAACAAAGGATGATGAGCCAGATCCTTTGATTTTAGAAGAAAATGATGTAGACAATATG

GCCACCAATAATAAAGAGTCAGCACCATCAAATGGAAGTGGAAAGAATGACTCTAAAGGAGTTCTGACACAGA

CCTTAGAGATGAGAGAGAACTTTCAGAAGCAGTTACAGGAGATAATGTCTGCAACATCAATAGTGAAACCCCA

AGGGCAGAGGACTTCCCTTTCAAGAAGTGGTTGTAACAGCGCATCTTCAACCCCTGACAGCACTCGCTCTGCT

CGCAGTGGACGAAGTAGAGTCCTAGAGGCACTGAGGCAGTCTCGTCAGACAGTACCTGATGTCAACACAGAGC

CTTCCCAAAATGAACAGATCATTTGGGATGACCCTACAGCAAGGGAGGAGAGAGCAAGGCTTGCCAGCAATTT

GCAGTGGCCTAGTTGTCCCACACAATACTCTGAGCTTCAGGTTGACATTCAAAACTTGGAGGATTCTCCTTTT

CAAAAGCCTTTACATGATTCAGAAATTGCTAAACAGGCTGTCTGTGATCCTGGAAACATACGTGTGACTGAAG

CTCCCAAACACCCAATCTCTGAAGAACTGGAAACTCCCATAAAAGACAGCCACCTGATCCCTACGCCTCAAGC

CCCCAGTATTGCCTTTCCACTCGCCAACCCCCCTGTGGCTCCGCACCCTAGAGAAAAGATTATAACGATAGAG

GAGACTCATGAAGAATTAAAAAAACAGTACATATTTCAGTTATCATCTGAATCCTCAAGAACGTATTGACT

ATTGTCATCTGATTGAGAAACTAGGTGGATTGGTGATAGAAAAGCAGTGCTTTGATCCCACCTGTACACACAT

TGTTGTGGGACATCCACTTCGAAACGAGAAGTATTTAGCCTCAGTGGCAGCTGGGAAGTGGGTGCTTCATCGC

TCCTACCTTGAAGCCTGCAGGACTGCTGGACACTTCGTGCAGGAAGAAGACTATGAATGGGGAAGTAGTTCCA

TACTTGATGTTCTGACTGGAATCAATGTACAGCAACGAAGACTAGCACTTGCAGCAATGAGATGGAGAAAAAA

AATCCAGCAAAGACAAGAATCTGGCATTGTTGAGGGAGCATTTAGTGGGTGGAAGGTTATTTTACATGTGGAT

CAGTCTCGAGAAGCAGGCTTCAAACGCCTTCTTCAGTCAGGAGGAGCAAAGGTGCTACCTGGTCATTCTGTAC

CTTTATTTAAAGAGGCCACACATCTTTTTTCTGACTTGAATAAACTGAAACCAGATGACTCAGGAGTTAATAT

AGCAGAAGCTGCTGCCCAGAACGTGTACTGCTTGAGAACAGAATACATTGCTGATTATCTCATGCAGGAATCA

CCTCCTCATGTAGAAAATTACTGTCTACCAGAAGCTATTTCATTTATTCAGAATAATAAGGAACTTGGGACTG

GATTATCACAAAAGAGGAAAGCTCCTACAGAAAAAAATAAAATCAAACGACCTAGAGTACACTAATCGCATCT

ACCCTTTAGTTACCAAACATTAAATGTTTTTAAAAATTGAAAGCCTGAATGTGACTGTGATAGATTTGGGTAG

TAATTTAAAGATGAGTACCTGAAGAATTCTGCTTCAGAGTATAATGATGACCCTTCTTGAGTTTTGAACACCT

GAAATTGTAATCACTGAAATATTAACTGTTTCTTAATAAAAAGTTACCTGAAATAACAACAAATACAACTCC

TCAGCTAGCTTGCTGTTAAACCACATTGAAGTCTGTTAAAAGATATTTATTTTTCTTGTAAATATCTGAAGCT

GTAGCTTAGTGGAAATTTTAGCAAGGTAATGGATTTTGCTTTAAAATGTCTGCCTTACAAATTCATAACAACA

AGATTTGTCAGTCAGCATTTATTCATGTTTTCCCTGATTTTTATCTTCTCACCATTTTACCTCTTTTAACAGG

AGCCTGAGCACAAGGTTTAATGAGGAAGCTGGGGCTATAAATATGTGTGTATATATGTATATGTATGTTTGTA

CAAATCTCCATGATGTTTGCCAAGTTTGAATGCGCAAA
```

In certain embodiments, the TopBP1 protein is a *Xenopus* TopBP1. An exemplary *Xenopus* TopBP1 protein has the GenBank Accession ID of BAC65235 (incorporated by reference), which sequence is listed below. Other *Xenopus* ATR with polymorphism or other minor sequence variations are also within the scope of the invention.

```
MASSENEPFCVKFIKSPENSEYFFKAYEAIKQIQSDESLQLTEEREALLLKEKDKSLYICDPFSGAAFSHLKK   (SEQ ID NO: 9)

LGCRIVGPQVVIFCMENQRRVPPAEYPVYNMAMADVTISCTSLDKETREDVHHYVQIMGGCVYRDLNVSVTHL

IAGEVGSKKYLVAASLEKPILLPSWVKELWEKSNQRIIRYSDVNMTEYLCPIFRGCTICVTGLSSLDRKEVQR

LTALHGGEYTGQLKMNESTHLIVQEAKGQKYECARKWNVHCISVQWFFDSIEKGFCQDETMYKIEPASTIKSV

PDTSTPTGGNSKPNSRALYDVSQISNISTSCVNESAFNSAMASRLDPPADTLENLDISSLQAPDDLLDGCRIY
```

-continued

```
LCGFGGRKLDKLRKLINNGGGVRFNQLTGDVTHIIVGETDEELKQFLNKTQHRPYVLTVKWLLDSFAKGHLQP

EEIYFHSSYQQTEMPSPFEPAINLTANKMSSTRGPLNHTRNHQEDEDLLSQYTENNSTLIEDEHPKTSNTNSI

SQMSMHEDMTTCTSQSGLADTSTIIEGGLFSRKQFMVLGFLEEDEACIIDIIKKSAGKVLSSQKRAIADYAVV

PLLGCEVESTVGEVVTNAWLGMCIEQEKLLDPHSNALFTPVPFLEGSTPLRECVLSVSQFMGAERDSLVYLAG

LLGAKVQEFFVRKANPKKGMFASTHLVLKDAEGSKYEAAKKWNLPAVTMNWLLQCARTGRKADEDSYLVDNVP

EEDKDESFISQTYKPQAIRLSMHAPCHLENHPEALTKAAVTPLDMNRFKSKAFQSVISQHNKNPQTSGGESKV

LQREPSLHLDTPSKFLSKDKLFKPSFDVKDALAALETPGGPNQKNRTQSTPLSEVIGRNLQLAIANSTRQTAA

VTASPQLKAAEKKEFDNSKLLINVVICVSKKLIKKQGELNGIAASLGAEYRWCFDESVTHFIYHGRQNDMSRE

YKSVKERSGIYIVSEHWLFACSEQQKRVPEALYPHTYNPKMSLDISAVQDGSYTASKFSADTSLQQDENSELQ

LQQNNKFGETSDDQVKKAAGDGNPQNPSKDVKGALTQTLEMRENFQRQLQEFMSATSVVKPRGSVGRAGFDNS

PCTPEGARSTRNGRSRVLEALRQSRQAMTDLNTEPSQNEQIIWDDPTAREERAKLVSNLQWPDSPSQYSEQLQ

HNMNDAGGNYTPAKESLTDSEIAELEACEFEPKSAMRTPVIENNLQSPTKPDHLTPTPQAPSIAFPLANPPVA

PQPREKPVQPFSKEETLKERRFQLSSLDPQERIDYSQLIEELGGVVIEKQCFDPSCTHIVVGHPLRNEKYLAS

MAAGKWVLHRSYLEACRAAKRFIQEEDYEWGSISILSAVTNINPQQRMLAEAAMRWRKKLQGIKQNMGIAEGA

FSGWKVILNVDQTKEPGFKRLLQSGGAKVFAGHSSPLFKEASHLFADFSKLKPDEPRVNVAEAAAQGVNCLKP

EYIADYLMKELPPPMNNYCLPDAIPYVRVTGTGLSRKRKTSGDVSDVKRSRHY
```

A corresponding *Xenopus* TopBP1 mRNA sequence is represented in AB091779 (incorporated by reference):

```
CACCACGGGTCGTCATTTCCGTCAGTGGCCGGACACTGTAGGAAGCAATAGGAGATTTGGCGCGAATGACAAA    (SEQ ID NO: 10)

TTGGTCCCCCAGAAACCGGCTCCAGTTAAAATGGCTTCGAGTGAAAACGAGCCATTTTGTGTGAAATTTATCA

AGTCTCCTGAAAATTCTGAATACTTCTTCAAAGCTTATGAGGCAATCAAGCAAATTCAGTCTGATGAATCTCT

TCAGCTAACAGAAGAAAGAGAGGCACTTCTCTTAAAAGAAAAAGACAAATCTCTCTACATTTGTGATCCTTTC

AGTGGTGCTGCATTTAGCCATCTGAAAAAGCTTGGCTGTAGGATAGTTGGCCCACAAGTTGTCATCTTTTGCA

TGGAGAATCAAAGACGCGTTCCTCGTGCTGAATACCCTGTCTACAATATGGCAATGGCTGATGTGACAATATC

TTGCACCAGCCTCGATAAAGAAACTAGGGAAGATGTGCATCATTATGTACAAATCATGGGAGGCTGTGTGTAC

AGGGATCTTAATGTTTCTGTCACACACCTAATTGCTGGTGAAGTGGGCAGTAAAAAATACCTGGTGGCTGCAA

GTCTGGAGAAGCCCATTCTTCTTCCTTCTTGGGTGAAAGAATTATGGGAAAAATCAAATCAGAGGATTATTCG

ATACAGTGATGTAAACATGACAGAATATTTGTGCCCCATATTTCGTGGTTGTACTATATGTGTAACTGGATTA

AGCAGTTTAGACAGAAAGGAGGTGCAACGTCTTACAGCTCTGCATGGAGGAGAGTACACAGGGCAGCTTAAGA

TGAATGAATCAACACATCTTATTGTCCAAGAGGCTAAAGGCCAGAAATATGAGTGTGCCAGAAAGTGGAATGT

ACACTGTATCTCGGTTCAATGGTTCTTCGACAGTATTGAAAAAGGATTCTGTCAAGATGAAACAATGTATAAA

ATTGAGCCTGCTTCTACCATAAAATCTGTGCCAGATACATCCACTCCTACAGGTGGCAATAGCAAACCAAATA

GTCGGGCCCTTTATGATGTCAGCCAGATTTCCAATATAAGTACAAGCTGTGTTAACGAATCTGCTTTTAACTC

CGCAATGGCCAGCAGACTGGATCCTCCAGCAGATACCCTTGAAAACTTGGATATTAGTTCATTACAAGCTCCA

GATGACCTACTCGATGGCTGCCGGATATATCTGTGCGGGTTTGGGGGAAGAAAGTTGGACAAGCTAAGAAAGC

TAATCAACAATGGAGGGGGTGTGAGGTTTAATCAGCTTACAGGAGATGTAACCCACATTATTGTTGGAGAAAC

TGATGAAGAACTGAAGCAGTTTTTAAACAAAACACAACACAGACCTTATGTGTTAACTGTAAAATGGCTGCTG

GACAGCTTTGCAAAAGGACATCTGCAACCTGAGGAAATATATTTTCATTCAAGCTATCAACAAACTGAGATGC

CTTCACCATTTGAGCCTGCCATTAATTTAACTGCTAATAAGATGAGTAGTACACGAGGGCCTCTGAACCATAC

TCGCAACCATCAGGCAGATGAGGACCTGCTGTCTCAGTACACAGAAAATAACTCCACGTTAATTGAAGATGAG
```

-continued

```
CATCCTAAAACCTCTAATACCAACAGCATTTCCCAAATGAGCATGCATGAAGACATGACCCACTTGTACGAGCC
AAAGTGGTTTGGCCGATACATCCACTATAATTGAAGGAGGTTTATTCAGCCGAAAACAATTTATGGTGCTGGG
CTTTTTGGAAGAAGATGAGGCATGCATTATAGACATAATAAAGAAGAGCGCTGGCAAGGTGCTTTCATCTCAG
AAAAGAGCCATTGCTGATTATGCTGTAGTACCCTTACTGGGTTGTGAAGTGGAATCTACAGTTGGAGAGGTTG
TGACCAACGCTTGGCTGGGCATGTGTATAGAACAAGAGAAGCTATTAGACCCACATTCAAATGCTCTTTTTAC
ACCTGTGCCATTTTTGGAAGGTAGCACACCACTGCGGGAGTGTGTGCTTTCTGTCAGCCAATTTATGGGTGCT
GAAAGGGATTCATTAGTTTACTTGGCCGGTTTGCTTGGAGCAAAAGTACAAGAGTTTTTTGTGCGGAAAGCCA
ATCCAAAAAGGGCATGTTTGCCAGTACACACTTAGTACTTAAAGATGCTGAAGGGTCAAAATACGAAGCAGC
CAAAAAGTGGAATTTGCCAGCAGTGACAATGAACTGGCTATTGCAGTGTGCCAGAACTGGCAGAAAAGCAGAT
GAAGATTCTTACCTTGTTGATAATGTTCCTGAAGAAGATAAAGATGAAAGTTTCATAAGTCAGACATACAAAC
CCCAAGCAATCAGGCTATCAATGCATGCACCATGCCATCTAGAAAATCACCCGGAAGCCCTGACGAAAGCTGC
AGTTACCCCACTTGACATGAACCGGTTTAAGAGCAAAGCATTTCAGTCTGTTATTTCACAGCATAACAAGAAT
CCACAAACATCTGGTGGGGAAAGCAAAGTTCTTCAGAGAGAACCATCTTTGCATCTTGATACACCATCAAAAT
TTCTGTCCAAGGACAAACTTTTCAAACCCTCCTTTGATGTTAAGGATGCTCTTGCAGCTCTGGAAACACCTGG
AGGTCCTAACCAAAAAAACAGGACACAGAGCACTCCCTTGTCTGAAGTTATTGGTAGGAATCTGCAGCTGGCT
ATTGCGAACAGCACGCGTCAGACTGCTGCAGTTACTGCAAGCCCTCAGCTAAAGGCAGCAGAAAAGAAAGAGT
TTGACAACTCCAAGCTACTGATTAATGTCGTTATATGCGTGAGCAAGAAGCTAATTAAAAAACAAGGTGAACT
GAATGGCATTGCAGCCTCACTTGGAGCAGAATACAGATGGTGCTTCGATGAAAGTGTGACGCATTTTATCTAC
CACGGACGACAAAATGACATGAGCCGAGAATACAAATCTGTGAAAGAACGAAGTGGCATCTACATCGTTTCTG
AACACTGGCTATTCGCTTGTTCAGAACAGCAGAAGAGAGTACCCGAGGCTCTCTATCCCCATACATATAATCC
TAAAATGAGCTTGGATATCAGTGCTGTTCAAGATGGATCCTACACAGCCAGCAAATTCTCCGCAGACACCTCT
CTTCAGCAGGATGAGAATAGTGAATTACAGCTTCAGCAGAATAATAAATTTGGGGAGACTTCTGATGATCAGG
TTAAAAAAGCAGCTGGTGATGGAAACCCTCAAAACCCTTCAAAAGACGTTAAAGGAGCTCTAACTCAGACTTT
AGAGATGAGAGAAAATTTTCAGCGGCAGCTACAGGAGTTCATGTCTGCAACTTCAGTGGTAAAGCCTAGGGGC
TCTGTGGGTAGAGCTGGCTTTGATAATTCCCCTTGTACACCTGAAGGGGCACGTTCTACACGTAATGGAAGAA
GCAGAGTTTTGGAAGCACTAAGACAGTCCAGGCAGGCTATGACAGACCTCAATACAGAGCCATCGCAGAATGA
GCAAATCATTTGGGATGATCCCACTGCCAGAGAAGAAAGAGCAAAGCTGGTCAGCAATCTACAGTGGCCCGAC
AGTCCCTCCCAGTACTCTGAACAGCTTCAGCATAATATGAATGATGCTGGAGGAAATTATACACCAGCAAAGG
AATCTTTAACAGATTCTGAAATAGCAGAATTGGAAGCCTGTGAATTCGAGCCTAAATCAGCTATGAGAACTCC
TGTGATAGAGAATAATTTGCAGTCTCCAACCAAACCGGATCATCTCACCCCTACCCCACAAGCTCCGAGCATT
GCTTTTCCACTTGCCAACCCTCCAGTGGCACCACAACCTAGAGAAAAGCCTGTGCAACCATTTTCAAAGGAGG
AAACTTTAAAGGAGCGTCGATTCCAGCTATCTTCATTAGACCCTCAAGAACGAATTGATTACTCACAGCTTAT
TGAGGAACTAGGGGGAGTGGTGATAGAAAAGCAATGTTTTGATCCAAGCTGCACACACATCGTTGTGGGTCAT
CCTCTTCGTAATGAAAAATATTTGGCCTCAATGGCTGCAGGAAAGTGGGTACTGCACAGGTCATATCTGGAAG
CCTGCAGAGCTGCAAAACGATTCATACAGGAGGAGGACTATGAATGGGAAGCATATCCATACTGAGTGCTGT
GACCAACATAAATCCACAGCAAAGGATGCTGGCAGAGGCTGCAATGAGATGGAGGAAGAAGCTGCAAGGAATA
AAGCAAAATATGGGTATCGCCGAGGGTGCATTCAGTGGCTGGAAAGTAATTTTAAATGTCGACCAAACAAAGG
AACCTGGTTTCAAACGTCTGCTCCAGTCAGGAGGTGCAAAGGTATTTGCTGGCCATTCTTCTCCTCTGTTTAA
AGAAGCAAGCCACCTCTTTGCTGACTTCAGCAAACTGAAACCCGATGAGCCCAGAGTAAATGTGGCAGAGGCT
GCAGCACAAGGAGTAAACTGCCTGAAACCAGAGTATATTGCCGACTACCTCATGAAGGAGCTACCTCCGCCCA
```

```
-continued
TGAACAATTACTGCCTCCCAGATGCAATTCCATATGTCCGGGTTACAGGGACTGGGCTTTCGCGCAAAAGGAA

AACCTCTGGAGACGTCTCTGATGTTAAGAGATCACGGCATTACTGAGAGAGTGAGATTGAAGAGCTAGAGAAA

AAGGCAGCAGCTTGGTAATGCCAACTATGTAGCACTACTCTTTGTGACAAAATGTTATGTACTCTGTCATGTC

TGTTAATTTATATGGAAATCGGTTTTTTCATGTCAAATACTATGTAGATATGTACACAAATAACATTCCCTGT

ATTTTATATACTTCTATGTGTCCGTGCCCCAATATATGTGAAATACGTTTCATACCCTCCCTGTTCATTGGGT

GCAGTTACCGCCCAGTTATTTGTACACTTGTATAATAGGCAACCTTTTTTACTCATACTATTGTCATTCCCTT

ATTGCTCCTGTCCAACTAACAGTGGATAGGCAATATTGAATGAAATGTTATTTTCTTTTTTCTTTTAATAGTA

CTGTTTTTGAGTATATGTTAAAATATAATAAATCTAAACAC
```

In certain embodiments, the TopBP1 protein is about 80%, 85%, 90%, 95%, 97%, 99%, or nearly 100% identical to human or *Xenopus* TopBP1, and retains at least one of the following functions: (1) ability to activate the ATR kinase from the same or the closest related species, (2) ability to bind ATR and/or ATR-ATRIP complex from the same or the closest related species, (3) ability to at least partially rescue the phenotype of a cell/organism that is deficient for TopBP1.

In certain embodiments, the TopBP1 protein is encoded by a polynucleotide that is about 80%, 85%, 90%, 95%, 97%, 99%, or nearly 100% identical (or hybridize under high stringency condition as defined herein) to human or *Xenopus* TopBP1 mRNA (supra), and retains at least one of the following functions: (1) ability to activate the ATR kinase from the same or the closest related species, (2) ability to bind ATR and/or ATR-ATRIP complex from the same or the closest related species, (3) ability to at least partially rescue the phenotype of a cell/organism that is deficient for TopBP1, etc.

Another aspect of the invention relates to a method to screen for a modulator of ATR activation by TopBP1, the method comprising: (1) providing a mixture comprising TopBP1 and ATR; (2) contacting the mixture with a candidate compound; (3) determining the binding of TopBP1 to ATR, and/or the activation of the kinase activity of ATR; wherein a statistically significant change either in the binding of TopBP1 to ATR or the activation of the kinase activity of ATR or both in the presence of the test compound compared to those in the absence of the test compound is indicative that the test compound is a modulator of TopBP1 activation of ATR.

According to the method of the invention, the screening assay may be carried out in vitro or in vivo. For example, in a typical in vitro assay, a reaction mixture comprising TopBP1 and ATR, optionally ATRIP, may be incubated at an appropriate temperature, in the presence of an ATR substrate (such as one or more of those disclosed herein). The level of substrate phosphorylation by ATR may be recorded as a baseline phosphorylation (in the absence of any test compounds). This reaction setting may then be repeated in the presence of one or more test compounds, and the level of substrate phosphorylation by ATR may be compared to the baseline level, wherein an increase in phosphorylation is indicative that the test compound is an activator of TopBP1-mediated ATR activation, and wherein a decrease in phosphorylation is indicative that the test compound is an inhibitor of TopBP1-mediated ATR activation.

Similarly, the assay may also be carried out to measure the level of binding between TopBP1 with ATR or ATR-ATRIP complex. In this embodiment, either the TopBP1 or the ATR may be immobilized on a solid support, such as a 96-well plate coated by ATR or TopBP1 (for example, by binding to an antibody against ATR or TopBP1). The binding of TopBP1 or ATR to the immobilized binding partner, in the presence or absence of a candidate compound may be measured and compared. An increase in binding is indicative that the test compound is an activator of TopBP1-mediated ATR activation, and a decrease in binding is indicative that the test compound is an inhibitor of TopBP1-mediated ATR activation.

In an in vivo assay, a cell having TopBP1 and ATR may be contacted by a test compound, and the level of substrate phosphorylation by ATR, or the level of TopBP1 binding to ATR may be measured by, e.g., immunoprecipitation—Western blot.

In certain embodiments, the method further comprises determining the extent of ATR activity change by the test compound in the absence of TopBP1 in the mixture. This ensures that the effect of the test compound, if any, on ATR activation is TopBP1-mediated (such as a modulator that affects TopBP1-ATR binding), rather than TopBP1-independent (such as ATR kinase inhibitors).

The screening method of the invention may be used to screen for activators of TopBP1-mediated ATR activation, or inhibitors of TopBP1-mediated ATR activation, or both.

In certain embodiments, the mixture contains a complex of TopBP1 and ATR. Optionally, the complex further contains ATRIP.

In certain embodiments, the kinase activity of ATR is determined by the degree of phosphorylation of one or more substrates by ATR.

In certain embodiments, the degree of phosphorylation is measured by immunoassay and/or Western blot.

In certain embodiments, the one or more substrates include Chk1, MCM2, Rad1, Hus1, Rad17, Nbs1, Smc1, H2AX, PHAS-I, and/or a functional fragment thereof.

In certain embodiments, TopBP1 is a full length protein, or a functional fragment comprising amino acid sequences between the sixth and seventh BRCT domains of TopBP1 (e.g., the ATR activation domain of TopBP1).

In certain embodiments, ATR is a full length protein, or a fragment comprising a functional kinase domain.

In certain embodiments, TopBP1 and/or ATR is from human or *Xenopus*.

In certain embodiments, TopBP1 and ATR are from the same species, or closely related species. In other embodiments, they are from different species.

In certain embodiments, the invention contemplates that the present methods may be used to identify combinations of agents (e.g., two or more agents) which can modulate the activation of at least one ATR activity by TopBP1. Such modulators may act additively or synergistically. In one embodiment, neither modulator alone is effective, however, the modulators together modulate the activation of at least one ATR activity by TopBP1. In another embodiment, each modulator alone has some effect on ATR activation by TopBP1, and the modulators together act synergistically or additively.

The agents may all modulate TopBP1-mediated ATR activation. Alternatively, at least one agent may modulate ATR activity or TopBP1 activity directly to provide a sensitized assay background.

Any compound or library of compounds may be used for the screening assay of the invention.

In any embodiment of the invention, if a library of candidate compounds are used, the library may comprise synthetic compounds, natural compounds, or a mixture thereof.

In certain embodiments in which two or more compounds are used, the mixture/cell may be contacted with a "cocktail" or pool of the compound, by the compounds separately, or both. Where the mixture/cell is contacted with the two or more compounds separately, the contacting can be simultaneous or sequential. Where the contacting is sequential, the mixture/cell may be pre-treated by a first test compound or compounds, followed by a second batch of one or more other compounds. Optionally, the first batch of compounds are first removed (e.g., by washing away with buffers) before the second batch of compounds are added.

In any embodiment of the invention, at least one compound in the library is tested at two or more different concentrations. This may be beneficial because the same compound may have different effective ranges of concentrations against different cell types or against the same cell type under different conditions. In certain embodiments, the two or more different concentrations spans at least about 2, 3, 4, 5, 6, 7, 8, 9, 10 or more orders of magnitude in terms of test compound concentration. In the initial experiments, a wider range of concentrations (such as 3-5 concentrations over 10 orders of magnitude) may be used, while in further experiments, more data points might be spread over a smaller concentration range. In certain embodiments, the medium concentration tested is the concentration closest to known effective concentration in human for the compound or structurally similar compounds. Those of skill in the art are familiar with selecting concentrations that are useful in the methods of the invention.

In any embodiment of the invention, the candidate compounds may be from a polypeptide library, an antibody library, a small molecule library, a polynucleotide library, or a mixture thereof. "Small molecule" as used herein includes molecules with a molecular weigh of no more than 50 Da, 100 Da, 200 Da, 500 Da, 1 kDa, 2 kDa, or 5 kDa. "Polynucleotide library" may include antisense oligonucleotides, an siRNA library, a cDNA library, a genomic DNA library, etc.

In certain embodiments, the screening assay is carried out in high throughput. In these high throughput embodiments of the invention, any format may be used, as long as it is scalable and suitable for high throughput screening/detection system. By way of illustration, the high throughput format may comprise plates or other containers with any number of wells, such as six-well, 12-well, 24-well, 48-well, 96-well, 384-well, or 1536-well, etc. As a skilled artisan will appreciate, the choice of format will depend on the specific assays (e.g., certain assays may preferably be carried out in larger wells or smaller wells).

A modulator identified by the subject methods has many potential uses. Such a modulator may be a nucleic acid, peptide, polypeptide, RNAi construct, chemical compound, small organic molecule, antisense RNA, antibody, or the like. Furthermore, such a modulator may either increase or decrease the activation of ATR by TopBP1. An exemplary activity of an ATR polypeptide which is modulated (either increased or decreased) by TopBP1 includes the phosphorylation of a Chk1 protein by ATR. Additional preferred activities which may be modulated (either increased or decreased) include (1) the ability to bind single-stranded DNA, (2) the ability to bind double-stranded DNA, (3) the ability to induce cell cycle delay in response to DNA damage, and/or (4) the ability to induce cell cycle delay in response to a DNA replication block.

Modulators identified by the methods of the present invention may be useful in a therapeutic context. For example, normal function of ATR, and other ATR related proteins (such as ATM), is required to maintain proper genomic stability. Conditions of unregulated cell proliferation, including various forms of cancer, may result from failure of proper cell cycle arrest in response to DNA damage. Accordingly, modulators which modulate the activation of ATR by TopBP1 have significant utility in the treatment of diseases associated with unregulated cell proliferation including all forms of cancer. The invention contemplates that such agents may be used alone, or may be administered as part of a therapeutic regimen in combination with other agents such as traditional chemotherapeutics, radiation therapy, holistic medicine, and the like.

However, cell cycle checkpoints can also represent an impediment to the treatment of many proliferative disorders including cancer. For example, one of the goals of treating cancerous tissue with damaging agents such as chemotherapeutics and radiation is to induce the cells to die. However, the induction of cell cycle checkpoints in response to the damaging agents sometimes lessens the effectiveness of the treatment. Accordingly, the present invention further contemplates the therapeutic use of agents which decrease an ATR activity by, for example, using an inhibitor if ATR activation by TopBP1 to inhibit the TopBP1-mediated ATR activation.

Thus in one aspect, the invention provides a method for treating cancer, comprising administering to a patient in need thereof an effective amount of a therapeutic composition comprising an inhibitor of ATR activation by TopBP1.

In certain embodiments, the inhibitor is an inhibitor of TopBP1 activity.

In certain embodiments, the method further comprises administering an inhibitor of ATR activity.

In certain embodiments, the method further comprises administering a treatment and/or an agent that damages DNA and/or inhibits DNA replication. For example, the treatment may be surgery or ionizing radiation. The agent may be any of many anti-cancer drugs or chemotherapeutic agents.

In certain embodiments, suitable anti-cancer drugs: methotrexate, busulfan, thioguanine, 6-mercaptopurine, nitrogen mustard, guanazole, R-methylformamide, actinomycin D, chlorambucil, thiadiazole, thio-tepa, DON, melphalan, borterzomib, dexamethasone, triethylenemelamine, hexamethylenemelanime, gallium nitrate, 5-fluorouracil, thymidine, delta-1-testololactone, mitramycin, pipobroman, cyclophosphamide, mitomycin C, 5-FUDR, hydroxyurea, methyl-GAG, uracil nitrogen mustard, O6-methylguanine, o,p'-DDD, DTIC, vinblastine sulfate, IMPY, porfiromycin, chromomycin, cytosine arabinoside, vincristine sulfate, thalicarpine, B-TGDR, A-TGDR, fluorodopan, D-tetrandrine, procarbazine, CCNU, daunorubicin (daunomycin), S-trityl-L-cysteine, streptozoticin, methyl-CCNU, PCNU, hexamethylenebisacetamide, 3HP, Yoshi-864, 5-azacytidine, cytembena, 5HP, L-asparaginase, iphosphamide, pentamethylmelamine, diglycoaldehyde, cisplatin, VM-26 (teniposide), doxorubicin (Adriamycin), bleomycin, paclitaxel (Taxol), dichloroallyl lawsone, 3-deazauridine, 5-azadeoxycytidine, triazinate, ICRF-159, dianhydrogalatitol, indicine N-oxide, rifamycin SV, piperazinedione, soluble Baker's Antifol, emofolin sodium, anguidine, VP-16 (etoposide), homoharringtonine, hycanthone, pyrazofurin, cyclocytidine, ftorafur, hydrazine sulfate, L-alanosine, maytansine, neocarzinostatin, AT-125 (acivicin), rubidazone, bruceantin, asaley, ICRF-187, spirohydantoin mustard, chlorozotocin, tamoxifen, AZQ, spirogermanium, aclacinomycin A, 2'-deoxycoformycin, PALA, rapamycin, largomycin, CBDCA (carboplatin), m-AMSA (amsacrine), caracemide, CHIP, 3-deazaguanine, dihydro-5-azacytidine, glycoxalic acid, deoxydoxorubicin, N,N-dibenzyldaunomycin, menogaril, (carboxyphthalato) platinum, pyrrolizine dicarbamate, triciribine phosphate, ARA AC, trimethyltrimethylolmelamine, mitindomide, 8Cl-cyc-AMP, tiazofurin, pyrimidine-5-glycodialdehyde, flavoneacetic acid ester, teroxirone, DHAD (mitoxantrone), aphidicolin glycinate, L-cysteine analogue, acodazole hydrochloride, amonafide, fludarabine phosphate, SR2555 (nitroimidazole), batracylin, nitroestrone, pibenzimol hydrochloride, bactobolin, didemnin B, L-buthionine sulfoximine, phyllanthoside, hepsulfam, macbecin II, rhizoxin, tetrocarcin A sodium salt, merbarone, bisantrene hydrochloride, penclomedine, clomesone, chloroquinoxaline sulfonamide, bryostatin, fostriecin, dihydrolenperone, piperazine alkylator, flavoneacetic acid, cyclodisone, pancratiastatin, oxanthrazole, 4-ipomeanol, trimetrexate, mitozolamide, morpholino-ADR, anthrapyrazole, deoxyspergualin, cyanomorpholino-ADR, pyrazine diazohydroxide, tetraplatin, pyrazoloacridine, bispyridocarbazolium DMS, DUP785 (brequinar), cyclopentenylcytosine, ARA-6-MP, BCNU, echinomycin, carmethizole, topotecan, and MX2HCl.

In certain embodiments, the agent induces DNA damage or inhibits DNA replication, such as in fast growing cells. For example, camptothecin treatment induces replication stress and replication-associated double-strand breaks. In combination with any of the subject inhibitor of TopBP1 activity, the combined therapy may synergistically kill cancer cells while doing the least amount of damage to normal cells.

In certain embodiments where it is desired to test various treatment regimens comprising multiple therapeutic agents or modalities, treatment using the modulator of the invention may be combined with any of the non-compound-based treatments (such as those described herein), with the treatments occurring in any desired order or simultaneously.

Yet another aspect of the invention provides an ATR activator comprising a polypeptide about 80%, 85%, 90%, 95%, 97%, 99%, or nearly 100% identical to the ATR activation domain of TopBP1, said ATR activator activates the kinase activity of ATR.

As used herein, the "ATR activation domain of TopBP1" refers to the conserved region between the 6th and 7th BRCT domains of the TopBP1 protein, which retains all or substantially all of the ATR activation function of the full length TopBP1 protein. The ATR activation by TopBP1 may be assayed by a kinase assay using one of the ATR substrate polypeptides, such as those disclosed herein. The minimally active ATR activation domain of TopBP1 may retain 100% or nearly 100% of the full-length TopBP1 activity (in terms of ATR activation), yet has no sequence overlap or substantially no sequence overlap with any of the BRCT domains of TopBP1. Exemplary ATR activation domains of TopBP1 includes residues 972-1279 of the Xenopus TopBP1 (XtopBP1) protein, and residues 978-1192 of the human TopBP1 protein.

In certain embodiments, the ATR activation domain of TopBP1 comprises residues 1050-1192 of human TopBP1, or residues 978-1192 of human TopBP1, or residues 972-1279 of human TopBP1, or residues 1008-1286 of human TopBP1, or residues 1050-1286 of human TopBP1.

In certain embodiments, the ATR activation domain of TopBP1 comprises TopBP1 fragments corresponding to the above human TopBP1 fragment from other non-human species, such as from *Xenopus*, non-human mammals, non-human primates, etc. Sequence alignments using art-recognized methods, such as using the SeqMan program from the DNASTAR package of software (DNASTAR, Inc., Madison, Wis.), would readily identify the corresponding sequences in the other TopBP1 sequences.

In a related aspect, the invention provides a polynucleotide encoding a subject ATR activator.

In certain embodiments, the polynucleotide is a cDNA.

In certain embodiments, the polynucleotide is a vector capable of self-replicating in a host cell. The vector may be a plasmid, a phagemid, a viral vector (AAV vector, lentiviral vector, adnoviral vector, etc.), a BAC, a PAC, a YAC, or any other art-recognized vectors.

Certain details of the invention are further described below in the non-limiting exemplary embodiments.

(ii) Definitions

For convenience, certain terms employed in the specification, examples, and appended claims are collected here.

As used herein, "protein" is any polymer consisting essentially of any of the 20 amino acids. Although "polypeptide" is often used in reference to relatively large polypeptides, and "peptide" is often used in reference to small polypeptides, usage of these terms in the art overlaps and is varied. Thus the terms "peptide(s)," "protein(s)" and "polypeptide(s)" are used interchangeably herein. The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence of an exon of a protein, or a portion thereof, or protein sequence, or portion thereof, respectively, as it normally exists in vivo.

The term "mutant" refers to any change in the genetic material of an organism, in particular any change (e.g., deletion, substitution, addition, or alteration) in a wild type polynucleotide sequence or any change in a wild type protein. The term "mutein" is used interchangeably with "mutant."

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "transfection" means the introduction of a nucleic acid, e.g., an expression vector, into a recipient cell by nucleic acid-mediated gene transfer. "Transformation," as used herein, refers to a process in which a cell's genotype is changed as a result of the cellular uptake of exogenous DNA or RNA, and, for example, the transformed cell expresses a recombinant form of a polypeptide or, where anti-sense expression occurs from the transferred gene, the expression of a naturally-occurring form of a protein is disrupted.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors." In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of the protein.

As used herein, the term "tissue-specific promoter" means a DNA sequence that serves as a promoter that regulates expression of a selected DNA sequence operably linked to the promoter, and which effects expression of the selected DNA sequence in specific cells of a tissue, such as cells of neural origin, e.g. neuronal cells. The term also covers so-called "leaky" promoters, which regulate expression of a selected DNA primarily in one tissue, but cause expression in other tissues as well.

"Homology" and "identity" are used synonymously throughout and refer to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding one of the subject polypeptides with a second amino acid sequence defining a domain (e.g. polypeptide portion) foreign to and not substantially homologous with any domain of one of the subject polypeptides. A chimeric protein may present a foreign domain which is found (albeit in a different protein) in an organism which also expresses the first protein, or it may be an "interspecies," "intergenic," etc. fusion of protein structures expressed by different kinds of organisms.

As used herein, a "transgenic animal" is any animal, preferably a non-human mammal, bird, fish or amphibian, in which one or more of the cells of the animal contain heterologous nucleic acid introduced by way of human intervention, such as by trangenic techniques well known in the art. The nucleic acid is introduced into the cell, directly or indirectly, by way of deliberate genetic manipulation, such as by microinjection, by infection with a recombinant virus, by transposition, or other methods well known in the art. The term genetic manipulation does not include classical cross-breeding, or in vitro fertilization, but rather is directed to the introduction of a recombinant DNA molecule. This molecule may be integrated within a chromosome, or it may be extra-chromosomally replicating DNA.

As used herein, the term "transgene" means a nucleic acid sequence which is partly or entirely heterologous or foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, such as introns, that may be necessary for optimal expression of a selected nucleic acid.

The "non-human animals" of the invention include vertebrates such as rodents, non-human primates, sheep, cats, dogs, cows, pigs, rabbits, avians, amphibians, fish, reptiles, etc. The term "non-mammalian animals" include avians, amphibians, fish, reptiles, etc. Preferred non-mammalian animals are selected from amphibians and fish. Exemplary fish include, without limitation, zebrafish. Exemplary amphibians include, without limitation, frogs, newts and toads (e.g., *Xenopus laevis, Xenopus tropicalis, Rana pipiens, Rana catesbeiana, Rana temporaria, Rana sylvatica*, and *Bufo bufo*).

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding an ATR polypeptide preferably includes no more than 10 kilobases (kb) of nucleic acid sequence which naturally immediately flanks the ATR gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state.

As used herein, "proliferating" and "proliferation" refer to cells undergoing mitosis.

The term "agent" refers to any compound screened by the methods of the present invention. Agents which may be screened by the subject methods include nucleic acids, peptides, proteins, small organic molecules, chemical compounds, ribozymes, RNAi constructs, antisense RNAs, and antibodies. Agents screened by the subject methods can be administered individually, or can be administered in combination with one or more other agents. The invention further contemplates the screening of libraries of agents. Such libraries may include, without limitation, cDNA libraries (either plasmid based or phage based), expression libraries, combinatorial libraries, chemical libraries, phage display libraries, variegated libraries, and biased libraries.

The term "library" refers to any collection of nucleic acids, proteins, peptides, chemical compounds, small organic molecules, or antibodies. Libraries comprising each of these are well known in the art. Exemplary types of libraries include combinatorial, variegated, biased, and unbiased libraries. Libraries can provide a systematic way to screen large numbers of nucleic acids, proteins, peptides, chemical compounds, small organic molecules, or antibodies. Often, libraries are sub-divided into pools containing some fraction of the total species represented in the entire library. These pools can then be screened to identify fractions containing the desired activity. The pools can be further subdivided, and this process can be repeated until either (i) the desired activity can be correlated with a specific species contained within the library, or (ii) the desired activity is lost during further subdivision of the pool of species, and thus is the result of multiple species contained within the library.

"Chk1" as used herein, refers to the amino acid or nucleic acid sequences of Chk1 obtained from any species. Exemplary species include mammals such as cows, pigs, rabbits, mice, rats, dogs, cats, horses, goats, sheep, non-human primates, and humans. Further exemplary species include amphibians, reptiles, and fish. Nucleic acid and amino acid sequences of Chk1 are represented, for example, in GenBank Accession Nos: AF117816, AB019218, AF053120, AF032875, AF016583, and NM_001274.

As used herein, "ATR" or "Ataxia-Telangiectasia and RAD3-Related" (also known as "FRAP-Related Protein 1" or "FRP1") refers to a member of the phosphatidylinositol kinase-related kinase (PIKK) family proteins, which are high molecular mass kinases involved in cell cycle progression, DNA recombination, and the detection of DNA damage (Cimprich et al., *Proc. Nat. Acad. Sci.* 93: 2850-2855, 1996). Human ATR or FRP1 contained 2,644 amino acids and a predicted molecular mass of 301 kD, and is most closely related to 3 of the family members involved in checkpoint function—Mei-41 (Drosophila), Mec1 (*S. cerevisiae*), and Rad3 (*Schizosaccharomyces*). The protein sequence of the human ATR is described in, for example, NCBI RefSeq NP_001175, and the corresponding cDNA sequence is described in, for example, NM_001184.2. The *Xenopus laevis* ATR protein sequence is described in, for example, GenBank Accession No. Q9DE14 or AAW78662 (sequences incorporated herein by reference).

In certain embodiments, "polypeptides having ATR activity" or "bioactive ATR polypeptides" may also be used in the instant invention. In general, polypeptides referred to herein as having an activity of an ATR polypeptide (e.g., are "bioactive") are defined as polypeptides which include an amino acid sequence corresponding (e.g., at least 80%, 85%, 90%, 95%, 98%, 100% identical) to all or a portion of the amino acid sequences of the human or *Xenopus* ATR polypeptide, and which have all or a portion of the biological/biochemical activities of a naturally occurring ATR protein. Examples of such biological activity includes the ability to phosphorylate Chk1 proteins or other substrates of ATR, the ability to bind single stranded DNA, the ability to bind double stranded DNA, the ability to induce cell cycle delay in response to DNA damage, and/or the ability to induce cell cycle delay in response to a DNA replication block. The bioactivity of certain embodiments of the subject ATR polypeptides can be characterized in terms of an ability to induce cell cycle delay in response to DNA damage and/or a DNA replication block.

"ATRIP" or "ATR-Interacting Protein" is phosphorylated by ATR, regulates ATR expression, and is an essential component of the DNA damage checkpoint pathway. ATRIP is also known as "3-Prime Repair Exonuclease 1" (or "Trex1" in human, Rad26 in *S. pombe*, and Mus304 in *Drosophila melanogaster*). It contains 3' to 5' exonuclease activity, and removes mismatched, modified, fragmented, and normal nucleotides to generate the appropriate 3'-termini for subsequent steps in the DNA metabolic pathways. There proteins are all referred-to herein as ATRIP.

ATRIP and ATR are mutually dependent partners in cell cycle checkpoint signaling pathways. They both localize to intranuclear foci after DNA damage or inhibition of replication. Deletion of ATR mediated by the Cre recombinase caused the loss of ATR and ATRIP expression, loss of DNA damage checkpoint responses, and cell death. Therefore, Cortez et al. (*Science* 294: 1713-1716, 2001) concluded that ATR is essential for the viability of human somatic cells.

This ATRIP gene uses two different open reading frames (ORFs). The upstream ORF encodes proteins which interact with ATR. The proteins encoded by this upstream ORF localize to intranuclear foci following DNA damage and are essential components of the DNA damage checkpoint. The downstream ORF encodes proteins with 3' exonuclease activity. Other enzymes with this activity are involved in DNA replication, repair, and recombination. Similarity to an *E. coli* protein suggests that the enzymes encoded by this ORF may be a subunit of DNA polymerase III, which does not have intrinsic exonuclease activity. Both ORFs are subject to alternative splicing, resulting in six transcript variants, all of which are within the meaning of ATRIP as used herein.

The protein sequence of the several human ATRIP isoforms are described in, for example, NCBI RefSeq NP_057465 (isoform a), NP_338597, NP_338598 & NP_338599 (isoform b), NP_115542 (isoform c), NP_569055 (isoform d), etc. The *Xenopus laevis* ATRIP protein sequence is described in, for example, GenBank Accession No. AAQ82669, AAT70231, or AAH97710 (all sequences incorporated herein by reference).

"TopBP1" or "DNA Topoisomerase II-Binding Protein 1" is a 1,522-amino acid protein sharing about 24% identity over 236 amino acids with *S. pombe* Rad4. TopBP1 contains 8 repeating regions throughout its sequence that share similarity with similar repeat regions in the fission yeast Rad4/Cut5 protein, the budding yeast DPB11 protein, and the *Drosophila melanogaster* Mus101 protein (i.e., BRCT domains I-VIII of TopBP1. "BRCT" stands for "BRCA1 Carboxyl-Terminal." This domain is present in a number of proteins involved in DNA repair and/or DNA damage-signaling pathways). TopBP1 also has an auto-ADP-ribosylation site and 2 C-terminal nuclear localization signals. TopBP1 interacts with the C-terminal region of topoisomerase II beta. This interaction suggests a supportive role for this protein in the catalytic reactions of topoisomerase II beta through transient breakages of DNA strands.

The protein sequence of the human TopBP1 protein is described in, for example, NCBI RefSeq NP_008958. The *Xenopus laevis* TopBP1 protein sequence is described in, for example, GenBank Accession No. BAC65235 (all sequences incorporated herein by reference).

(iii) Exemplary TopBP1 Modulators

The invention provides numerous modulators that are capable of modulating (e.g., inhibiting or activating) ATR activation by TopBP1. In certain embodiments, the modulators may affect (e.g., increase or decrease) the transcription and/or expression of TopBP1. In other embodiments, the modulators may affect (e.g., increase or decrease) the binding of TopBP1 to the ATR-ATRIP complex. In yet other embodiments, the modulators may affect (e.g., increase or decrease) the activation of the ATR kinase activity by TopBP1. Certain modulators may affect any one or more of: the transcription and/or expression of TopBP1, the binding of TopBP1 to the ATR-ATRIP complex, and the activation of the ATR kinase activity by TopBP1.

Several non-limiting exemplary modulators are described for illustration purpose only.

Inhibitors of ATR Activation by TopBP1

RNAi

In certain embodiments, RNAi may be used to knock down the expression of TopBP1 or any component gene necessary for TopBP1-mediated ATR activation.

RNAi is a process of sequence-specific post-transcriptional gene repression which can occur in eukaryotic cells. In general, this process involves degradation of an mRNA of a particular sequence induced by double-stranded RNA (dsRNA) that is homologous to that sequence. For example, the expression of a long dsRNA corresponding to the sequence of a particular single-stranded mRNA (ss mRNA) will labilize that message, thereby "interfering" with expression of the corresponding gene. Accordingly, any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length. Accordingly, RNAi may be effected by introduction or expression of relatively short homologous dsRNAs. Indeed, the use of relatively short homologous dsRNAs may have certain advantages as discussed below.

Mammalian cells have at least two pathways that are affected by double-stranded RNA (dsRNA). In the RNAi (sequence-specific) pathway, the initiating dsRNA is first broken into short interfering (si) RNAs, as described above. The siRNAs have sense and antisense strands of about 21 nucleotides that form approximately 19 nucleotide si RNAs with overhangs of two nucleotides at each 3' end. Short interfering RNAs are thought to provide the sequence information that allows a specific messenger RNA to be targeted for degradation. In contrast, the nonspecific pathway is triggered by dsRNA of any sequence, as long as it is at least about 30 base pairs in length. The nonspecific effects occur because dsRNA activates two enzymes: PKR, which in its active form phosphorylates the translation initiation factor eIF2 to shut down all protein synthesis, and 2',5' oligoadenylate synthetase (2',5'-AS), which synthesizes a molecule that activates RNAse L, a nonspecific enzyme that targets all mRNAs. The nonspecific pathway may represent a host response to stress or viral infection, and, in general, the effects of the nonspecific pathway are preferably minimized under preferred methods of the present invention. Significantly, longer dsRNAs appear to be required to induce the nonspecific pathway and, accordingly, dsRNAs shorter than about 30 bases pairs are preferred to effect gene repression by RNAi (see Hunter et al., J Biol Chem 250: 409-17, 1975; Manche et al., Mol Cell Biol 12: 5239-5248, 1992; Minks et al., J Biol Chem 254: 10180-10183, 1979; and Elbashir et al., Nature 411: 494-498, 2001).

RNAi has been shown to be effective in reducing or eliminating the expression of numerous gene in a number of different organisms including *Caenorhabditiis elegans*, mouse eggs and embryos, and cultured cells, and appears to be an anciently evolved pathway available in eukaryotic plants and animals. RNAi has proven to be an effective means of decreasing gene expression in a variety of cell types including HeLa cells, NIH/3T3 cells, COS cells, 293 cells and BHK-21 cells, and typically decreases expression of a gene to lower levels than that achieved using antisense techniques and, indeed, frequently eliminates expression entirely (see Bass, Nature 411: 428-9, 2001). In mammalian cells, siRNAs are effective at concentrations that are several orders of magnitude below the concentrations typically used in antisense experiments (Elbashir et al., Nature 411: 494-8, 2001).

The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides of the invention may include 3' overhang ends. Exemplary 2-nucleotide 3' overhangs may be composed of ribonucleotide residues of any type and may even be composed of 2'-deoxythymidine residues, which lowers the cost of RNA synthesis and may enhance nuclease resistance of siRNAs in the cell culture medium and within transfected cells (see Elbashir et al., Nature 411: 494-8, 2001). Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the gene target and other factors readily discernable to the skilled artisan. Exemplary dsRNAs may be synthesized chemically or produced in vitro or in vivo using appropriate expression vectors. Exemplary synthetic RNAs include 21 nucleotide RNAs chemically synthesized using methods known in the art (e.g., Expedite RNA phosphoramidites and thymidine phosphoramidite (Proligo, Germany)). Synthetic oligonucleotides are preferably deprotected and gel-purified using methods known in the art (see, e.g., Elbashir et al., Genes Dev. 15: 188-200, 2001). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a target nucleic acid, such as, for example, a nucleic acid that hybridizes, under stringent and/or physiological conditions, to any of human or *Xenopus* TopBP1 proteins.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference. Messenger RNA (mRNA) is generally thought of as a linear molecule which contains the information for directing protein synthesis within the sequence of ribonucleotides, however studies have revealed a number of secondary and tertiary structures that exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three dimensional structure. A number of researchers have measured the binding energies of a large number of RNA duplex structures and have derived a set of rules which can be used to predict the secondary structure of RNA (see, e.g., Jaeger et al., Proc. Natl. Acad. Sci. USA 86: 7706, 1989; and Turner et al., Annu. Rev. Biophys. Biophys. Chem. 17:167, 1988). The rules are useful in identification of RNA structural elements and, in particular, for identifying single stranded RNA regions which may represent preferred segments of the mRNA to target for silencing RNAi, ribozyme or antisense technologies. Accordingly, preferred segments of the mRNA target can be identified for design of the RNAi mediating dsRNA oligonucleotides as well as for design of appropriate ribozyme and hammerhead ribozyme compositions of the invention.

The dsRNA oligonucleotides may be introduced into the cell by transfection with a heterologous target gene using carrier compositions such as liposomes, which are known in the art—e.g., Lipofectamine 2000 (Invitrogen) as described by the manufacturer for adherent cell lines. Transfection of dsRNA oligonucleotides for targeting endogenous genes may be carried out using Oligofectamine (Invitrogen). Transfection efficiency may be checked using fluorescence microscopy for mammalian cell lines after co-transfection of hGFP-encoding pAD3 (Kehlenback et al., J Cell Biol 141: 863-74, 1998). The effectiveness of the RNAi may be assessed by any of a number of assays following introduction of the dsRNAs. These include Western blot analysis using antibodies which recognize the target gene product following sufficient time for turnover of the endogenous pool after new protein synthesis is repressed, reverse transcriptase polymerase chain reaction and Northern blot analysis to determine the level of existing target mRNA.

Further compositions, methods and applications of RNAi technology are provided in U.S. patent application Nos. 6,278,039, 5,723,750 and 5,244,805, incorporated herein by reference.

Several different types of molecules have been used effectively in the RNAi technology.

Small interfering RNA (siRNA), sometimes known as short interfering RNA or silencing RNA, are a class of 20-25 nucleotide-long double-stranded RNA molecules that play a variety of roles in biology. Most notably, siRNA is involved in the RNA interference (RNAi) pathway where the siRNA interferes with the expression of a specific gene. In addition to their role in the RNAi pathway, siRNAs also act in RNAi-related pathways, e.g., as an antiviral mechanism or in shaping the chromatin structure of a genome. Synthetic siRNAs have been shown to be able to induce RNAi in mammalian cells. This discovery led to a surge in the use of siRNA/RNAi for biomedical research and drug development.

MicroRNA (miRNA) are a related class of gene regulatory small RNAs, typically 21-23 nt in length. They typically differ from siRNA because they are processed from single stranded RNA precursors and show only partially complementary to mRNA targets. Initial studies have indicated that miRNAs regulate gene expression post-transcriptionally at the level of translational inhibition at P-Bodies in the cytoplasm. However, miRNAs may also guide mRNA cleavage similar to siRNAs. This is often the case in plants where the target sites are typically highly complementary to the miRNA. While target sites in plant mRNAs can be found in the 5' UTR, open-reading frames and 3' UTR, in animals, it is the 3' UTR that is the main target. miRNAs are first transcribed as part of a primary microRNA (pri-miRNA). This is then processed by the Drosha with the help of Pasha/DGCR8 (=Microprocessor complex) into pre-miRNAs. The ~75 nt pre-miRNA is then exported to the cytoplasm by exportin-5, where it is then diced into 21-23 nt siRNA-like molecules by Dicer. In some cases, multiple miRNAs can be found on the pri-miRNA.

Short hairpin RNA (shRNA) is yet another type of RNA that may be used to effect RNAi. It is a sequence of RNA that makes a tight hairpin turn that can be used to silence gene expression. shRNA is transcribed by RNA polymerase III.

Currently, short-interfering RNAs (siRNAs) and short-hairpin RNAs (shRNAs) are being extensively used to silence various genes to tease out functions carried out by the genes. It is becoming easier to harness RNAi to silence specific genes, owing to the development of libraries of readymade shRNA and siRNA gene-silencing constructs by using a variety of sources. For example, RNAi Codex, which consists of a database of shRNA related information and an associated website, has been developed as a portal for publicly available shRNA resources and is accessible at http://codex.cshl dot org. RNAi Codex currently holds data from the Hannon-Elledge shRNA library and allows the use of biologist-friendly gene names to access information on shRNA constructs that can silence the gene of interest. It is designed to hold user-contributed annotations and publications for each construct, as and when such data become available. Olson et al. (*Nucleic Acids Res.* 34 (Database issue): D153-D157, 2006, incorporated by reference) have provided detailed descriptions about features of RNAi Codex, and have explained the use of the tool. All these information may be used to help design the various siRNA or shRNA targeting TopBP1 or other proteins of interest.

Ribozyme

Ribozyme molecules designed to catalytically cleave a target mRNA transcripts can also be used to prevent translation of the subject TopBP1 mRNAs and/or expression of TopBP1 (see, e.g., PCT International Publication WO90/11364; Sarver et al., Science 247: 1222-1225, 1990, and U.S. Pat. No. 5,093,246).

Ribozymes are enzymatic RNA molecules capable of catalyzing the specific cleavage of RNA. (For a review, see Rossi, Current Biology 4: 469-471, 1994). The mechanism of ribozyme action involves sequence specific hybridization of the ribozyme molecule to complementary target RNA, followed by an endonucleolytic cleavage event. The composition of ribozyme molecules preferably includes one or more sequences complementary to a target mRNA, and the well known catalytic sequence responsible for mRNA cleavage or a functionally equivalent sequence (see, e.g., U.S. Pat. No. 5,093,246, incorporated herein by reference in its entirety).

While ribozymes that cleave mRNA at site specific recognition sequences can be used to destroy target mRNAs, the use of hammerhead ribozymes is preferred. Hammerhead ribozymes cleave mRNAs at locations dictated by flanking regions that form complementary base pairs with the target mRNA. Preferably, the target mRNA has the following sequence of two bases: 5'-UG-3'. The construction and production of hammerhead ribozymes is well known in the art and is described more fully in Haseloff and Gerlach, Nature 334: 585-591, 1988; and see PCT Appln. No. WO89/05852, the contents of which are incorporated herein by reference. Hammerhead ribozyme sequences can be embedded in a stable RNA such as a transfer RNA (tRNA) to increase cleavage efficiency in vivo (Perriman et al., Proc. Natl. Acad. Sci.

USA, 92: 6175-79, 1995; de Feyter, and Gaudron, Methods in Molecular Biology, Vol. 74, Chapter 43, "Expressing Ribozymes in Plants," Edited by Turner, P. C, Humana Press Inc., Totowa, N.J.). In particular, RNA polymerase III-mediated expression of tRNA fusion ribozymes are well known in the art (see, Kawasaki et al., Nature 393: 284-9, 1998; Kuwabara et al., Nature Biotechnol. 16: 961-5, 1998; and Kuwabara et al., Mol. Cell. 2: 617-27, 1998; Koseki et al., J Virol 73: 1868-77, 1999; Kuwabara et al., Proc Natl Acad Sci USA 96: 1886-91, 1999; Tanabe et al., Nature 406: 473-4, 2000). There are typically a number of potential hammerhead ribozyme cleavage sites within a given target cDNA sequence. Preferably the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the C-terminal amino acid domains of, for example, long and short forms of target would allow the selective targeting of one or the other form of the target, and thus, have a selective effect on one form of the target gene product.

Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a target mRNA, such as an mRNA of a sequence represented in any of the human or Xenopus TopBP1 proteins. In addition, ribozymes possess highly specific endoribonuclease activity, which autocatalytically cleaves the target sense mRNA. The present invention extends to ribozymes which hybridize to a sense mRNA encoding a target gene such as a therapeutic drug target candidate gene, thereby hybridizing to the sense mRNA and cleaving it, such that it is no longer capable of being translated to synthesize a functional polypeptide product.

The ribozymes of the present invention also include RNA endoribonucleases (hereinafter "Cech-type ribozymes") such as the one which occurs naturally in Tetrahymena thermophila (known as the IVS, or L-19 IVS RNA) and which has been extensively described by Thomas Cech and collaborators (Zaug et al., Science 224:574-578, 1984; Zaug et al., Science 231: 470-475, 1986; Zaug et al., Nature 324: 429-433, 1986; published International patent application No. WO88/04300 by University Patents Inc.; Been, et al., Cell 47: 207-216, 1986). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene or nucleic acid sequence.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation. Because ribozymes, unlike antisense molecules, are catalytic, a lower intracellular concentration is required for efficiency.

In certain embodiments, a ribozyme may be designed by first identifying a sequence portion sufficient to cause effective knockdown by RNAi. The same sequence portion may then be incorporated into a ribozyme. In this aspect of the invention, the gene-targeting portions of the ribozyme or RNAi are substantially the same sequence of at least 5 and preferably 6, 7, 8, 9, 10, 11, 12, 13, 14, 15, 16, 17, 18, 19 or 20 or more contiguous nucleotides of a target nucleic acid, such as a nucleic acid of any of the human or Xenopus TopBP1 sequences. In a long target RNA chain, significant numbers of target sites are not accessible to the ribozyme because they are hidden within secondary or tertiary structures (Birikh et al., Eur J Biochem 245: 1-16, 1997). To overcome the problem of target RNA accessibility, computer generated predictions of secondary structure are typically used to identify targets that are most likely to be single-stranded or have an "open" configuration (see Jaeger et al., Methods Enzymol 183: 281-306, 1989). Other approaches utilize a systematic approach to predicting secondary structure which involves assessing a huge number of candidate hybridizing oligonucleotides molecules (see Milner et al., Nat Biotechnol 15: 537-41, 1997; and Patzel and Sczakiel, Nat Biotechnol 16: 64-8, 1998). Additionally, U.S. Pat. No. 6,251,588, the contents of which are hereby incorporated herein, describes methods for evaluating oligonucleotide probe sequences so as to predict the potential for hybridization to a target nucleic acid sequence. The method of the invention provides for the use of such methods to select preferred segments of a target mRNA sequence that are predicted to be single-stranded and, further, for the opportunistic utilization of the same or substantially identical target mRNA sequence, preferably comprising about 10-20 consecutive nucleotides of the target mRNA, in the design of both the RNAi oligonucleotides and ribozymes of the invention.

Antisense Nucleic Acids

A further aspect of the invention relates to the use of the isolated "antisense" nucleic acids to inhibit expression, e.g., by inhibiting transcription and/or translation of a subject TopBP1 nucleic acid. The antisense nucleic acids may bind to the potential drug target by conventional base pair complementarity, or, for example, in the case of binding to DNA duplexes, through specific interactions in the major groove of the double helix. In general, these methods refer to the range of techniques generally employed in the art, and include any methods that rely on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a TopBP1 polypeptide. Alternatively, the antisense construct is an oligonucleotide probe, which is generated ex vivo and which, when introduced into the cell causes inhibition of expression by hybridizing with the mRNA and/or genomic sequences of a target nucleic acid. Such oligonucleotide probes are preferably modified oligonucleotides, which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264,564; and 5,256,775). Additionally, general approaches to constructing oligomers useful in antisense therapy have been reviewed, for example, by Van der Krol et al., BioTechniques 6: 958-976, 1988; and Stein et al., Cancer Res 48: 2659-2668, 1988.

With respect to antisense DNA, oligodeoxyribonucleotides derived from the translation initiation site, e.g., between the −10 and +10 regions of the target gene, are preferred. Antisense approaches involve the design of oligonucleotides (either DNA or RNA) that are complementary to mRNA encoding the target polypeptide. The antisense oligonucleotides will bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well (Wagner, Nature 372: 333, 1994). Therefore, oligonucleotides complementary to either the 5' or 3' untranslated, non-coding regions of a gene could be used in an antisense approach to inhibit translation of that mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of mRNA, antisense nucleic acids should be at least six nucleotides in length, and are preferably less that about 100 and more preferably less than about 50, 25, 17 or 10 nucleotides in length.

It is preferred that in vitro studies are first performed to quantitate the ability of the antisense oligonucleotide to inhibit gene expression. It is preferred that these studies utilize controls that distinguish between antisense gene inhibition and nonspecific biological effects of oligonucleotides. It is also preferred that these studies compare levels of the target RNA or protein with that of an internal control RNA or protein. Results obtained using the antisense oligonucleotide may be compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or agents facilitating transport across the cell membrane (see, e.g., Letsinger et al., Proc. Natl. Acad. Sci. U.S.A. 86: 6553-6556, 1989; Lemaitre et al., Proc. Natl. Acad. Sci. 84: 648-652, 1987; PCT Publication No. WO88/09810) or the blood-brain barrier (see, e.g., PCT Publication No. WO89/10134), hybridization-triggered cleavage agents (see, e.g., Krol et al., BioTechniques 6: 958-976, 1988) or intercalating agents (see, e.g., Zon, Pharm. Res. 5: 539-549, 1988). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

The antisense oligonucleotide can also contain a neutral peptide-like backbone. Such molecules are termed peptide nucleic acid (PNA)-oligomers and are described, e.g., in Perry-O'Keefe et al., Proc. Natl. Acad. Sci. U.S.A. 93: 14670, 1996, and in Eglom et al., Nature 365: 566, 1993. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet a further embodiment, the antisense oligonucleotide is an alpha-anomeric oligonucleotide. An alpha-anomeric oligonucleotide forms specific double-stranded hybrids with complementary RNA in which, contrary to the usual antiparallel orientation, the strands run parallel to each other (Gautier et al., Nucl. Acids Res. 15: 6625-6641, 1987). The oligonucleotide is a 2'-O-methylribonucleotide (Inoue et al., Nucl. Acids Res. 15: 6131-6148, 1987), or a chimeric RNA-DNA analogue (Inoue et al., FEBS Lett. 215: 327-330, 1987).

While antisense nucleotides complementary to the coding region of a target mRNA sequence can be used, those complementary to the transcribed untranslated region may also be used.

In certain instances, it may be difficult to achieve intracellular concentrations of the antisense sufficient to suppress translation on endogenous mRNAs. Therefore a preferred approach utilizes a recombinant DNA construct in which the antisense oligonucleotide is placed under the control of a strong pol III or pol II promoter. The use of such a construct to transfect target cells will result in the transcription of sufficient amounts of single stranded RNAs that will form complementary base pairs with the endogenous potential drug target transcripts and thereby prevent translation. For example, a vector can be introduced such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, Nature 290: 304-310, 1981), the promoter contained in the 3' long terminal repeat of Rous sarcoma virus (Yamamoto et al., Cell 22: 787-797, 1980), the herpes thymidine kinase promoter (Wagner et al., Proc. Natl. Acad. Sci. U.S.A. 78: 1441-1445, 1981), the regulatory sequences of the metallothionein gene (Brinster et al, Nature 296: 39-42, 1982), etc. Any type of plasmid, cosmid, YAC or viral vector can be used to prepare the recombinant DNA construct, which can be introduced directly into the tissue site.

Alternatively, target gene expression can be reduced by targeting deoxyribonucleotide sequences complementary to the regulatory region of the gene (i.e., the promoter and/or enhancers) to form triple helical structures that prevent transcription of the gene in target cells in the body (see generally, Helene, Anticancer Drug Des. 6(6): 569-84, 1991; Helene et al., Ann. N.Y. Acad. Sci., 660: 27-36, 1992; and Maher, Bioassays 14(12): 807-15, 1992).

Nucleic acid molecules to be used in triple helix formation for the inhibition of transcription are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential target sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Morpholinos

In certain embodiments, the antisense oligonucleotides are Morpholino antisenses. Morpholinos are synthetic molecules which are the product of a redesign of natural nucleic acid structure. Usually 25 bases in length, they bind to complementary sequences of RNA by standard nucleic acid base-pairing. Structurally, the difference between Morpholinos and DNA is that while Morpholinos have standard nucleic acid bases, those bases are bound to morpholine rings instead of deoxyribose rings, and linked through phosphorodiamidate groups instead of phosphates. Replacement of anionic phosphates with the uncharged phosphorodiamidate groups eliminates ionization in the usual physiological pH range, so Morpholinos in organisms or cells are uncharged molecules. Morpholinos are not chimeric oligos; the entire backbone of a Morpholino is made from these modified subunits. Morpholinos are most commonly used as single-stranded oligos, though heteroduplexes of a Morpholino strand and a complementary DNA strand may be used in combination with cationic cytosolic delivery reagents.

Unlike many antisense structural types (e.g., phosphorothioates), Morpholinos do not degrade their target RNA molecules. Instead, Morpholinos act by "steric blocking," binding to a target sequence within an RNA and simply getting in the way of molecules which might otherwise interact with the RNA. Morpholino oligos are often used to investigate the role of a specific mRNA transcript in an embryo, such as eggs or embryos of zebrafish, African clawed frog (Xenopus), chick, and sea urchin, producing morphant embryos. With appropriate cytosolic delivery systems, Morpholinos are effective in cell culture.

Morpholinos are being developed as pharmaceuticals under the name "NeuGenes" by AVI BioPharma Inc. They have been used in mammals ranging from mice to humans and some are currently being tested in clinical trials.

Bound to the 5'-untranslated region of messenger RNA (mRNA), Morpholinos can interfere with progression of the ribosomal initiation complex from the 5' cap to the start codon. This prevents translation of the coding region of the targeted transcript (called "knocking down" gene expression). Morpholinos provide a convenient means of knocking down expression of the protein and learning how that knockdown changes the cells or organism. Some Morpholinos knock down expression so effectively that after degradation of preexisting proteins the targeted proteins become undetectable by Western blot.

Morpholinos can also interfere with pre-mRNA processing steps, usually by preventing the splice-directing snRNP complexes from binding to their targets at the borders of introns on a strand of pre-RNA. Preventing U1 (at the donor site) or U2/U5 (at the polypyrimidine moiety and acceptor site) from binding can cause modified splicing, commonly leading to exclusions of exons from the mature mRNA. Targeting some splice targets results in intron inclusions, while activation of cryptic splice sites can lead to partial inclusions or exclusions. Targets of U11/U12 snRNPs can also be blocked. Splice modification can be conveniently assayed by reverse-transcriptase polymerase chain reaction (RT-PCR) and is seen as a band shift after gel electrophoresis of RT-PCR products.

Morpholinos have also been used to block miRNA activity, ribozyme activity, intronic splice silencers, and splice enhancers. U2 and U12 snRNP functions have been inhibited by Morpholinos. Morpholinos targeted to "slippery" mRNA sequences within protein coding regions can induce translational frameshifts. Activities of Morpholinos against this variety of targets suggest that Morpholinos can be used as a general-purpose tool for blocking interactions of proteins or nucleic acids with mRNA.

DNA Enzyme

A further aspect of the invention relates to the use of DNA enzymes to inhibit expression of target gene. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid.

There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions.

Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence.

When synthesizing the DNA enzyme, the specific antisense recognition sequence that will target the enzyme to the message is divided so that it comprises the two arms of the DNA enzyme, and the DNA enzyme loop is placed between the two specific arms.

Methods of making and administering DNA enzymes can be found, for example, in U.S. Pat. No. 6,110,462. Similarly, methods of delivery DNA ribozymes in vitro or in vivo include methods of delivery RNA ribozyme, as outlined in detail above. Additionally, one of skill in the art will recognize that, like antisense oligonucleotide, DNA enzymes can be optionally modified to improve stability and improve resistance to degradation.

Antisense RNA and DNA, ribozyme, RNAi and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

Antibodies

Antibodies against an epitope located inside or nearby the ATR activation domain of TopBP1 may effectively block the activating function of TopBP1, thus inhibiting ATR activation by TopBP1. Thus another aspect of the invention pertains to an antibody specifically reactive with an epitope located inside or sufficiently close to the ATR activation domain of TopBP1, which antibody, when bound to TopBP1, blocks ATR activation by TopBP1.

One exemplary antibody is the anti-Xmus101 antibody, HU142, which recognizes the COOH-terminal 333 amino acids of Xmus101 (Yan et al., J. Cell Biol. 173(2): 181-186, 2006).

Other similar antibodies or fragments thereof may be readily available, or may be readily produced using conventional molecular biology techniques. For example, by using immunogens derived from, for example, an ATR activation domain of TopBP1, anti-protein/anti-peptide antisera or monoclonal antibodies can be made by standard protocols (See, for example, *Antibodies: A Laboratory Manual* ed. by Harlow and Lane (Cold Spring Harbor Press: 1988)). A mammal, such as a mouse, a hamster or rabbit can be immunized with an immunogenic form of the peptide (e.g., an ATR activation domain of TopBP1, or an antigenic fragment thereof, which is capable of eliciting an antibody response). Techniques for conferring immunogenicity on a protein or peptide, include conjugation to carriers or other techniques, are well known in the art. An immunogenic portion of a polypeptide can be administered in the presence of adjuvant. The progress of immunization can be monitored by detection of antibody titers in plasma or serum. Standard ELISA or other immunoassays can be used with the immunogen as antigen to assess the levels of antibodies. In a preferred embodiment, the subject antibodies are immuno-specific for antigenic determinants of an ATR activation domain of TopBP1 (or a variant at least 80%, 85%, 90%, 95%, or 98% identical thereto). In certain embodiment, the immunospecific subject antibodies do not substantially cross react with a non-vertebrate (such as yeast) TopBP1-related protein. By "not substantially cross react," it is meant that the antibody has a binding affinity for a non-homologous protein which is at least one order of magnitude, more preferably at least 2 orders of magnitude, and even more preferably at least 3 orders of magnitude less than the binding affinity of the antibody for an ATR activating domain of TopBP1.

Following immunization of an animal with an antigenic preparation of a protein, antisera can be obtained and, if desired, polyclonal antibodies isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include for example, the hybridoma technique (originally developed by Kohler and Milstein, Nature 256: 495-497, 1975), the human B cell hybridoma technique (Kozbar et al., Immunology Today 4: 72, 1983), and the EBV-hybridoma technique to produce human monoclonal antibodies (Cole et al., Monoclonal Antibodies and Cancer Therapy, Alan R. Liss, Inc. pp. 77-96, 1985). Hybridoma cells can be screened immunochemically for production of antibodies specifically reactive with the polypeptides of the present invention and monoclonal antibodies isolated from a culture comprising such hybridoma cells. Similarly, hybridoma cells can be screened for the production of antibodies specifically reactive with the polypeptides of the present invention, which also do not substantially cross-reactive with one or more other polypeptides.

The term antibody as used herein is intended to include fragments thereof which are also specifically reactive with one of the subject polypeptides. Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. The antibody of the present invention is further intended to include bispecific and chimeric molecules having affinity for a protein conferred by at least one CDR region of the antibody.

Both monoclonal and polyclonal antibodies (Ab) have many uses including (1) blocking or antagonizing one or more activities of the subject polypeptide, (2) for detection of the subject proteins (in vitro or in vivo) using standard immunohistochemical/immunocytochemical techniques, (3) for immunodepletion, (4) for immuno-precipitation, and (5) for the immunological screening of cDNA libraries constructed in expression vectors such as λgt11, λgt18-23, λZAP, and λORF8.

The antibodies of the invention can be bound to many different carriers and used to detect the presence of an antigen comprising the polypeptides of the invention. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds.

Another technique that may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti hapten antibodies.

Antibodies, especially monoclonal antibodies or fragments thereof may be cloned, and their coding sequences may be introduced into a target cell by, for example, using any of the expression vectors (viral-based or non-viral vectors) described herein. Such antibodies or fragments, or peptidomimetics thereof may be used to block ATR activation by TopBP1.

Dominant Negative TopBP1

Certain dominant negative (DN) TopBP1 proteins or fragments thereof may compete with the wild-type TopBP1 for binding to the ATR-ATRIP complex and/or effectors, yet lacks the ability to activate ATR once bound. Such dominant negative mutants of TopBP1 may also inhibit TopBP1-mediated ATR activation, and thus can be the inhibitors of the subject invention.

For example, Applicants have identified a point mutation in the ATR activation domain of TopBP1, W1138R, which retains the ability to bind to the ATR-ATRIP complex, but lacks the ability to activate ATR as the wild-type sequence can. If overexpressed, such a DN TopBP1 peptide may block ATR activation by TopBP1.

Similarly, the domain on ATR or ATRIP that participates in TopBP1 binding may also be used to titrate out the available TopBP1, thus disrupting TopBP1-mediated ATR activation.

Another important residue in the ATR activation domain of TopBP1 is Ser1131. Phosphorylation of this residue is critical for the checkpoint response. Thus mutating Ser1131 to Ala or another aliphatic amino acids may abolish ATR activation by TopBP1 without losing ATR-ATRIP binding.

Other such DN mutants of TopBP1 can be readily made using conventional biological techniques. For example, Ala scanning mutagenesis may be used to mutate the entire region of the ATR activation domain of TopBP1, with one or more adjacent (or discontinuous) residues mutated in each candidate mutants. Such mutants may be tested for binding to ATR-ATRIP, and their ability to stimulate ATR kinase activation. Since the ATR activation domain of TopBP1 is conserved among different species, the most conserved residues among different species may be selectively mutated to isolate DN mutants that can no longer activate ATR without losing entirely the ability to bind the ATR-ATRIP complex.

Peptidomimetics

The invention also provides for reduction of a polypeptide (such as the ATR activatin domain and variants thereof, or dominant negative inhibitors thereof) to generate mimetics, e.g., peptide or non-peptide agents, which are able to retain the function of the polypeptide (e.g., activate or inhibit ATR function), or even enhance the function of the polypeptide from which such mimetics are derived. For example, an exemplary ATR activation domain mimetic, like the ATR activation domain of TopBP1, may activate the ability of an ATR polypeptide to phosphorylate Chk1, to bind single-stranded DNA or double-stranded DNA.

Activators of ATR Activation by TopBP1

In certain embodiments, ATR may be activated by the full-length TopBP1 polypeptide, including a TopBP1 from the same species or one from a different species. Polynucleotides encoding such polypeptides may also be used.

In certain embodiments, the ATR activation domain of TopBP1 may be an activator of ATR activation by TopBP1. Other non-limiting examples of activator of ATR activation by TopBP1 include: a TopBP1 activator (e.g., oligonucleotide duplex AT70), a TopBP1 transcriptional activator (such as transcription factors E2F1-3, early growth response protein-I or Egr-1), a TopBP1 stabilizer (such as the PML tumor suppressor gene), or a polypeptide comprising an ATR activation domain of TopBP1 (supra), or a polynucleotide encoding such a polypeptide.

For example, the AT70 system in *X. laevis* egg extracts (see Kumagai and Dunphy, *Mol Cell* 6(4): 839-849, 2000, incorporated by reference) uses two short oligonucleotides, A70 and T70. When these oligonucleotides are annealed to one another and added to extracts, ATR kinase activity is activated.

The invention also includes variants of the ATR activation domain of TopBP1. Such variants may include additional sequences, such as epitope tags (FLAG tag, 6-His tag, etc.), heterologous fusions (such as GST fusions, etc.), or additional sequences of the TopBP1 protein; or may have different degrees of deletion of the minimal ATR activation domain (that retains 100% of the full-length activity); or both. In certain embodiments, the variants retains at least about 70%, 80%, 90%, or 95% of the full length ATR activation activity.

Variants of the subject ATR activation domain of TopBP1 polypeptides can be generated by mutagenesis, such as by discrete point mutation(s), or by truncation. For instance, mutation can give rise to variants which retain substantially the same biological activity of the activation domain from which it was derived.

The invention also relates to isolated nucleic acids comprising nucleotide sequences encoding the ATR activation domain of TopBP1, and/or functional fragments/equivalents/variants thereof. Functional equivalents include polynucleotide sequences encoding a polypeptide sharing at least about 70, 75, 80, 85, 90, 95, 97, 99% or more sequence identity to the human or *Xenopus* ATR activation domain of TopBP1, and are capable of activating a biological function of ATR, such as activating the ATR kinase activity. Equivalent nucleotide sequences will also include sequences that differ by one or more nucleotide substitutions, additions or deletions, such as allelic variants; and will, therefore, include sequences that differ from the nucleotide sequence of the human or *Xenopus* ATR activation domain of TopBP1 due to the degeneracy of the genetic code. Equivalents will also include nucleotide sequences that hybridize under stringent conditions (e.g., equivalent to about 20-27° C. below the melting temperature ($T_m$) of the DNA duplex formed in about 1M salt) to the nucleotide sequences of the human or *Xenopus* ATR activation domain of TopBP1. Appropriate stringency conditions which promote DNA hybridization, include, for example, 6.0× sodium chloride/sodium citrate (SSC) at about 45° C., followed by a wash of 2.0×SSC at 50° C., and are generally known to those skilled in the art or can be found in, for example, *Current Protocols in Molecular Biology*, John Wiley & Sons, N.Y. (1989), 6.3.1-6.3.6. Depending on specific needs, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature or about 22° C., to high stringency conditions at about 65° C.

Nucleic acids having a sequence that differs from the nucleotide sequences encoding the subject ATR activation domains due to degeneracy in the genetic code are also within the scope of the invention. Such nucleic acids encode functionally equivalent peptides, but differ due to degeneracy in the genetic code. For example, a number of amino acids are designated by more than one triplet. Codons that specify the same amino acid, or synonyms (for example, CAU and CAC each encode histidine) may result in "silent" mutations which do not affect the amino acid sequence. However, it is expected that DNA sequence polymorphisms that do lead to changes in the amino acid sequences will also exist. One skilled in the art will appreciate that these variations in one or more nucleotides (up to about 3-5% of the nucleotides) of the nucleic acids encoding polypeptides having substantially the same activity of an ATR activation domain of TopBP1 may exist among individuals of a given species due to natural allelic variation.

Nucleic acids within the scope of the invention may also contain linker sequences, modified restriction endonuclease sites and other sequences useful for molecular cloning, expression or purification of recombinant forms of the subject polypeptides.

(iv) Exemplary Delivery

The modulators of the invention may be delivered to a host animal in vivo or a host cell in vitro using various art-recognized means, depending on the specific identity of the modulators to be delivered.

For example, when a polynucleotide modulator (e.g., those encoding a ATR activation domain, etc.) is to be delivered, various expression vectors containing a subject polynucleotide, operably linked to at least one transcriptional regulatory sequence may be used. Operably linked is intended to mean that the nucleotide sequence is linked to a regulatory sequence in a manner which allows expression of the nucleotide sequence. Regulatory sequences are art-recognized and are selected to direct expression of the subject proteins. Accordingly, the term transcriptional regulatory sequence includes promoters, enhancers and other expression control elements. Such regulatory sequences are described in, for example, Goeddel; *Gene Expression Technology: Methods in Enzymology* 185, Academic Press, San Diego, Calif. (1990).

Any of a wide variety of expression control sequences, sequences that control the expression of a DNA sequence when operatively linked to it, may be used in these vectors to express DNA sequences encoding the polypeptides of this invention. Such useful expression control sequences include, for example, a viral LTR, such as the LTR of the Moloney murine leukemia virus, the early and late promoters of SV40, adenovirus or cytomegalovirus immediate early promoter, the lac system, the trp system, the TAC or TRC system, T7 promoter whose expression is directed by T7 RNA polymerase, the major operator and promoter regions of phage λ, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other proteins encoded by the vector, such as antibiotic markers, should also be considered.

Moreover, the gene constructs of the present invention can also be used to deliver nucleic acids encoding the subject polypeptides. Thus, another aspect of the invention features expression vectors for in vivo or in vitro transfection and expression of a subject polypeptide in particular cell types.

Expression constructs of the subject polypeptide may be administered in any biologically effective carrier, e.g., any formulation or composition capable of effectively delivering the recombinant gene to cells in vivo or in vitro. Approaches include insertion of the subject gene in viral vectors including recombinant retroviruses, adenovirus, adeno-associated virus, and herpes simplex virus-1, or recombinant bacterial or eukaryotic plasmids. Viral vectors transfect cells directly. Plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or CaPO4 precipitation. One of skill in the art can readily select from amongst available vectors and methods of delivery in order to optimize expression in a particular cell type or under particular conditions.

A preferred approach for introduction of nucleic acid into a cell is by use of a viral vector containing nucleic acid, e.g., a cDNA, encoding the particular form of the polypeptide. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors are generally understood to be the recombinant gene delivery system of choice for the transfer of exogenous genes. These vectors provide efficient delivery of genes into cells, and the transferred nucleic acids are stably integrated into the chromosomal DNA of the host. A major prerequisite for the use of retroviruses is to ensure the safety of their use, particularly with regard to the possibility of the spread of wild-type virus in the cell population. The development of specialized cell lines (termed "packaging cells") which produce only replication-defective retroviruses has increased the utility of retroviruses for gene therapy, and defective retroviruses are well characterized for use in gene transfer for gene therapy purposes (for a review see Miller, *Blood* 76: 271, 1990). Thus, recombinant retrovirus can be constructed in which part of the retroviral coding sequence (gag, pol, env) has been replaced by nucleic acid encoding one of the subject proteins rendering the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in, for example, *Current Protocols in Molecular Biology*, Ausubel et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines for preparing both ecotropic and amphotropic retroviral systems include ψCrip, ψCre, ψ2 and ψAm. Retroviruses have been used to introduce a variety of genes into many different cell types, including neuronal cells, in vitro and/or in vivo (see for example Eglitis et al., Science 230: 1395-1398, 1985; Danos and Mulligan, Proc. Natl. Acad. Sci. USA 85: 6460-6464, 1988; Wilson et al., Proc. Natl. Acad. Sci. USA 85: 3014-3018, 1988; Armentano et al., Proc. Natl. Acad. Sci. USA 87: 6141-6145, 1990; Huber et al., Proc. Natl. Acad. Sci. USA 88: 8039-8043, 1991; Ferry et al., Proc. Natl. Acad. Sci. USA 88: 8377-8381, 1991; Chowdhury et al., Science 254: 1802-1805, 1991; van Beusechem et al., Proc. Natl. Acad. Sci. USA 89: 7640-7644, 1992; Kay et al., Human Gene Therapy 3: 641-647, 1992; Dai et al., Proc. Natl. Acad. Sci. USA 89: 10892-10895, 1992; Hwu et al., J. Immunol. 150: 4104-4115, 1993; U.S. Pat. No. 4,868,116; U.S. Pat. No. 4,980,286; PCT Application WO 89/07136; PCT Application WO 89/02468; PCT Application WO 89/05345; and PCT Application WO 92/07573). Incorporated by reference.

Furthermore, it has been shown that it is possible to limit the infection spectrum of retroviruses and consequently of retroviral-based vectors, by modifying the viral packaging proteins on the surface of the viral particle (see, for example PCT publications WO93/25234 and WO94/06920). For instance, strategies for the modification of the infection spectrum of retroviral vectors include: coupling antibodies specific for cell surface antigens to the viral env protein (Roux et al., PNAS 86: 9079-9083, 1989; Julan et al., J. Gen Virol 73: 3251-3255, 1992; and Goud et al., Virology 163: 251-254, 1983); or coupling cell surface receptor ligands to the viral env proteins (Neda et al., J Biol Chem 266: 14143-14146, 1991). Coupling can be in the form of the chemical cross-linking with a protein or other variety (e.g., lactose to convert the env protein to an asialoglycoprotein), as well as by generating fusion proteins (e.g., single-chain antibody/env fusion proteins). This technique, while useful to limit or otherwise direct the infection to certain tissue types, can also be used to convert an ecotropic vector in to an amphotropic vector.

Moreover, use of retroviral gene delivery can be further enhanced by the use of tissue- or cell-specific transcriptional regulatory sequences which control expression of the gene of the retroviral vector.

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example Berkner et al., BioTechniques 6: 616, 1988; Rosenfeld et al., Science 252: 431-434, 1991; and Rosenfeld et al., Cell 68: 143-155, 1992. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses can be advantageous in certain circumstances in that they can be used to infect a wide variety of cell types, including airway epithelium (Rosenfeld et al., 1992, supra), endothelial cells (Lemarchand et al., Proc. Natl. Acad. Sci. USA 89: 6482-6486, 1992), hepatocytes (Herz and Gerard, Proc. Natl. Acad. Sci. USA 90: 2812-2816, 1993) and muscle cells (Quantin et al., Proc. Natl. Acad. Sci. USA 89: 2581-2584, 1992). Furthermore, the virus particle is relatively stable and amenable to purification and concentration, and as above, can be modified so as to affect the spectrum of infectivity.

Yet another viral vector system useful for delivery of one of the subject genes is the adeno-associated virus (AAV). Adeno-associated virus is a naturally occurring defective virus that requires another virus, such as an adenovirus or a herpes virus, as a helper virus for efficient replication and a productive life cycle. (For a review, see Muzyczka et al., Curr. Topics in Micro. and Immunol. 158: 97-129, 1992). It is also one of the few viruses that may integrate its DNA into non-dividing cells, and exhibits a high frequency of stable integration (see for example Flotte et al., Am. J. Respir. Cell. Mol. Biol. 7: 349-356, 1992; Samulski et al., J. Virol. 63: 3822-3828, 1989; and McLaughlin et al., J. Virol. 62: 1963-1973, 1989). Vectors containing as little as 300 base pairs of AAV can be packaged and can integrate. Space for exogenous DNA is limited to about 4.5 kb. An AAV vector such as that described in Tratschin et al. (Mol. Cell. Biol. 5: 3251-3260, 1985) can be used to introduce DNA into cells. A variety of nucleic acids have been introduced into different cell types using AAV vectors (see for example Hermonat et al., Proc. Natl. Acad. Sci. USA 81: 6466-6470, 1984; Tratschin et al., Mol. Cell. Biol. 4: 2072-2081, 1985; Wondisford et al., Mol. Endocrinol. 2: 32-39, 1988; Tratschin et al., J. Virol. 51: 611-619, 1984; and Flotte et al., J. Biol. Chem. 268: 3781-3790, 1993).

The above cited examples of viral vectors are by no means exhaustive. Herpes-simplex viral vectors and lentiviral vectors are just two additional types of viral vectors which can be used in the present invention.

In addition to viral transfer methods, such as those illustrated above, non-viral methods can also be employed to cause expression of a subject polypeptide. Most nonviral methods of gene transfer rely on normal mechanisms used by cells for the uptake and intracellular transport of macromolecules. In preferred embodiments, non-viral gene delivery systems of the present invention rely on endocytic pathways for the uptake of the subject polypeptide gene by the targeted cell. Exemplary gene delivery systems of this type include liposomal derived systems, poly-lysine conjugates, and artificial viral envelopes.

Another aspect of the present invention concerns recombinant forms of the subject proteins (e.g., the subject ATR activation domains of TopBP1, etc.). Recombinant polypeptides preferred by the present invention, in addition to native proteins, are at least 60% identical, more preferably 70% identical and most preferably 80% identical with an amino acid sequence of the human or Xenopus ATR activation domain of TopBP1. Additional preferred recombinant polypeptides comprise an amino acid sequence at least 85%, 90%, 95%, 98%, or 100% identical to an amino acid sequence of human or Xenopus ATR activation domain of TopBP1. The invention further concerns polypeptides comprising an amino acid sequence at least 80%, 85%, 90%, 95%, 98% or 100% identical to a functional fragment of the human or Xenopus ATR activation domain of TopBP1. Any of the foregoing polypeptides may be characterized by being able to stimulate at least one activity of an ATR polypeptide, including: (1) the ability to phosphorylate Chk1, (2) the ability to bind single-stranded DNA, (3) the ability to bind double stranded DNA, (4) the ability to induce cell cycle arrest in response to DNA damage, and/or (5) the ability to induce cell cycle arrest in response to a DNA replication block.

The term "recombinant protein" refers to a polypeptide of the present invention which is produced by recombinant DNA techniques, wherein generally, nucleic acid encoding a polypeptide is inserted into a suitable expression vector which is in turn used to transform a host cell to produce the heterologous protein. Moreover, the phrase "derived from," with respect to a recombinant gene, is meant to include within the meaning of "recombinant protein" those proteins having an amino acid sequence of a native protein, or an amino acid sequence similar thereto which is generated by mutations including substitutions and deletions (including truncation) of a naturally occurring form of the protein (e.g., variants).

(v) Method of Screening

One aspect of the invention provides a screening method for identifying additional modulator of ATR activation by TopBP1, the method comprising: (1) providing a mixture comprising TopBP1 and ATR; (2) contacting the mixture with a candidate compound; and, (3) determining the binding of TopBP1 to ATR, and/or the activation of the kinase activity of ATR; wherein a statistically significant change either in the binding of TopBP1 to ATR or the activation of the kinase activity of ATR or both in the presence of the test compound compared to those in the absence of the test compound is indicative that the text compound is a modulator of TopBP1 activation of ATR.

The modulators of ATR activation by TopBP1 are either agonists (activators) or antagonists (inhibitors) of ATR activation. Exemplary agents (e.g., a single agent, a combination of two or more agents, a library of agents) may include nucleic acids, peptides, proteins, antibodies, antisense RNAs (including antisense Morpholino oligomers), RNAi constructs, chemical compounds, and small organic molecules. ATR activities which may be modulated (increased or decreased) by said one or more agents in the presence of TopBP1 may include: (1) the ability to phosphorylate a Chk1 protein, (2) the ability to bind single-stranded DNA, (3) the ability to bind double-stranded DNA, (4) the ability to induce cell cycle delay in response to DNA damage, and/or (5) the ability to induce cell cycle delay in response to a DNA replication block. A variety of assay formats will suffice and, in light of the present inventions, will be comprehended by the skilled artisan. In one particular embodiment, ATR activation may be monitored by phosphorylation of an ATR substrate (such as Chk1) by an ATR polypeptide.

In many drug screening programs which test libraries of compounds and natural extracts, high throughput assays are desirable in order to maximize the number of agents surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test agent. Cell free systems include purely in vitro systems (preparations of proteins and agents combined in a test tube, Petri dish, etc.), as well as cell free systems such as those prepared from egg extracts. Exemplary egg extracts can be prepared from amphibians, clams, sea urchins, and the like. Although egg extracts can theoretically be prepared from any species, preferred egg extracts are prepared from species whose eggs are large (i.e., contain a large amount of cytoplasm—and thus from which a relatively large amount of extract can be readily prepared) and easily obtained. Moreover, the effects of cellular toxicity and/or bioavailability of the test agents can be generally ignored in such a system, the assay instead being focused primarily on the effect of the agent.

In an exemplary screening assay of the present invention, ATR kinase assay is used as a read-out (while in other assays, nucleotide binding by ATR may be used as read-out). In this assay, the agent of interest (e.g., an individual agent, a combination of two or more agents, a library of agents) is contacted with a mixture comprising TopBP1 and ATR. The preparation is contacted with said agent prior to phosphorylation of an ATR substrate (e.g., Chk1) by ATR, and the ability of the agent to modulate (either increase or decrease) the phosphorylation of the substrate by ATR is measured and compared to the wildtype phosphorylation of the substrate by ATR (as, for example, in a control preparation which is not contacted with the agent). The efficacy of the agent can be assessed by generating dose response curves from data obtained using various concentrations of the test agent. Moreover, a control assay can also be performed to provide a baseline for comparison. One useful control omits TopBP1 in the mixture (e.g., the method further comprises determining the extent of ATR activity change by the test compound in the absence of TopBP1 in the mixture). If a test agent or compound activates ATR in the absence of TopBP1, it may be a non-specific kinase activator, and may not be relevant in the TopBP1-mediated ATR activation.

Examples of ATR activities, which activation may be modulated by said agent and which may be assayed in the present methods include phosphorylation of Xchk1, phosphorylation of another substrate in the preparation, binding of single-stranded DNA, binding of double-stranded DNA, ability to induce cell cycle delay in response to DNA damage, and/or the ability to induce cell cycle delay in response to a DNA replication block.

In any of the foregoing screening methods, the invention further contemplates that screening assays may be performed to identify agents which modulate (either increase or decrease) the TopBP1-mediated activation of either a wild-type ATR polypeptide or a variant ATR polypeptide (e.g., a mutant form of the polypeptide which may have compromised activity—either increased or decreased). For example, a mixture comprising a variant ATR polypeptide (instead of a wild-type ATR) may be used in the subject screening method. The variant may have increased or decreased activity compared to the wild-type ATR. Such variants may be useful to change the sensitivity of the screening method to suite particular needs.

The invention further contemplates methods of identifying agents which modulate the phosphorylation of a variant Chk1 polypeptide by an ATR polypeptide activated by TopBP1, as well as agents which modulate ATR activation by TopBP1 in a cell containing a mutation in another protein involved in sensing or responding to DNA damage and/or a DNA replication block (e.g., ATM, Chk1, Chk2, Cds1, claspin, etc). The invention further contemplates methods of identifying agents which modulate ATR activation by TopBP1 in a cell containing a mutation in another protein involved in regulation of the cell cycle (e.g., Cdc2, Cdc25, p53, BRCA1, etc.).

In addition to cell-free assays, such as described above, the invention further contemplates the generation of cell-based assays for identifying agents which modulate (increase or decrease) ATR activation by TopBP1. Such cell based assays can employ any cell-type including cells which are sensitive to ATR mediated cell cycle delay. The invention contemplates the use of cells which comprise a wildtype ATR polypeptide, as well as cells comprising a variant ATR polypeptide. The invention further contemplates the use of cells comprising mutations in one or more other proteins, as described in detail herein.

One class of agents which may modulate the activation of at least one activity of ATR by TopBP1 are agents which bind (either directly or indirectly) to an ATR polypeptide, an ATRIP polypeptide, and/or a TopBP1 polypeptide. Accordingly, the present invention contemplates screening for agents which bind to an ATR polypeptide, an ATRIP polypeptide, and/or a TopBP1 polypeptide. Many well known methods exist in the art for assessing protein-protein, protein-nucleic acid, protein-antibody, and protein-chemical/small molecule interaction. Exemplary methods include two- or three-hybrid screens, affinity chromatography, immunoprecipitation, and the like. One of skill in the art can select amongst commonly used methods for detecting the interaction of an ATR polypeptide with an agent including proteins, nucleic acids, small molecule, chemical compounds, antibodies, etc.

(vi) Other Aspects of the Invention

The present invention further pertains to methods of producing any of the subject polypeptides, such as the TopBP1 ATR activation domains or various fragments, derivatives thereof. For example, a host cell transfected with a nucleic acid vector directing expression of a nucleotide sequence encoding the subject polypeptides can be cultured under appropriate conditions to allow expression of the peptide to occur. The polypeptide may be secreted and isolated from a mixture of cells and medium containing the recombinant polypeptide. Alternatively, the peptide may be retained cytoplasmically by removing the signal peptide sequence from the recombinant gene and the cells harvested, lysed and the protein isolated. A cell culture includes host cells, media and other by-products. Suitable media for cell culture are well known in the art. The recombinant polypeptide can be isolated from cell culture medium, host cells, or both using techniques known in the art for purifying proteins including ion-exchange chromatography, gel filtration chromatography, ultrafiltration, electrophoresis, and immunoaffinity purification with antibodies specific for such peptide. In a preferred embodiment, the recombinant polypeptide is a fusion protein containing a domain which facilitates its purification, such as a GST fusion protein. In another preferred embodiment, the subject recombinant polypeptide may include one or more additional domains which facilitate immunodetection, purification, and the like. Exemplary domains include HA, FLAG, GST, His, and the like.

This invention also pertains to a host cell transfected to express a recombinant form of the subject polypeptides. The host cell may be any prokaryotic or eukaryotic cell. Thus, a nucleotide sequence derived from the cloning of a protein (for example, a *Xenopus* ATR activation domain) encoding all or a selected portion of the full-length protein, can be used to produce a recombinant form of a polypeptide via microbial or eukaryotic cellular processes. Ligating the polynucleotide sequence into a gene construct, such as an expression vector, and transforming or transfecting into hosts, either eukaryotic (yeast, avian, insect or mammalian) or prokaryotic (bacterial cells), are standard procedures used in producing other well-known proteins. Similar procedures, or modifications thereof, can be employed to prepare recombinant polypeptides by microbial means or tissue-culture technology in accord with the subject invention. Such methods may also be effectively used to produce experimentally useful proteins, which may include all or a portion of the subject nucleic acids. For example, such methods are used to produce fusion proteins including domains which facilitate purification or immunodetection, and to produce recombinant mutant forms of a protein (for example a kinase dead form of a protein which acts as a kinase).

The recombinant genes can be produced by ligating nucleic acid encoding a protein, or a portion thereof, into a vector suitable for expression in either prokaryotic cells, eukaryotic cells, or both. Expression vectors for production of recombinant forms of the subject polypeptides include plasmids and other vectors. For instance, suitable vectors for the expression of a polypeptide include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al., in Experimental Manipulation of Gene Expression, ed. M. Inouye Academic Press, p. 83, 1983, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. In an illustrative embodiment, an ATR activation domain polypeptide is produced recombinantly utilizing an expression vector generated by sub-cloning the coding sequence of the polypeptide.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning A Laboratory Manual, 2nd Ed., ed. by Sambrook, Fritsch and Maniatis (Cold Spring Harbor Laboratory Press: 1989) Chapters 16 and 17.

In some instances, it may be desirable to express the subject recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

When it is desirable to express only a portion of a protein, such as a form lacking a portion of the N-terminus, i.e. a truncation mutant which lacks the signal peptide, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol. 169: 751-757, 1987) and *Salmonella typhimurium* and its in vitro activity has been demonstrated on recombinant proteins (Miller et al., PNAS 84: 2718-1722, 1987). Therefore, removal of an N-terminal methionine, if desired, can be achieved either in vivo or in vitro.

Alternatively, the coding sequences for the polypeptide can be incorporated as a part of a fusion gene including a nucleotide sequence encoding a different polypeptide. This type of expression system can be useful under conditions where it is desirable to produce an immunogenic fragment of a protein. For example, the VP6 capsid protein of rotavirus can be used as an immunologic carrier protein for portions of the polypeptide, either in the monomeric form or in the form of a viral particle.

In addition to utilizing fusion proteins to enhance immunogenicity, it is widely appreciated that fusion proteins can also facilitate the expression, purification, and/or detection of proteins. For example, polypeptides can be generated as glutathione-S-transferase (GST-fusion) proteins. Such GST-fusion proteins can enable easy purification of a polypeptide, as for example by the use of glutathione-derivatized matrices (see, for example, Current Protocols in Molecular Biology, eds. Ausubel et al. (N.Y.: John Wiley & Sons, 1991)). In another embodiment, a fusion gene coding for a purification leader sequence, such as a poly-(His)/enterokinase cleavage site sequence, can be used to replace the signal sequence which naturally occurs at the N-terminus of the protein (e.g., of the pro-form, in order to permit purification of the poly(His)-proteinX protein by affinity chromatography using a $Ni^{2+}$ metal resin. The purification leader sequence can then be subsequently removed by treatment with enterokinase (e.g., see Hochuli et al., J. Chromatography 411: 177, 1987; and Janknecht et al. PNAS 88: 8972).

Techniques for making fusion genes are known to those skilled in the art. Essentially, the joining of various nucleic acid fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, Current Protocols in Molecular Biology, eds. Ausubel et al. John Wiley & Sons: 1992).

The present invention also makes available isolated polypeptides which are isolated from, or otherwise substantially free of other cellular and extracellular proteins. The term "substantially free of other cellular or extracellular proteins" (also referred to herein as "contaminating proteins") or "substantially pure or purified preparations" are defined as encompassing preparations having less than 20% (by dry weight) contaminating protein, and preferably having less than 5% contaminating protein. Functional forms of the subject polypeptides can be prepared, for the first time, as purified preparations by using a cloned gene as described herein. By "purified," it is meant, when referring to a peptide or nucleic acid sequences, that the indicated molecule is present in the substantial absence of other biological macromolecules, such as other proteins. The term "purified" as used herein preferably means at least 80% by dry weight, more preferably in the range of 95-99% by weight, and most preferably at least 99.8% by weight, of biological macromolecules of the same type present (but water, buffers, and other small molecules, especially molecules having a molecular weight of less than 5000, can be present). The term "pure" as used herein preferably has the same numerical limits as "purified" immediately above. "Isolated" arid "purified" do not encompass either natural materials in their native state or natural materials that have been separated into components (e.g., in an acrylamide gel) but not obtained either as pure (e.g. lacking contaminating proteins, or chromatography reagents such as denaturing agents and polymers, e.g. acrylamide or agarose) substances or solutions.

Isolated peptidyl portions of proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry.

The recombinant polypeptides of the present invention also include versions of those protein which are resistant to proteolytic cleavage, as for example, due to mutations which alter potential cleavage sequences or which inactivate an enzymatic activity associated with the protein. Variants of the present invention also include proteins which have been post-translationally modified in a manner different than the authentic protein.

Modification of the structure of the subject polypeptides can be for such purposes as enhancing therapeutic or prophylactic efficacy, or stability (e.g., ex vivo shelf life and resistance to proteolytic degradation in vivo). Such modified peptides, when designed to retain at least one activity of the naturally-occurring form of the protein, are considered functional equivalents of the polypeptides described in more detail herein. Such modified peptides can be produced, for instance, by amino acid substitution, deletion, or addition.

For example, it is reasonable to expect that an isolated replacement of a leucine with an isoleucine or valine, an aspartate with a glutamate, a threonine with a serine, or a similar replacement of an amino acid with a structurally related amino acid (i.e. isosteric and/or isoelectric mutations) will not have a major effect on the biological activity of the resulting molecule. Conservative replacements are those that take place within a family of amino acids that are related in their side chains. Genetically encoded amino acids can be divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan, and tyrosine are sometimes classified jointly as aromatic amino acids. In similar fashion, the amino acid repertoire can be grouped as (1) acidic=aspartate, glutamate; (2) basic=lysine, arginine histidine, (3) aliphatic=glycine, alanine, valine, leucine, isoleucine, serine, threonine, with serine and threonine optionally be grouped separately as aliphatic-hydroxyl; (4) aromatic=phenylalanine, tyrosine, tryptophan; (5) amide=asparagine, glutamine; and (6) sulfur-containing=cysteine and methionine. (see, for example, Biochemistry, 2nd ed., Ed. by L. Stryer, W H Freeman and Co.: 1981). Whether a change in the amino acid sequence of a peptide results in a functional variant (e.g. functional in the sense that it acts to mimic or antagonize the wild-type form) can be readily determined by assessing the ability of the variant peptide to produce a response in cells in a fashion similar to the wild-type protein, or competitively inhibit such a response. Polypeptides in which more than one replacement has taken place can readily be tested in the same manner.

This invention further contemplates a method for generating sets of combinatorial mutants of the subject proteins as well as truncation mutants, and is especially useful for identifying potential variant sequences that maintain at least one function (activity) of a wildtype polypeptide. The purpose of screening such combinatorial libraries is to generate, for example, novel variants which can act as either agonists or antagonists, or alternatively, possess novel activities all together. To illustrate, variant polypeptides of the ATR activation domain of TopBP1 can be engineered by the present method to provide proteins that activates at least one function of ATR (e.g., phosphorylation of Chk1 proteins, binding for single-stranded or double-stranded DNA). Combinatorially-derived variants can also be generated to have an increased potency relative to a naturally occurring form of the protein.

Likewise, dominant negative variants can also be generated by the present combinatorial approach to act as antagonists of ATR activation.

In one aspect of this method, the amino acid sequences for a population of ATR activation domains (for examples human, mouse, and *Xenopus* ATR activation domains of TopBP1) or other related proteins may be aligned, preferably to promote the highest homology possible. Amino acids which appear at each position of the aligned sequences are selected to create a degenerate set of combinatorial sequences. In a preferred embodiment, the variegated library of variants is generated by combinatorial mutagenesis at the nucleic acid level, and is encoded by a variegated gene library. For instance, a mixture of synthetic oligonucleotides can be enzymatically ligated into gene sequences such that the degenerate set of potential sequences are expressible as individual polypeptides, or alternatively, as a set of larger fusion proteins (e.g. for phage display) containing the set of sequences therein.

There are many ways by which the library of potential variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential variant sequences. The synthesis of degenerate oligonucleotides is well known in the art (see for example, Narang, Tetrahedron 39: 3, 1983; Itakura et al., Recombinant DNA, Proc 3rd Cleveland Sympos. Macromolecules, ed. A G Walton, Amsterdam: Elsevier pp 273-289, 1981; Itakura et al., Annu. Rev. Biochem. 53: 323, 1984; Itakura et al., Science 198: 1056, 1984; Ike et al., Nucleic Acid Res. 11: 477, 1983. Such techniques have been employed in the directed evolution of other proteins (see, for example, Scott et al., Science 249: 386-390, 1990; Roberts et al., PNAS 89: 2429-2433, 1992; Devlin et al., Science 249: 404-406, 1990; Cwirla et al., PNAS 87: 6378-6382, 1990; as well as U.S. Pat. Nos. 5,223, 409, 5,198,346, and 5,096,815).

A wide range of techniques are known in the art for screening gene products of combinatorial libraries made by point mutations, and for screening cDNA libraries for gene products having a certain property. Such techniques will be generally adaptable for rapid screening of the gene libraries generated by the combinatorial mutagenesis of the subject variants. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described herein are amenable to high through-put analysis as necessary to screen large numbers of sequences created by combinatorial mutagenesis techniques.

(vii) Methods of Administration of Proteins, Chemical Compounds and Pharmaceutical Compositions of Any Agent The one or more modulators identified by the subject methods may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the one or more agents. The use of such media for pharmaceutically active substances is known in the art. Except insofar as any conventional media or agent is incompatible with the activity of a particular agent or combination of agents, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "deposit formulations."

Methods of introduction may also be provided by rechargeable or biodegradable devices. Various slow release polymeric devices have been developed and tested in vivo in recent years for the controlled delivery of drugs, including proteinacious biopharmaceuticals. A variety of biocom-patible polymers (including hydrogels), including both biodegradable and non-degradable polymers, can be used to form an implant for the sustained release of an agent at a particular target site.

Depending on the specific modulators in question, the subject modulators identified using the methods of the present invention may be given orally, parenterally, topically, or rectally. They are of course given by forms suitable for each administration route. For example, they are administered in tablets or capsule form, by injection, inhalation, eye lotion, ointment, suppository, controlled release patch, or infusion.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the animal's system and, thus, is subject to metabolism and other like processes, for example, subcutaneous administration.

One or more agents may be administered to humans and other animals by any suitable route of administration, including orally, nasally, as by, for example, a spray, rectally, intravaginally, parenterally, intracisternally and topically, as by powders, ointments or drops, including buccally and sublingually.

Actual dosage levels of the one or more agents administered in the methods of the present invention may be varied so as to obtain an amount of the active ingredient which is effective to achieve a response in an animal. The actual effective amount can be determined by one of skill in the art using routine experimentation and may vary by mode of administration. Further, the effective amount may vary according to a variety of factors include the size, age and gender of the individual being treated. Additionally, the severity of the condition being treated, as well as the presence or absence of other components to the individuals treatment regimen will influence the actual dosage.

The effective amount or dosage level will depend upon a variety of factors including the activity of the particular one or more agents employed, the route of administration, the time of administration, the rate of excretion of the particular agents being employed, the duration of the treatment, other drugs, compounds and/or materials used in combination with the particular agents employed, the age, sex, weight, condition, general health and prior medical history of the animal, and like factors well known in the medical arts.

The one or more modulators identified by the methods of the present invention can be administered as such or in admixtures with pharmaceutically acceptable and/or sterile carriers, and can also be administered in conjunction with other compounds. Such additional compounds may include factors known to influence the proliferation, differentiation or migration of a particular cell. These additional compounds may be administered sequentially to or simultaneously with the compounds being screened by the methods of the present invention. By administering compounds known to influence cell behavior, the invention further contemplates identifying modulators which may not alone be sufficient to influence cell behavior. However, such modulators may be capable of acting additively or synergistically with compounds known to modulate cell behavior.

Modulators screened by the methods of the present invention can be administered alone, or can be administered as a pharmaceutical formulation (composition). The modulators may be formulated for administration in any convenient way for use in human or veterinary medicine. In certain embodiments, the modulators included in the pharmaceutical preparation may be active themselves, or may be a prodrug, e.g., capable of being converted to an active compound in a physiological setting.

Thus, another aspect of the present invention provides pharmaceutically acceptable compositions comprising an effective amount of one or more modulators, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject agents may be simply dissolved or suspended in sterile water. In certain embodiments, the pharmaceutical preparation is non-pyrogenic, i.e., does not elevate the body temperature of a patient.

The phrase "effective amount" as used herein means that amount of one or more agent, material, or composition comprising one or more agents of the present invention which is effective for producing some desired effect in an animal.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body.

Each carrier must be "acceptable" in the sense of being compatible with the other ingredients of the formulation. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, one or more agents may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See, for example, Berge et al., "Pharmaceutical Salts," J. Pharm. Sci. 66:1-19, 1997).

The pharmaceutically acceptable salts of the modulators include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the one or more modulators may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in-situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al., supra. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent with the carrier and, optionally, one or more accessory ingredients. In general, the formulations are prepared by uniformly and intimately bringing into association an agent of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate; with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as $\alpha$-, $\beta$- and $\gamma$-cyclodextrin, dimethyl-$\beta$cyclodextrin and 2-hydroxypropyl-$\beta$f-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the agents.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the agents in the proper medium. Absorption enhancers can also be used to increase the flux of the agents across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of an agent, it is desirable to slow the absorption of the agent from subcutaneous or intramuscular injection. This may be accomplished by the use of a liquid suspension of crystalline or amorphous material having poor water solubility. The rate of absorption of the agent then depends upon its rate of dissolution which, in turn, may depend upon crystal size and crystalline form. Alternatively, delayed absorption of a parenterally administered agent form is accomplished by dissolving or suspending the agent in an oil vehicle.

Injectable depot forms are made by forming microencapsule matrices of the subject compounds in biodegradable polymers such as polylactide-polyglycolide. Depending on the ratio of agent to polymer, and the nature of the particular polymer employed, the rate of agent release can be controlled. Examples of other biodegradable polymers include poly (orthoesters) and poly(anhydrides). Depot injectable formulations are also prepared by entrapping the agent in liposomes or microemulsions which are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W. H. Freedman and C O., San Francisco, U.S.A., 1969 or "Livestock Feeds and Feeding" O and B books, Corvallis, Oreg., U.S.A., 1977).

EXAMPLES

The general concept of the invention having been described, the section below provides several working examples to further illustrate several exemplary (but non-limiting) embodiments of the instant invention.

Example I

Recombinant XtopBP1 Induces a Large Increase in the Kinase Activity of Xatr

Applicants have shown that Xatr undergoes a substantial increase in kinase activity in response to checkpoint-inducing DNA templates in *Xenopus* egg extracts (Guo et al., 2000; Kumagai et al., 2004). These data demonstrated that Xatr undergoes activation upon interaction with DNA or a DNA-associating protein(s) or both.

Here, Applicants demonstrate that XtopBP1 plays a direct role in the Xatr activation process. Specifically, Applicants first isolated Xatr from egg extracts by pull-downs with FLAG-tagged *Xenopus* ATRIP (Xatrip). For these experiments, Applicants used both full-length Xatrip and an N-terminal truncation mutant (ΔN222) that supports normal Xatr-dependent activation of Xchk1 in egg extracts (Kumagai et al., 2004; Kim et al., 2005).

As shown in FIG. 1A, Xatr bound well to beads containing either wild-type or ΔN222 Xatrip, but not to control beads lacking Xatrip. Applicants eluted the beads with FLAG peptide and mixed the eluates with a His6-tagged version of XtopBP1 that had been purified from baculovirus-infected insect cells (FIG. 1B). Finally, Applicants added $^{32}$P-ATP and PHAS-I, a commonly used model substrate for ATR (Abraham, 2001).

As shown in FIG. 1C, addition of XtopBP1 induced a very large increase in the kinase activity of both Xatr-Xatrip complexes toward PHAS-I. The Xatr-Xatrip preparations themselves exhibited relatively low kinase activity under these conditions. In addition, the preparation of recombinant XtopBP1 alone contained negligible kinase activity toward PHAS-I.

In a dose-response analysis, Applicants observed that half-maximal induction of kinase activity occurred at approximately 10-15 μg/ml XtopBP1 (FIGS. 1D and E). For comparison, the endogenous concentration of XtopBP1 in egg extracts is about 5 μg/ml (Hashimoto and Takisawa, 2003).

In order to establish the specificity of the assay, Applicants carried out similar experiments with egg extracts lacking Xatr. For this purpose, Applicants removed Xatr from the extracts by immunodepletion with anti-Xatr antibodies. In parallel, Applicants prepared mock-depleted extracts with control antibodies. Next, Applicants incubated recombinant XatripΔN222-FLAG in mock-depleted and Xatr-depleted extracts in the presence of anti-FLAG beads. Applicants reisolated the beads, eluted with FLAG peptide, added His6-XtopBP1, and assayed kinase activity toward PHAS-I.

Figure 2:
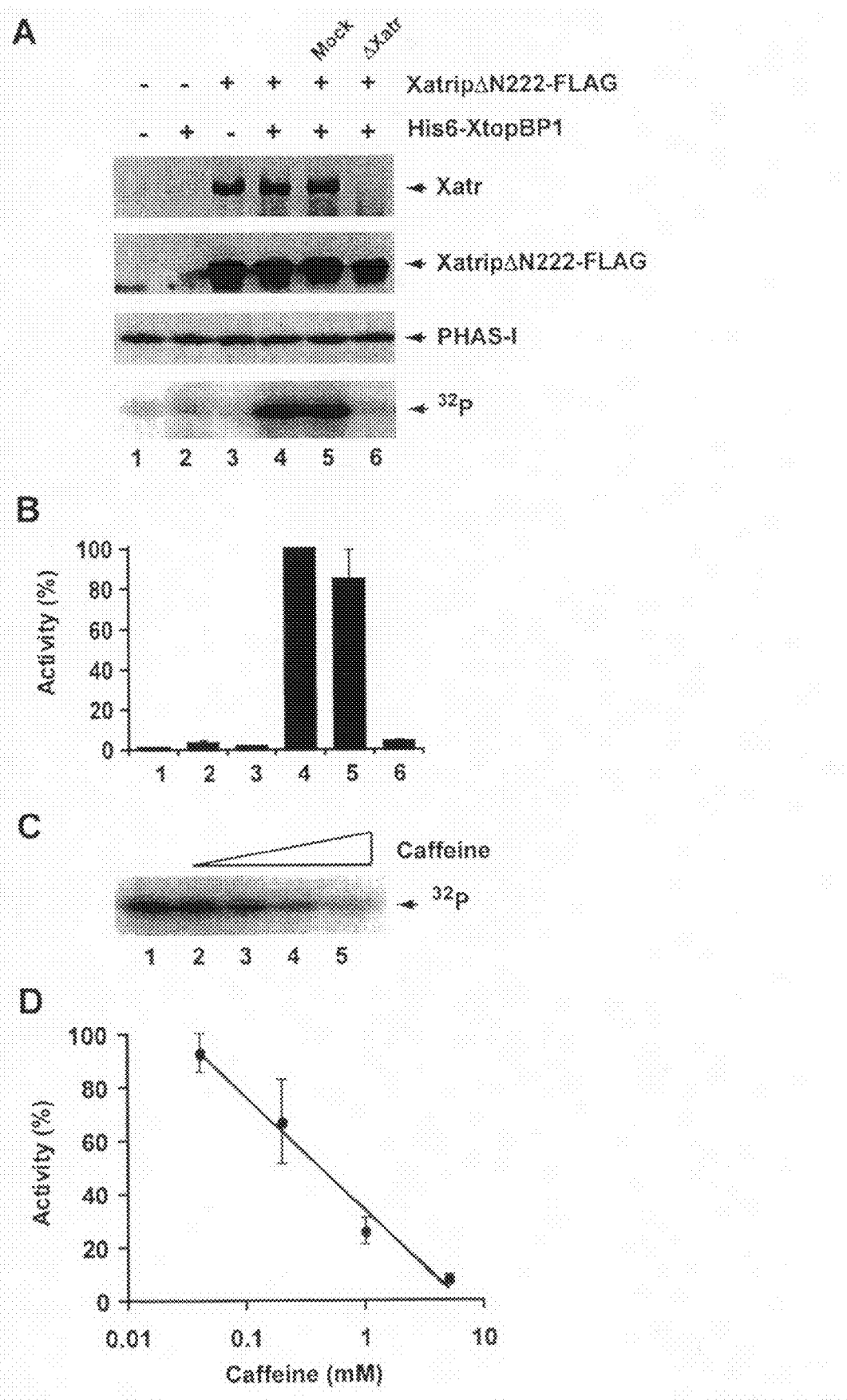
FIGS. 2A-2D show that XtopBP1-induced kinase activity of Xatr-XatripΔN222-FLAG complex is due to Xatr.

As expected, Xatr was present in the preparation from mock-depleted but not from Xatr-depleted extracts (FIG. 2A). Applicants observed that His6-XtopBP1 could not elicit any kinase activity toward PHAS-I in the preparation from Xatr-depleted extracts (FIGS. 2A and B). By contrast, consistent with the results described above, His6-XtopBP1 induced strong kinase activity in the preparation from mock-depleted extracts. These findings indicate that the induced kinase activity is due to Xatr.

Applicants also characterized the sensitivity of the XtopBP1-activated form of Xatr to caffeine, a documented inhibitor of ATR in numerous organisms (Abraham, 2001). As shown in FIGS. 2C and D, caffeine inhibited the activated form of Xatr very effectively, with half-maximal inhibition occurring at approximately 0.4 mM. This concentration is comparable to that previously reported for inhibition of both human and *Xenopus* ATR (Sarkaria et al., 1999; Guo et al., 2000).

Example II

The Xatr-Activating Function of XtopBP1 Resides in a Discrete C-Terminal Domain Applicants performed structure-function studies in order to identify which part of XtopBP1 is responsible for the activation of Xatr. For this purpose, Applicants produced a series of overlapping GST fusion proteins containing approximately 300-350 amino acids from XtopBP1. Both human TopBP1 and XtopBP1 are relatively large proteins that contain approximately 1500 amino acids. XtopBP1, like human TopBP1, has been reported to contain eight BRCT repeats (Yamane et al., 1997; Van Hatten et al., 2002; Hashimoto and Takisawa, 2003). Four expression constructs were designed to contain two adjoining BRCT repeats each (e.g., residues 1-348, 333-646, 623-984, and 1197-1513) as designated in FIG. 3A. In addition, Applicants also prepared a GST fusion protein containing a conserved region between BRCT domains VI and VII (residues 972-1279).

Figure 3:
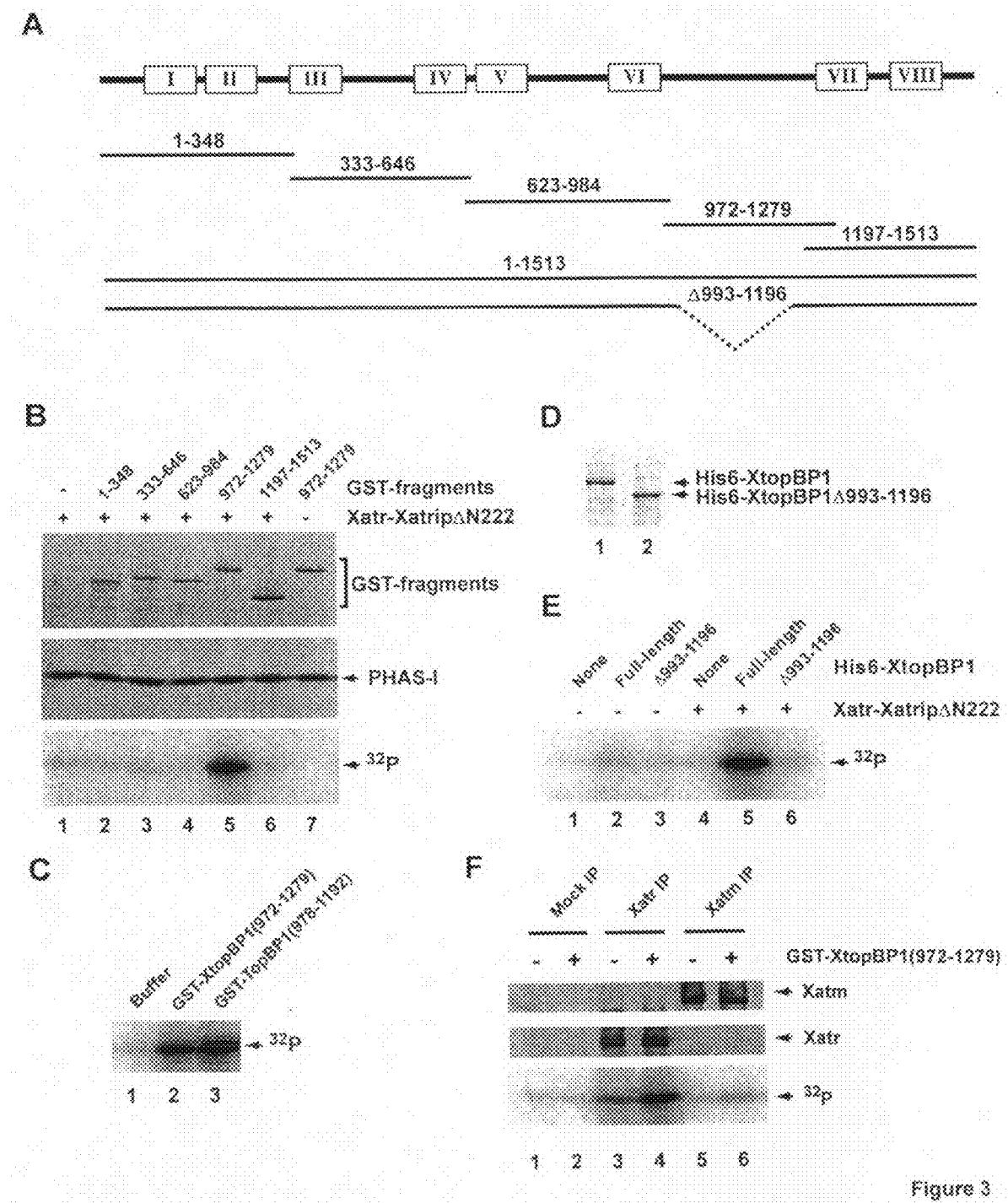
FIGS. 3A-3F show mapping of the ATR-activating domain from XtopBP1.

Upon incubation with Xatr-Xatrip, Applicants observed that the 972-1279 peptide induced activation of Xatr as effectively as full-length XtopBP1 (FIG. 3B). By contrast, none of the BRCT-containing fusion proteins had any effect on the activity of Xatr. Applicants also found that a similar fragment of human TopBP1 (residues 978-1192) from between BRCT domains VI and VII likewise activated Xatr-Xatrip very effectively (FIG. 3C). Therefore, the ATR-activating function is conserved in both *Xenopus* and human TopBP1.

In order to pursue these observations further, Applicants produced a full-length version of XtopBP1 in which most of the ATR-activating domain had been deleted (the Δ993-1196 mutant) (FIG. 3D). In contrast to the full-length protein, the XtopBP1Δ993-1196 mutant protein displayed no Xatr-activating capacity (FIG. 3E). Therefore, a conserved segment of XtopBP1 between BRCT domains VI and VII appears to be both necessary and sufficient for activation of Xatr.

Example III

XtopBP1 Increases the Kinase Activity of Xatr Toward Numerous Substrates but Has No Effect on Xatm Applicants also examined two documented physiological substrates of Xatr, namely *Xenopus* Mcm2 (Xmcm2) and Xchk1 (Guo et al., 2000; Zhao and Piwnica-Worms, 2001; Cortez et al., 2004; Yoo et al., 2004). For Xmcm2, Applicants used the GST-Xmcm2 (62-122) fusion peptide, in which S92 is a target for Xatr (Yoo et al., 2004). In the case of Xchk1, Applicants used both the whole protein (Xchk1-Myc-His6) and a GST fusion peptide from its regulatory domain (residues 306-352) that contains S344, the major phosphorylation site for Xatr (Guo et al., 2000; Liu et al., 2000).

For these experiments, Applicants used the GST-XtopBP1 (972-1279) fragment as the activator of Xatr. Applicants found that the XtopBP1 fragment induced a strong Xatr-dependent phosphorylation of the GST-Xmcm2 (62-122) peptide (FIG. 8). This phosphorylation occurred on S92, because there was no $^{32}$P incorporation into the S92A mutant of this peptide. Similarly, Applicants observed that the XtopBP1 fragment readily induced phosphorylation of both the GST-Xchk1 (306-352) peptide and full-length Xchk1-Myc-His6 on S344 (FIG. 8).

These experiments establish that XtopBP1 strongly stimulates the ability of Xatr to phosphorylate a variety of different substrates. Furthermore, these results imply that the increased phosphorylation is due to elevated kinase activity rather than XtopBP1-mediated tethering of Xatr to substrates, because Applicants have observed this effect with two different small peptides approximately 50-60 residues in length, as well as a model substrate protein (PHAS-I). It seems implausible that all of these substrates could be using XtopBP1 as an adaptor protein. However, these observations do not rule out the possibility that TopBP1 could play an additional role in recognition of intact physiological substrates apart from the process that Applicants have characterized herein.

Applicants have also shown that TopBP1 is a specific activator of ATR and not a general activator of the PIKK family.

Specifically, Applicants immunoprecipitated both Xatr and Xatm in parallel from *Xenopus* egg extracts and then incubated the immunoprecipitates with GST-XtopBP1 (972-1279) (FIG. 3F). Consistent with the results described above, Applicants observed strong activation of immunoprecipitated Xatr by this method. By contrast, there was no activation of Xatm in the presence of the GST-XtopBP1 (972-1279) peptide.

Example IV

XtopBP1 Associates with Xatr in a Manner that Depends Upon Xatrip

Applicants have also demonstrated that XtopBP1 activates Xatr by associating physically with Xatr.

Figure 4:
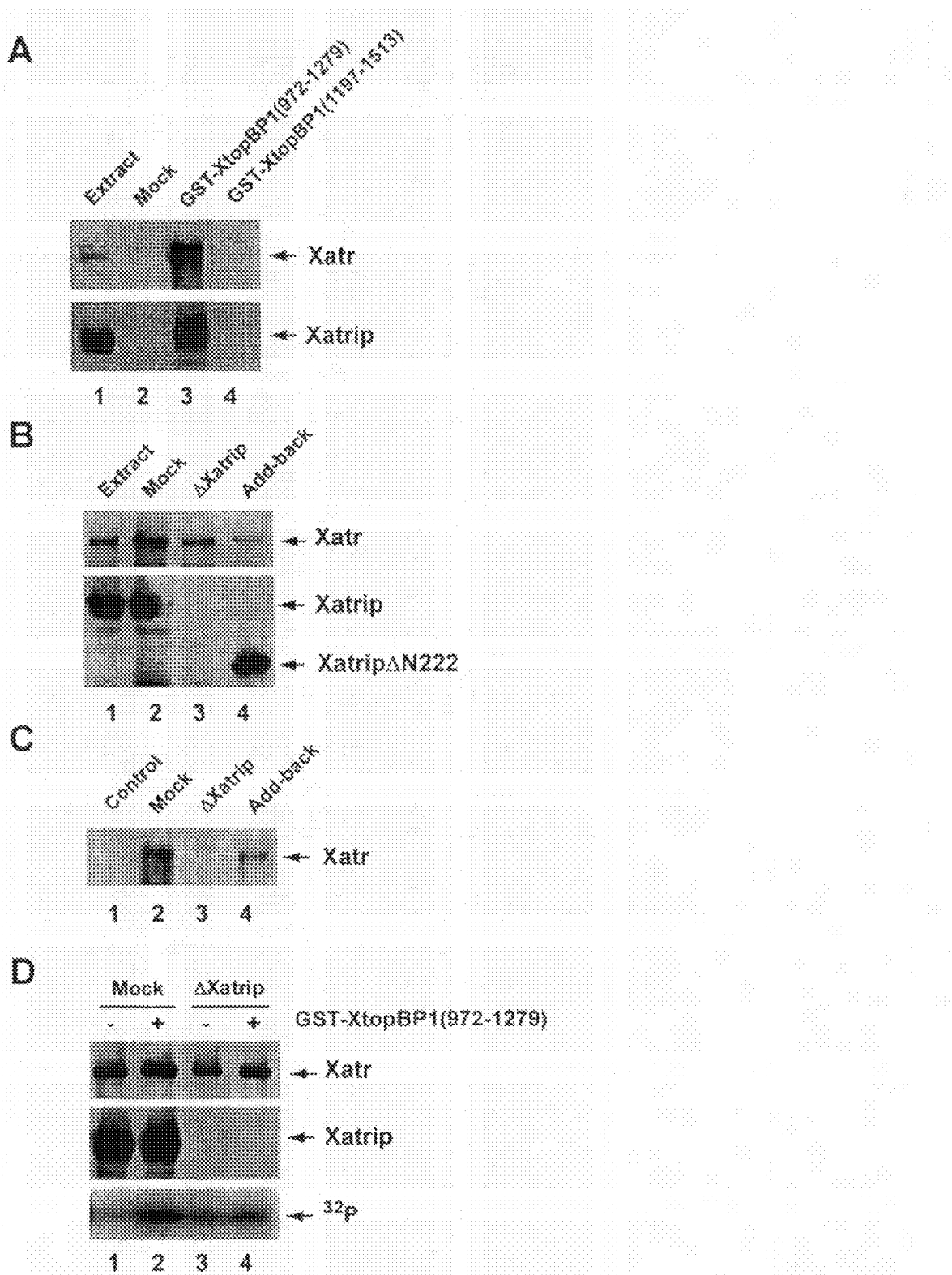
FIGS. 4A-4D show that XtopBP1 associates with Xatr in a manner that depends on Xatrip.

Specifically, Applicants incubated glutathione beads containing GST-XtopBP1 (972-1279) in egg extracts, reisolated the beads, and performed immunoblotting for both Xatr and Xatrip. As shown in FIG. 4A, Applicants could clearly detect binding of both Xatr and Xatrip to beads containing GST-XtopBP1 (972-1279). Conversely, there was no binding of Xatr or Xatrip to glutathione beads containing either no GST fusion protein or the GST-XtopBP1 (1197-1513) fragment, which is incapable of activating Xatr. In addition, in other experiments, there was no binding of Xatr or Xatrip to beads containing GST fusions of the 1-348, 333-646, or 623-984 segments from XtopBP1 (data not shown).

Applicants also tested to see if the association of XtopBP1 with Xatr depends upon Xatrip. For this experiment, Applicants removed endogenous Xatrip from egg extracts by immunodepletion with anti-Xatrip antibodies. As described previously, this procedure leaves behind approximately 30% of the endogenous Xatr, the fraction that is not in a complex with Xatrip (Kumagai et al., 2004). Next, Applicants added GST-XtopBP1 (972-1279) to the Xatrip-depleted extracts and to mock-depleted extracts that had been prepared in parallel.

As shown in FIGS. 4B and C, Applicants observed no binding of Xatr to the XtopBP1 fragment in Xatrip-depleted extracts, whereas there was good binding in mock-depleted extracts. Furthermore, Applicants could restore the binding of Xatr to the XtopBP1 fragment by addition of recombinant XatripΔN222-FLAG to the Xatrip-depleted extracts. These results indicate that XtopBP1 depends upon the presence of Xatrip in order to associate with Xatr-Xatrip.

Applicants further tested whether activation of Xatr by XtopBP1 depends on Xatrip. As shown in FIG. 4D, treatment with XtopBP1 could not significantly increase the kinase activity of Xatr that had been immunoprecipitated from Xatrip-depleted extracts. Notably, it has been established that binding of ATRIP to ATR is necessary for checkpoint-dependent phosphorylation of Chk1 in both human cells and *Xenopus* egg extracts (Falck et al., 2005; Kim et al., 2005). This observation suggests a failure of TopBP1 to activate ATR in the absence of ATRIP.

Example V

Figure 5:
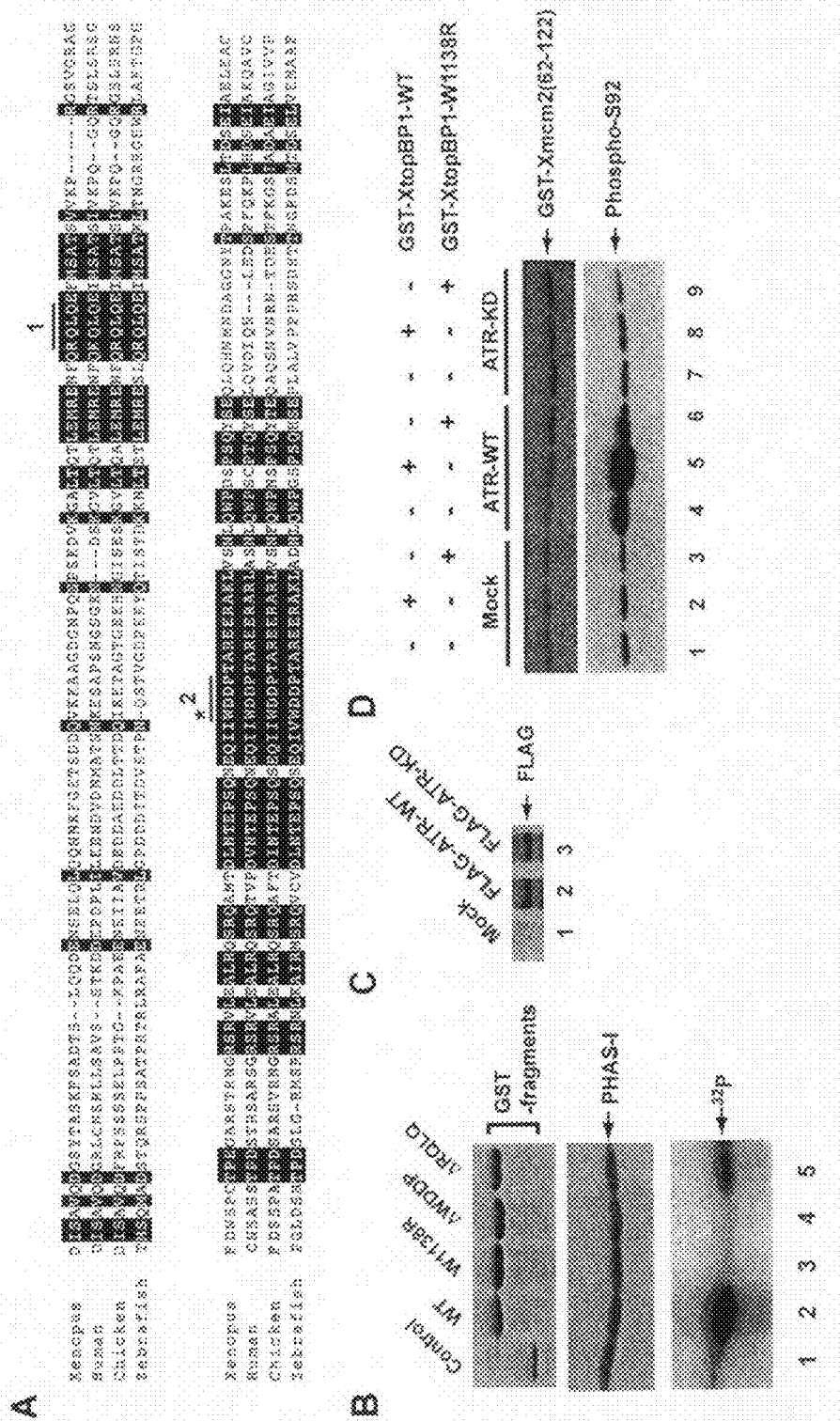
FIGS. 5A-5D show identification of a point mutant in the ATR-activating domain and activation of recombinant human ATR.

Identification of a Point Mutant of XtopBP1 that Is Defective for Activation of Xatr As shown in FIG. 5A, the ATR-activating domain of XtopBP1 is well conserved in other vertebrates, including humans, chickens, and zebrafish. In order to explore which aspects of this region were important for the activation of Xatr, Applicants first prepared some deletions of highly conserved segments (e.g., RQLQ (SEQ ID NO: 1) and WDDP (SEQ ID NO: 2)) in the context of the GST-XtopBP1 (972-1279) fragment. Applicants found that the ΔRQLQ mutant was very strongly compromised in its ability to induce the activation of Xatr, while the ΔWDDP mutant was virtually inactive (FIG. 5B).

Figure 9:
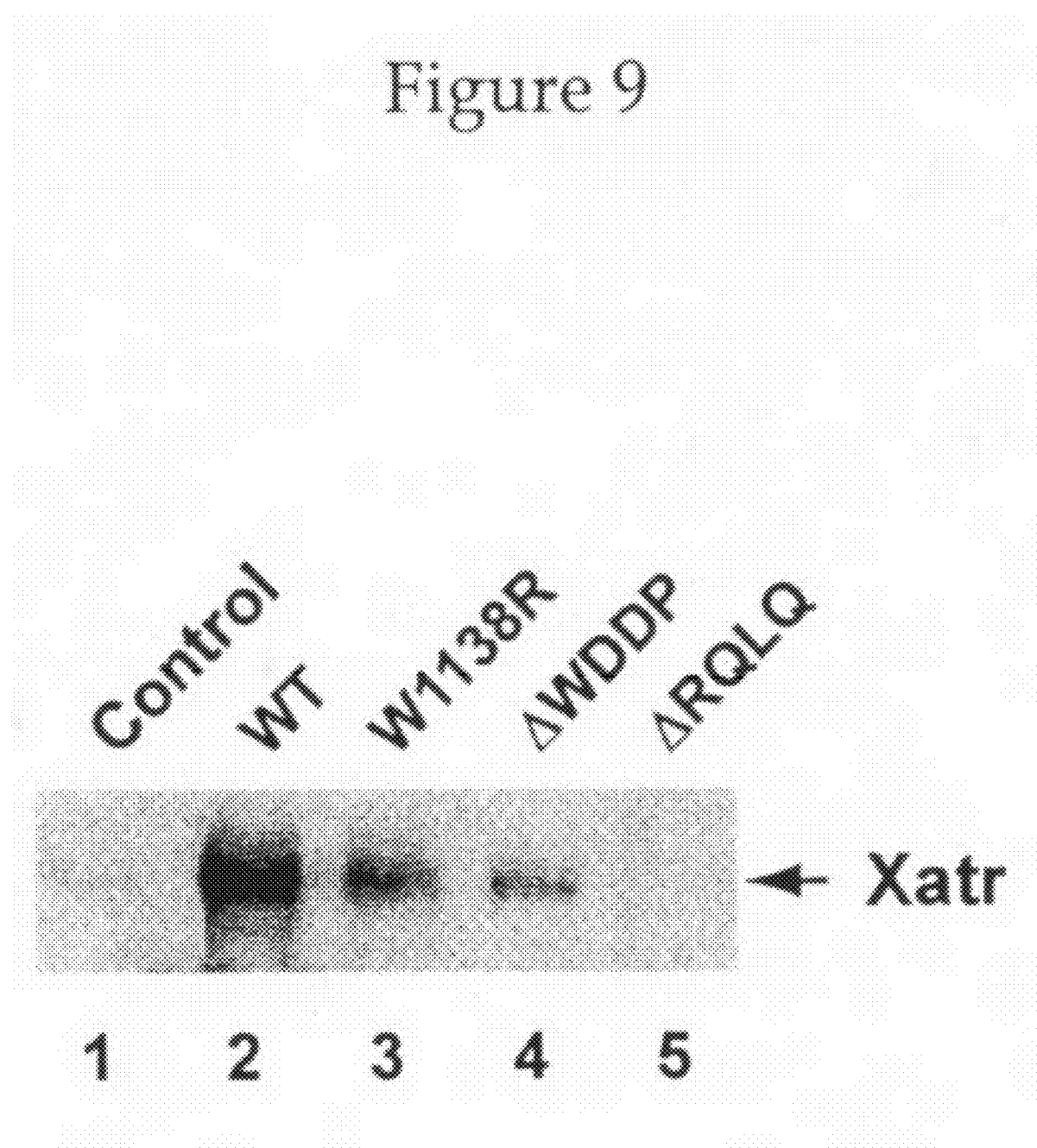
FIG. 9 shows properties of ATR-activating domain mutants for interaction with Xatr-Xatrip. Egg extracts were incubated with GST-XtopBP1 (1197-1513) (lane 1) or the wild-type (lane 2), W1138R (lane 3), ΔWDDP (lane 4), or ΔRQLQ (lane 5) versions of GST-XtopBP1 (972-1279). Extracts were filtered through a G25 Sephadex column to remove endogenous glutathione and incubated with glutathione agarose beads. The beads were isolated and immunoblotted for Xatr.

Applicants then generated a point mutant (W1138R), in which the tryptophan in the WDDP motif was changed to arginine. Applicants observed that W1138R mutant of GST-XtopBP1 (972-1279) had totally lost its capacity to induce the activation of Xatr (FIG. 5B). Interestingly, the W1138R mutant retains significant ability to bind Xatr-Xatrip (FIG. 9).

Example VI

TopBP1 Induces Activation of Wild-type but Not Kinase-Deficient Recombinant Human ATR Applicants also demonstrated that TopBP1 induces activation of recombinant human ATR. Specifically, Applicants isolated wild-type and kinase-deficient versions of FLAG-tagged human ATR from nuclear extracts of U2OS cells that conditionally express these proteins (FIG. 5C). The recombinant ATR proteins were purified with anti-FLAG magnetic beads under conditions that preserve the binding of endogenous ATRIP (Ünsal-Kacmaz and Sancar, 2004). Next, Applicants incubated both the wild-type and kinase-deficient FLAG-ATR preparations in the absence or presence of GST-XtopBP1 (972-1279), and measured kinase activity against S92 of the GST-Xmcm2 (62-122) peptide. Applicants also tested the inactive W1138R mutant of the XtopBP1 fragment.

As depicted in FIG. 5D, GST-XtopBP1 (972-1279) induced a large increase in the kinase activity of wild-type FLAG-ATR. By contrast, the W1138R mutant did not induce any activation of wild-type ATR. As another control, Applicants also showed that GST-XtopBP1 (972-1279) did not induce any kinase activity in a mock preparation of magnetic beads (lacking anti-FLAG antibodies) that was prepared from cells expressing wild-type FLAG-ATR. Finally, under the same assay conditions, Applicants found that neither the intact nor W1138R mutant form of GST-XtopBP1 (972-1279) had any effect on the activity of kinase-deficient FLAG-ATR (FIG. 5D).

These results establish that TopBP1 can activate both *Xenopus* and human ATR. Furthermore, these experiments provide conclusive evidence that the kinase activity that is induced by TopBP1 is intrinsic to the ATR protein itself, and is not due to a kinase that associates with ATR.

Example VII

Figure 6:
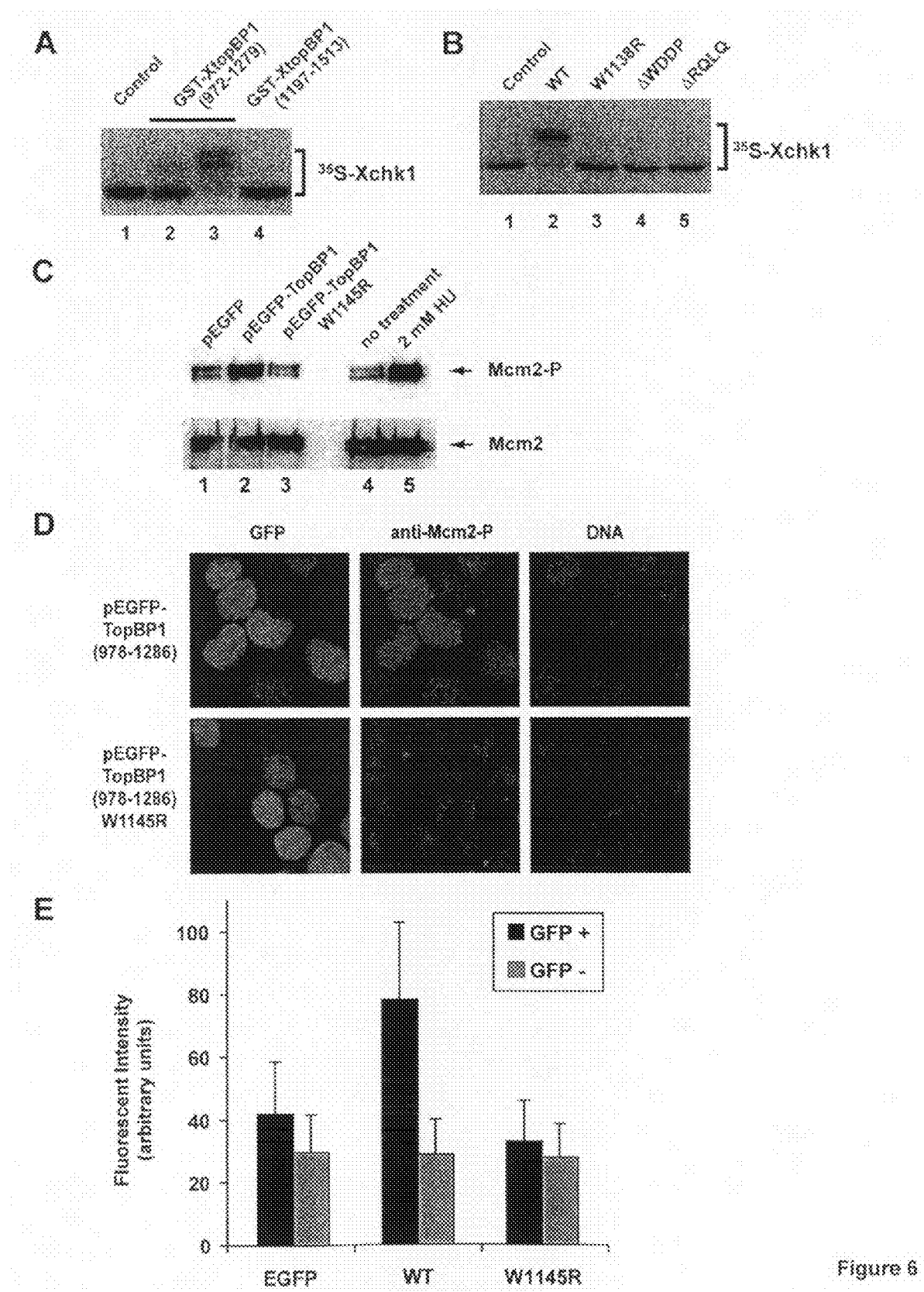
FIGS. 6A-6E show that the isolated ATR-activating domain of TopB1 induces ectopic phosphorylation of downstream targets of ATR.

The ATR-Activating Domain of TopBP1 Can Trigger Ectopic Phosphorylation of Downstream Targets of ATR Because the GST-XtopBP1 (972-1279) fragment could activate Xatr in vitro without the inclusion of DNA, Applicants reasoned that ectopic addition of this fragment to *Xenopus* egg extracts might also be able to trigger the Xatr-dependent phosphorylation of Xchk1 even in the absence of a checkpoint-inducing DNA template. To prove this, Applicants incubated egg extracts with increasing amounts of GST-XtopBP1 (972-1279) in the presence of $^{35}$S-labeled Xchk1 and tautomycin (to inhibit cytoplasmic phosphatases) (Kumagai and Dunphy, 2000). As shown in FIG. 6A, the 972-1279 fragment could elicit a very robust phosphorylation of Xchk1, as indicated by a decrease in electrophoretic mobility. By contrast, the GST-XtopBP1 (1197-1513) fragment, which does not activate Xatr, did not induce any phosphorylation of Xchk1 in egg extracts. Furthermore, none of the ΔRQLQ, ΔWDDP, or W1138R mutants of the 972-1279 fragment could induce ectopic activation of Xchk1 in these extracts (FIG. 6B).

Figure 10:
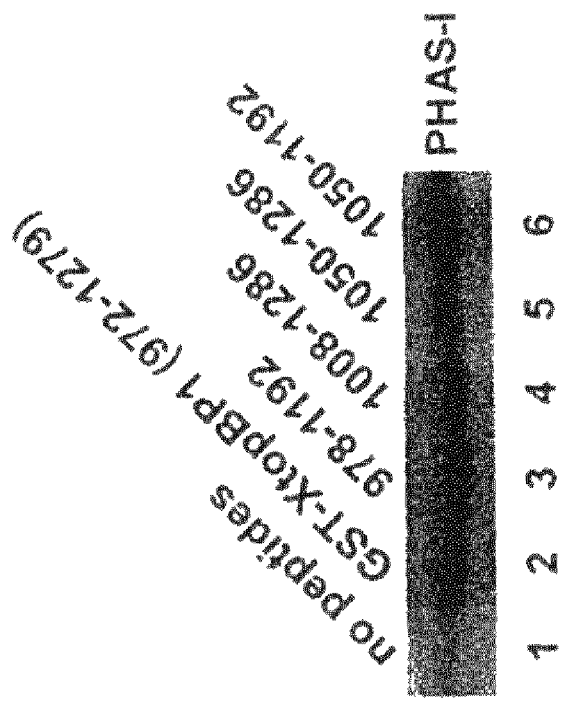
FIG. 10 shows the mapping of the minimal ATR activation domain in TopBP1. Xatr-XatripΔ222 was incubated in the presence of GST-XtopBP1 (972-1279) (Lane 2), various His6-Human TopBP1 fragments (Lanes 3-6), or no peptides (Lane 1) in kinase buffer containing [$^{32}$P]ATP and PHAS-I. Reaction were subjected to SDS-PAGE analysis.

Applicants have also narrowed down the minimal domain required for ATR activation. FIG. 10 shows the mapping of the minimal ATR activation domain in TopBP1. Specifically, Xatr-XatripΔ222 was incubated in the presence of GST-XtopBP1 (972-1279) (Lane 2), various His6-Human TopBP1 fragments (Lanes 3-6), or no peptides (Lane 1) in kinase buffer containing [$^{32}$P]ATP and PHAS-I. Reactions were subjected to SDS-PAGE analysis.

The results showed that the fragment containing residues 978-1192 and the fragment containing residues 1050-1192 are almost as effective as the 972-1279 fragment in terms of ATR activation. There might be a slight, but not very significant reduction in ATR activation if the 1008-1286 fragment was used. In contrast, a significant reduction in ATR activation was observed if the 1050-1286 fragment was used. These results suggest that at least the 1050-1192 fragment of the ATR activation domain is as efficient an ATR activator as the 972-1279 fragment.

To pursue this issue further, Applicants asked whether the ATR-activating domain of TopBP1 could induce ATR-dependent phosphorylation in human cells. For this purpose, Applicants constructed a version of the enhanced green fluorescent protein (EGFP) containing the SV40 nuclear localization sequence and residues 978-1286 of human TopBP1 (equivalent to residues 972-1279 of XtopBP1). Applicants also produced the W1145R mutant of this plasmid (analogous to the W1138R mutant of XtopBP1). Applicants transfected plasmids encoding these proteins into human 293T cells and performed immunoblotting with anti-phosphopeptide antibodies that detect phosphorylation of human Mcm2 on S108 (which corresponds to S92 of Xmcm2) (Cortez et al., 2004; Yoo et al., 2004).

As shown in FIG. 6C, cells expressing the wild-type 978-1286 fragment of human TopBP1 displayed significantly elevated phosphorylation of Mcm2 on S108, whereas there was no effect on cells expressing EGFP alone or the W1145R mutant. Moreover, Applicants also observed an increase in the phosphorylation of S108 in the presence of the 972-1286 human fragment by using indirect immunofluorescence (FIGS. 6D and E).

Therefore, the ATR-activating domain of human. TopBP1 can induce ATR-dependent phosphorylation of a downstream target in a human cell line in the absence of any DNA replication inhibitor or damaging agent.

Example VIII

Figure 7:
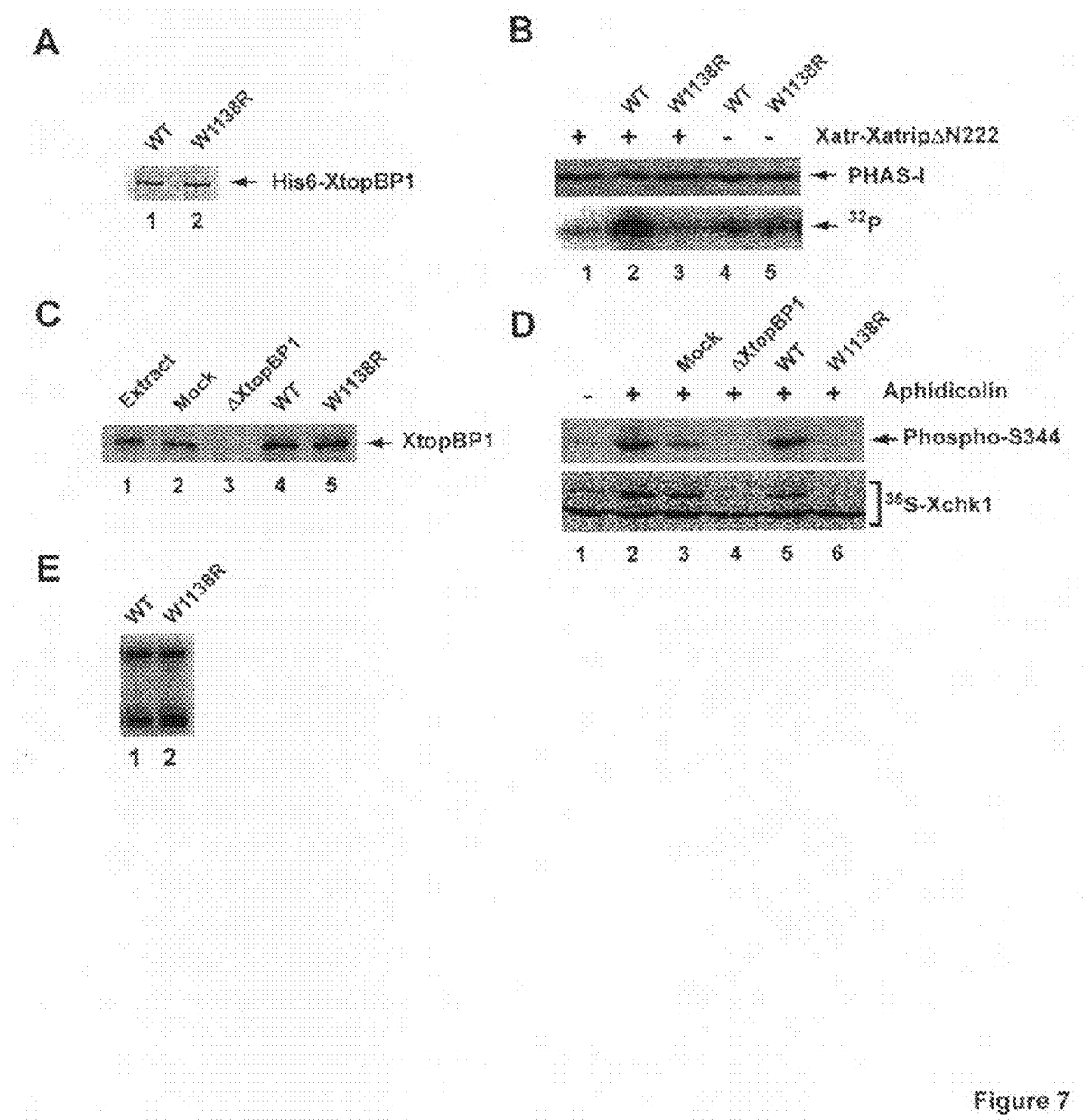
FIGS. 7A-7E show that the W1138R Mutant of XtopBP1 is defective in checkpoint regulation in *Xenopus* egg extracts.

An Intact ATR-Activating Domain is Necessary for XtopBP1 to Support Checkpoint-Dependent Phosphorylation of Xchk1 in Egg Extracts Finally, Applicants showed that XtopBP1 must possess an intact ATR-activating domain for Xenopus egg extracts to display a normal checkpoint response to stalled DNA replication forks. For this purpose, Applicants first produced a version of full-length His6-XtopBP1 with the W1138R mutation, which Applicants demonstrated is also unable to activate Xatr (FIGS. 7A and B). Applicants proceeded to remove endogenous XtopBP1 from egg extracts by immunodepletion with anti-XtopBP1 antibodies (FIG. 7C). In parallel, Applicants used control antibodies to prepare mock-depleted extract. Next, Applicants added back wild-type His6-XtopBP1 or the His6-XtopBP1-W1138R mutant to aliquots of the XtopBP1-depleted extract. Finally, Applicants added aphidicolin and demembranated *Xenopus* sperm nuclei to the various extracts in order to create stalled replication forks and then examined phosphorylation of Xchk1 (FIG. 7D).

Consistent with previous studies, the phosphorylation of Xchk1 was abolished in the absence of XtopBP1 (Parrilla-Castellar and Karnitz, 2003). As anticipated, addition of wild-type His6-XtopBP1 to the XtopBP1-depleted extract was able to rescue the phosphorylation of Xchk1 fully. By contrast, Applicants found that the W1138R mutant could not restore the phosphorylation of Xchk1.

In conjunction with these experiments, Applicants also examined chromosomal DNA replication in extracts containing either wild-type or W1138R His6-XtopBP1. As shown in FIG. 7E, DNA replication was not inhibited in extracts containing the W1138R mutant. Therefore, the defect in phosphorylation of Xchk1 in the extracts containing this mutant is not due to a failure in the assembly of DNA replication forks.

Taken together, these results indicate that XtopBP1 must have an intact ATR-activating domain in order to support the Xatr-dependent phosphorylation of Xchk1 that normally occurs in the presence of stalled DNA replication forks.

Certain exemplary (but non-limiting) experimental materials and methods are listed in the section below for illustration purpose only. A skilled artisan would be able to make minor modifications, if necessary, to adapt the materials or methods for similar experiments.

Experimental Procedures

*Xenopus* Egg Extracts

Extracts from *Xenopus* eggs were prepared as described (Kumagai and Dunphy, 2000). A DNA replication checkpoint response was induced by addition of 50 μg/ml aphidicolin into extracts containing demembranated sperm nuclei (3000 per μl) (Kumagai and Dunphy, 2000). To monitor DNA replication, extracts containing 1000 sperm nuclei/μl were incubated with [α-$^{32}$P]dATP (Yoo et al., 2004).

Antibodies

Antibodies against Xatr, Xatrip, Xatm, Xchk1, anti-phospho-S344 of Xchk1, and anti-phospho-S92 of Xmcm2 were described previously (Kumagai et al., 2004; Yoo et al., 2004). Anti-XtopBP1 antibodies were prepared as described (Van Hatten et al., 2002). Anti-FLAG, anti-Myc, anti-human Chk1 (G-4), anti-human Mcm2 (BM28), and control rabbit antibodies (IgG fraction) were purchased from Sigma, Calbiochem, Santa Cruz Biotechnology, BD Transduction Laboratories, and Zymed, respectively.

Recombinant Proteins

Full-length Xatrip-FLAG and XatripΔN222-FLAG with His6 and FLAG tags at the N-terminal and C-terminal ends, respectively, were produced in baculovirus-infected Sf9 insect cells (Kumagai et al., 2004; Kim et al., 2005). Full-length XtopBP1, XtopBP1Δ993-1196, and XtopBP1-W1138R with a His6 tag at their N-terminal ends were purified from Sf9 cells by the same procedure and dialyzed against 10 mM HEPES-KOH (pH 7.5), 80 mM NaCl, and 1 mM dithiothreitol. Full-length Xchk1 with Myc and His6 tags at the C-terminal end was also produced in Sf9 cells. GST fusion proteins containing fragments of XtopBP1 and human TopBP1 were produced in *Escherichia coli* BL21 CodonPlus RIL cells. Mutant DNA constructs prepared with the QuikChange kit (Stratagene).

Isolation of Xatr-Xatrip Complexes from Egg Extracts

Xatrip-FLAG and XatripΔN222-FLAG (20 ng/μl each) were incubated in interphase extracts containing anti-FLAG M2 antibody beads (Sigma) for 60 min at room temperature.

The beads were isolated and washed twice with buffer A (10 mM HEPES-KOH (pH 7.5), 150 mM NaCl, 0.1% CHAPS, and 2.5 mM EGTA) and twice with HEPES-buffered saline (HBS; 10 mM HEPES-KOH (pH 7.5) and 150 mM NaCl). Xatr-Xatrip complexes were eluted in one-tenth the volume of the egg extract in HBS containing 0.1 mg/ml 3×-FLAG peptide (Sigma) for 60 min at 4° C. Eluates (2 μl) were used for kinase assays as described below.

Kinase Assays

Samples were incubated in 20 μl kinase buffer (50 mM Tris-HCl (pH 7.5), 10 mM MgCl2, 1 mM dithiothreitol, 100 μM nonradioactive ATP, and 100 μCi/ml [γ-$^{32}$P]ATP) containing 12.5 μg/ml PHAS-I or 50 μg/ml GST-Xmcm2 (62-122) for 30 min at room temperature. GST-XtopBP1 (972-1279) was added at a final concentration of 100 μg/ml unless indicated otherwise. In some cases, GST-Xmcm2 (62-122), GST-Xchk1 (306-352), or full-length Xchk1-Myc-His6 were used as substrates with only 1 mM nonradioactive ATP. Reactions were terminated by boiling in gel sample buffer.

Immunodepletion from Egg Extracts

Xatr and Xatrip were immunodepleted as described (Kumagai et al., 2004). For immunodepletion of XtopBP1, we incubated 100 μl egg extract twice for 60 min with 10 μl Affiprep protein A beads (BioRad) containing 35 μg anti-XtopBP1 antibodies.

Preparation of Recombinant Wild-Type and Kinase-Deficient Human Flag-ATR

U2OS cells conditionally expressing wild-type (GW33) or kinase-deficient (GK41) human FLAG-ATR were cultured as described (Nghiem et al., 2001). Cells were induced with 1 μg/ml doxycycline for 48 hr. Nuclear extracts were prepared as described (Dignam et al., 1983) except that nuclei were lysed by brief sonication and the concentration of NaCl in the nuclear isolation buffer was reduced to 350 mM in order to preserve the binding of endogenous ATRIP to recombinant ATR. FLAG-ATR proteins were isolated by an overnight incubation with anti-FLAG antibodies bound to protein G-magnetic beads (Dynal) and eluted with 3×-FLAG peptide.

Expression of Human TopBP1 Fragments in Tissue Culture Cells pEGFP-NLS-TopBP1 (978-1286), which encodes EGFP followed by a nuclear localization sequence (KKKRKV, SEQ ID NO: 11) and amino acids 978-1286 of human TopBP1, was prepared from pEGFP (Clontech) by standard polymerase chain reaction-based methods. Plasmids were transfected into 293T cells with Lipofectamine 2000 (Invitrogen).

References

Abraham, R. T. (2001). Cell cycle checkpoint signaling through the ATM and ATR kinases. Genes Dev. 15, 2177-2196.

Araki, H., Leem, S. H., Phongdara, A., and Sugino, A. (1995). Dpb11, which interacts with DNA polymerase II (epsilon) in Saccharomyces cerevisiae, has a dual role in S-phase progression and at a cell cycle checkpoint. Proc. Nat. Acad. Sci. USA 92, 11791-11795.

Bakkenist, C. J., and Kastan, M. B. (2003). DNA damage activates ATM through intermolecular autophosphorylation and dimer dissociation. Nature 421, 499-506.

Bakkenist, C. J., and Kastan, M. B. (2004). Initiating cellular stress responses. Cell 118, 9-17.

Ball, H. L., and Cortez, D. (2005). ATRIP oligomerization is required for ATR-dependent checkpoint signaling. J. Biol. Chem. 280, 31390-31396.

Ball, H. L., Myers, J. S., and Cortez, D. (2005). ATRIP binding to replication protein A-single-stranded DNA promotes ATR-ATRIP localization but is dispensable for Chk1 phosphorylation. Mol. Biol. Cell 16, 2372-2381.

Byun, T. S., Pacek, M., Yee, M. C., Walter, J. C., and Cimprich, K. A. (2005). Functional uncoupling of MCM helicase and DNA polymerase activities activates the ATR-dependent checkpoint. Genes Dev. 19, 1040-1052.

Canman, C. E. (2003). Checkpoint mediators: relaying signals from DNA strand breaks. Curr. Biol. 13, R488-490.

Chini, C. C., and Chen, J. (2003). Human Claspin is required for replication checkpoint control. J. Biol. Chem. 278, 30057-30062.

Cortez, D., Glick, G., and Elledge, S. J. (2004). Minichromosome maintenance proteins are direct targets of the ATM and ATR checkpoint kinases. Proc. Nat. Acad. Sci. USA 101, 10078-10083.

Cortez, D., Guntuku, S., Qin, J., and Elledge, S. J. (2001). ATR and ATRIP: partners in checkpoint signaling. Science 294, 1713-1716.

Costanzo, V., Shechter, D., Lupardus, P. J., Cimprich, K. A., Gottesman, M., and Gautier, J. (2003). An ATR- and Cdc7-dependent DNA damage checkpoint that inhibits initiation of DNA replication. Mol. Cell. 11, 203-213.

Dignam, J. D., Lebovitz, R. M., and Roeder, R. G. (1983). Accurate transcription initiation by RNA polymerase II in a soluble extract from isolated mammalian nuclei. Nucleic Acids Res. 11, 1475-1489.

Falck, J., Coates, J., and Jackson, S. P. (2005). Conserved modes of recruitment of ATM, ATR and DNA-PKcs to sites of DNA damage. Nature 434, 605-611.

Garcia, V., Furuya, K., and Carr, A. M. (2005). Identification and functional analysis of TopBP1 and its homologs. DNA Repair (Amst.) 4, 1227-1239.

Guo, Z., Kumagai, A., Wang, S. X., and Dunphy, W. G. (2000). Requirement for Atr in phosphorylation of Chk1 and cell cycle regulation in response to DNA replication blocks and UV-damaged DNA in Xenopus egg extracts. Genes Dev. 14, 2745-2756.

Hashimoto, Y., and Takisawa, H. (2003). Xenopus Cut5 is essential for a CDK-dependent process in the initiation of DNA replication. EMBO J. 22, 2526-2535.

Hekmat-Nejad, M., You, Z., Yee, M., Newport, J. W., and Cimprich, K. A. (2000). Xenopus ATR is a replication-dependent chromatin-binding protein required for the DNA replication checkpoint. Curr. Biol. 10, 1565-1573.

Holway, A. H., Hung, C., and Michael, W. M. (2005). Systematic, RNA-interference-mediated identification of mus-101 modifier genes in Caenorhabditis elegans. Genetics 169, 1451-1460.

Honda, Y., Tojo, M., Matsuzaki, K., Anan, T., Matsumoto, M., Ando, M., Saya, H., and Nakao, M. (2002). Cooperation of HECT-domain ubiquitin ligase hHYD and DNA topoisomerase II-binding protein for DNA damage response. J. Biol. Chem. 277, 3599-3605.

Itakura, E., Sawada, I., and Matsuura, A. (2005). Dimerization of the ATRIP protein through the coiled-coil motif and its implication to the maintenance of stalled replication forks. Mol. Biol. Cell 16, 5551-5562.

Kim, S. M., Kumagai, A., Lee, J., and Dunphy, W. G. (2005). Phosphorylation of Chk1 by ATM- and Rad3-related (ATR) in Xenopus egg extracts requires binding of ATRIP to ATR but not the stable DNA-binding or coiled-coil domains of ATRIP. J. Biol. Chem. 280, 38355-38364.

Kumagai, A., and Dunphy, W. G. (2000). Claspin, a novel protein required for the activation of Chk1 during a DNA replication checkpoint response in Xenopus egg extracts. Mol. Cell. 6, 839-849.

Kumagai, A., Guo, Z., Emami, K. H., Wang, S. X., and Dunphy, W. G. (1998). The *Xenopus* Chk1 protein kinase mediates a caffeine-sensitive pathway of checkpoint control in cell-free extracts. J. Cell Biol. 142, 1559-1569.

Kumagai, A., Kim, S.-M., and Dunphy, W. G. (2004). Claspin and the activated form of ATR-ATRIP collaborate in the activation of Chk1. J. Biol. Chem. 279, 49599-49608.

Lee, J., Gold, D. A., Shevchenko, A., Shevchenko, A., and Dunphy, W. G. (2005). Roles of replication fork-interacting and Chk1-activating domains from Claspin in a DNA replication checkpoint response. Mol. Biol. Cell 16, 5269-5282.

Lee, J., Kumagai, A., and Dunphy, W. G. (2003). Claspin, a Chk1-regulatory protein, monitors DNA replication on chromatin independently of RPA, ATR, and Rad17. Mol. Cell. 11, 329-340.

Lee, J. H., and Paull, T. T. (2005). ATM activation by DNA double-strand breaks through the Mre11-Rad50-Nbs1 complex. Science 308, 551-554.

Lin, S. Y., Li, K., Stewart, G. S., and Elledge, S. J. (2004). Human Claspin works with BRCA1 to both positively and negatively regulate cell proliferation. Proc. Nat. Acad. Sci. USA 101, 6484-6489.

Liu, Q., Guntuku, S., Cui, X. S., Matsuoka, S., Cortez, D., Tamai, K., Luo, G., Carattini-Rivera, S., DeMayo, F., Bradley, A., et al. (2000). Chk1 is an essential kinase that is regulated by Atr and required for the G(2)/M DNA damage checkpoint. Genes Dev. 14, 1448-1459.

Lupardus, P. J., Byun, T., Yee, M. C., Hekmat-Nejad, M., and Cimprich, K. A. (2002). A requirement for replication in activation of the ATR-dependent DNA damage checkpoint. Genes Dev. 16, 2327-2332.

Makiniemi, M., Hillukkala, T., Tuusa, J., Reini, K., Vaara, M., Huang, D., Pospiech, H., Majuri, I., Westerling, T., Makela, T. P., and Syväoja, J. E. (2001). BRCT domain-containing protein TopBP1 functions in DNA replication and damage response. J. Biol. Chem. 276, 30399-30406.

Michael, W. M., Ott, R., Fanning, E., and Newport, J. (2000). Activation of the DNA replication checkpoint through RNA synthesis by primase. Science 289, 2133-2137.

Morgan, D. O. (1997). Cyclin-dependent kinases: engines, clocks, and microprocessors. Annu. Rev. Cell Dev. Biol. 13, 261-291.

Nghiem, P., Park, P. K., Kim, Y., Vaziri, C., and Schreiber, S. L. (2001). ATR inhibition selectively sensitizes G1 checkpoint-deficient cells to lethal premature chromatin condensation. Proc. Nat. Acad. Sci. USA 98, 9092-9097.

Nyberg, K. A., Michelson, R. J., Putnam, C. W., and Weinert, T. A. (2002). Toward maintaining the genome: DNA damage and replication checkpoints. Annu. Rev. Genet. 36, 617-656.

Parrilla-Castellar, E. R., and Karnitz, L. M. (2003). Cut5 is required for the binding of Atr and DNA polymerase alpha to genotoxin-damaged chromatin. J. Biol. Chem. 278, 45507-45511.

Perera, D., Perez-Hidalgo, L., Moens, P. B., Reini, K., Lakin, N., Syväoja, J. E., San-Segundo, P. A., and Freire, R. (2004). TopBP1 and ATR colocalization at meiotic chromosomes: role of TopBP1/Cut5 in the meiotic recombination checkpoint. Mol. Biol. Cell 15, 1568-1579.

Saka, Y., and Yanagida, M. (1993). Fission yeast cut5+, required for S phase onset and M phase restraint, is identical to the radiation-damage repair gene rad4+. Cell 74, 383-393.

Sancar, A., Lindsey-Boltz, L. A., Ünsal-Kagmaz, K., and Linn, S. (2004). Molecular mechanisms of mammalian DNA repair and the DNA damage checkpoints. Annu. Rev. Biochem. 73, 39-85.

Sarkaria, J. N., Busby, E. C., Tibbetts, R. S., Roos, P., Taya, Y., Karnitz, L. M., and Abraham, R. T. (1999). Inhibition of ATM and ATR kinase activities by the radiosensitizing agent, caffeine. Cancer Res. 59, 4375-4382.

Stokes, M. P., Van Hatten, R., Lindsay, H. D., and Michael, W. M. (2002). DNA replication is required for the checkpoint response to damaged DNA in *Xenopus* egg extracts. J. Cell Biol. 158, 863-872.

Ünsal-Kagmaz, K., and Sancar, A. (2004). Quaternary structure of ATR and effects of ATRIP and replication protein A on its DNA binding and kinase activities. Mol. Cell. Biol. 24, 1292-1300.

van Attikum, H., and Gasser, S. M. (2005). The histone code at DNA breaks: a guide to repair? Nat. Rev. Mol. Cell. Biol. 6, 757-765.

Van Hatten, R. A., Tutter, A. V., Holway, A. H., Khederian, A. M., Walter, J. C., and Michael, W. M. (2002). The *Xenopus* Xmus101 protein is required for the recruitment of Cdc45 to origins of DNA replication. J. Cell Biol. 159, 541-547.

Yamane, K., Chen, J., and Kinsella, T. J. (2003). Both DNA topoisomerase II-binding protein 1 and BRCA1 regulate the G2-M cell cycle checkpoint. Cancer Res. 63, 3049-3053.

Yamane, K., Kawabata, M., and Tsuruo, T. (1997). A DNA-topoisomerase-II-binding protein with eight repeating regions similar to DNA-repair enzymes and to a cell-cycle regulator. Eur. J. Biochem. 250, 794-799.

Yamane, K., and Tsuruo, T. (1999). Conserved BRCT regions of TopBP1 and of the tumor suppressor BRCA1 bind strand breaks and termini of DNA. Oncogene 18, 5194-5203.

Yamane, K., Wu, X., and Chen, J. (2002). A DNA damage-regulated BRCT-containing protein, TopBP1, is required for cell survival. Mol. Cell. Biol. 22, 555-566.

Yoo, H. Y., Shevchenko, A., Shevchenko, A., and Dunphy, W. G. (2004). Mcm2 is a direct substrate of ATM and ATR during DNA damage and DNA replication checkpoint responses. J. Biol. Chem. 279, 53353-53364.

You, Z., Kong, L., and Newport, J. (2002). The role of single-stranded DNA and polymerase alpha in establishing the ATR, Hus1 DNA replication checkpoint. J. Biol. Chem. 277, 27088-27093.

Zhao, H., and Piwnica-Worms, H. (2001). ATR-mediated checkpoint pathways regulate phosphorylation and activation of human Chk1. Mol. Cell. Biol. 21, 4129-4139.

Zou, L., and Elledge, S. J. (2003). Sensing DNA damage through ATRIP recognition of RPA-ssDNA complexes. Science 300, 1542-1548.

The contents of all cited references (including literature references, issued patents, published patent applications as cited throughout this application) are hereby expressly incorporated by reference.

Equivalents

Those skilled in the art will recognize, or be able to ascertain using no more than routine experimentation, numerous equivalents to the specific method and reagents described herein, including alternatives, variants, additions, deletions, modifications and substitutions. Such equivalents are considered to be within the scope of this invention and are covered by the following claims.

We claim:

1. A method for modulating ATR (Ataxia Telangiectasia and Rad3 Related) activation by TopBP1 (Topoisomerase (DNA) II Binding Protein 1) comprising administering an ATR activator consisting essentially of (1) an ATR activation domain of TopBP1, or (2) a functional fragment thereof that is at least about 90% identical to the ATR activation domain of TopBP1, wherein said ATR activation domain of TopBP1 consists of residues 1050-1192, 978-1192, 972-1279, 1008-1286, or 1050-1286 of human TopBP1, and wherein said ATR activator activates the kinase activity of ATR.

2. The method of claim 1, further comprising contacting ATR with one or more modulators of ATR activity.

3. The method of claim 1, wherein ATR and said ATR activator are inside a cell.

4. The method of claim 3, wherein the cell is a vertebrate cell.

5. An ATR (Ataxia Telangiectasia and Rad3 Related) activator consisting essentially of (1) an ATR activation domain of TopBP1 (Topoisomerase (DNA) II Binding Protein 1), or (2) a functional fragment thereof that is at least about 90% identical to the ATR activation domain of TopBP1, wherein said ATR activation domain of TopBP1 consists of residues 1050-1192, 978-1192, 972-1279, 1008-1286, or 1050-1286 of human TopBP1, and wherein said ATR activator activates the kinase activity of ATR.

6. The ATR activator of claim 5, wherein said ATR activation domain of TopBP1 consists of residues 1050-1192 of human TopBP1.

7. The ATR activator of claim 5, wherein said ATR activation domain of TopBP1 consists of residues 978-1192 of human TopBP1.

8. The ATR activator of claim 5, wherein said ATR activation domain of TopBP1 consists of residues 972-1279 of human TopBP1.

9. The ATR activator of claim 5, wherein said ATR activation domain of TopBP1 consists of residues 1008-1286 of human TopBP1.

10. The ATR activator of claim 5, wherein said ATR activation domain of TopBP1 consists of residues 1050-1286 of human TopBP1.

* * * * *

SEQUENCE LISTING

<160> NUMBER OF SEQ ID NOS: 15

<210> SEQ ID NO 1
<211> LENGTH: 4
<212> TYPE: PRT
<213> ORGANISM: Xenopus laevis

<400> SEQUENCE: 1

Arg Gln Leu Gln
 1

<210> SEQ ID NO 2
<211> LENGTH: 4
<212> TYPE: PRT
<213> ORGANISM: Xenopus laevis

<400> SEQUENCE: 2

Trp Asp Asp Pro
 1

<210> SEQ ID NO 3
<211> LENGTH: 2644
<212> TYPE: PRT
<213> ORGANISM: Homo sapiens

<400> SEQUENCE: 3

Met Gly Glu His Gly Leu Glu Leu Ala Ser Met Ile Pro Ala Leu Arg
 1               5                  10                  15

Glu Leu Gly Ser Ala Thr Pro Glu Glu Tyr Asn Thr Val Val Gln Lys
            20                  25                  30

Pro Arg Gln Ile Leu Cys Gln Phe Ile Asp Arg Ile Leu Thr Asp Val
        35                  40                  45

Asn Val Val Ala Val Glu Leu Val Lys Lys Thr Asp Ser Gln Pro Thr
    50                  55                  60

Ser Val Met Leu Leu Asp Phe Ile Gln His Ile Met Lys Ser Ser Pro
65                  70                  75                  80

Leu Met Phe Val Asn Val Ser Gly Ser His Glu Arg Lys Gly Ser Cys
                85                  90                  95

Ile Glu Phe Ser Asn Trp Ile Ile Thr Arg Leu Leu Arg Ile Ala Ala
            100                 105                 110

Thr Pro Ser Cys His Leu Leu His Lys Lys Ile Cys Glu Val Ile Cys
        115                 120                 125

Ser Leu Leu Phe Leu Phe Lys Ser Lys Ser Pro Ala Ile Phe Gly Val
    130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Val Met Ser
                165                 170                 175

Arg Phe Leu Ser Gln Leu Asp Glu His Met Gly Tyr Leu Gln Ser Ala
            180                 185                 190

Pro Leu Gln Leu Met Ser Met Gln Asn Leu Glu Phe Ile Glu Val Thr
        195                 200                 205

Leu Leu Met Val Leu Thr Arg Ile Ile Ala Ile Val Phe Phe Arg Arg
    210                 215                 220

Gln Glu Leu Leu Leu Trp Gln Ile Gly Cys Val Leu Leu Glu Tyr Gly
225                 230                 235                 240

Ser Pro Lys Ile Lys Ser Leu Ala Ile Ser Phe Leu Thr Glu Leu Phe

```
                        245                 250                 255
Gln Leu Gly Gly Leu Pro Ala Gln Pro Ala Ser Thr Phe Phe Ser Ser
                    260                 265                 270

Phe Leu Glu Leu Leu Lys His Leu Val Glu Met Asp Thr Asp Gln Leu
                275                 280                 285

Lys Leu Tyr Glu Glu Pro Leu Ser Lys Leu Ile Lys Thr Leu Phe Pro
            290                 295                 300

Phe Glu Ala Glu Ala Tyr Arg Asn Ile Glu Pro Val Tyr Leu Asn Met
305                 310                 315                 320

Leu Leu Glu Lys Leu Cys Val Met Phe Glu Asp Gly Val Leu Met Arg
                325                 330                 335

Leu Lys Ser Asp Leu Leu Lys Ala Ala Leu Cys His Leu Leu Gln Tyr
                340                 345                 350

Phe Leu Lys Phe Val Pro Ala Gly Tyr Glu Ser Ala Leu Gln Val Arg
            355                 360                 365

Lys Val Tyr Val Arg Asn Ile Cys Lys Ala Leu Leu Asp Val Leu Gly
        370                 375                 380

Ile Glu Val Asp Ala Glu Tyr Leu Leu Gly Pro Leu Tyr Ala Ala Leu
385                 390                 395                 400

Lys Met Glu Ser Met Glu Ile Ile Glu Glu Ile Gln Cys Gln Thr Gln
                405                 410                 415

Gln Glu Asn Leu Ser Ser Asn Ser Asp Gly Ile Ser Pro Lys Arg Arg
                420                 425                 430

Arg Leu Ser Ser Ser Leu Asn Pro Ser Lys Arg Ala Pro Lys Gln Thr
            435                 440                 445

Glu Glu Ile Lys His Val Asp Met Asn Gln Lys Ser Ile Leu Trp Ser
        450                 455                 460

Ala Leu Lys Gln Lys Ala Glu Ser Leu Gln Ile Ser Leu Glu Tyr Ser
465                 470                 475                 480

Gly Leu Lys Asn Pro Val Ile Glu Met Leu Glu Gly Ile Ala Val Val
                485                 490                 495

Leu Gln Leu Thr Ala Leu Cys Thr Val His Cys Ser His Gln Asn Met
                500                 505                 510

Asn Cys Arg Thr Phe Lys Asp Cys Gln His Lys Ser Lys Lys Lys Pro
            515                 520                 525

Ser Val Val Ile Thr Trp Met Ser Leu Asp Phe Tyr Thr Lys Val Leu
        530                 535                 540

Lys Ser Cys Arg Ser Leu Leu Glu Ser Val Gln Lys Leu Asp Leu Glu
545                 550                 555                 560

Ala Thr Ile Asp Lys Val Val Lys Ile Tyr Asp Ala Leu Ile Tyr Met
                565                 570                 575

Gln Val Asn Ser Ser Phe Glu Asp His Ile Leu Glu Asp Leu Cys Gly
                580                 585                 590

Met Leu Ser Leu Pro Trp Ile Tyr Ser His Ser Asp Asp Gly Cys Leu
            595                 600                 605

Lys Leu Thr Thr Phe Ala Ala Asn Leu Leu Thr Leu Ser Cys Arg Ile
        610                 615                 620

Ser Asp Ser Tyr Ser Pro Gln Ala Gln Ser Arg Cys Val Phe Leu Leu
625                 630                 635                 640

Thr Leu Phe Pro Arg Arg Ile Phe Leu Glu Trp Arg Thr Ala Val Tyr
                645                 650                 655

Asn Trp Ala Leu Gln Ser Ser His Glu Val Ile Arg Ala Ser Cys Val
                660                 665                 670
```

-continued

```
Ser Gly Phe Phe Ile Leu Leu Gln Gln Asn Ser Cys Asn Arg Val
        675                 680                 685
Pro Lys Ile Leu Ile Asp Lys Val Lys Asp Ser Asp Ile Val Lys
690                 695                 700
Lys Glu Phe Ala Ser Ile Leu Gly Gln Leu Val Cys Thr Leu His Gly
705                 710                 715                 720
Met Phe Tyr Leu Thr Ser Ser Leu Thr Glu Pro Phe Ser Glu His Gly
                725                 730                 735
His Val Asp Leu Phe Cys Arg Asn Leu Lys Ala Thr Ser Gln His Glu
                740                 745                 750
Cys Ser Ser Ser Gln Leu Lys Ala Ser Val Cys Lys Pro Phe Leu Phe
                755                 760                 765
Leu Leu Lys Lys Lys Ile Pro Ser Pro Val Lys Leu Ala Phe Ile Asp
        770                 775                 780
Asn Leu His His Leu Cys Lys His Leu Asp Phe Arg Glu Asp Glu Thr
785                 790                 795                 800
Asp Val Lys Ala Val Leu Gly Thr Leu Leu Asn Leu Met Glu Asp Pro
                805                 810                 815
Asp Lys Asp Val Arg Val Ala Phe Ser Gly Asn Ile Lys His Ile Leu
                820                 825                 830
Glu Ser Leu Asp Ser Glu Asp Gly Phe Ile Lys Glu Leu Phe Val Leu
                835                 840                 845
Arg Met Lys Glu Ala Tyr Thr His Ala Gln Ile Ser Arg Asn Asn Glu
        850                 855                 860
Leu Lys Asp Thr Leu Ile Leu Thr Thr Gly Asp Ile Gly Arg Ala Ala
865                 870                 875                 880
Lys Gly Asp Leu Val Pro Phe Ala Leu Leu His Leu His Cys Leu
                885                 890                 895
Leu Ser Lys Ser Ala Ser Val Ser Gly Ala Ala Tyr Thr Glu Ile Arg
        900                 905                 910
Ala Leu Val Ala Ala Lys Ser Val Lys Leu Gln Ser Phe Phe Ser Gln
        915                 920                 925
Tyr Lys Lys Pro Ile Cys Gln Phe Leu Val Glu Ser Leu His Ser Ser
        930                 935                 940
Gln Met Thr Ala Leu Pro Asn Thr Pro Cys Gln Asn Ala Asp Val Arg
945                 950                 955                 960
Lys Gln Asp Val Ala His Gln Arg Glu Met Ala Leu Asn Thr Leu Ser
                965                 970                 975
Glu Ile Ala Asn Val Phe Asp Phe Pro Asp Leu Asn Arg Phe Leu Thr
                980                 985                 990
Arg Thr Leu Gln Val Leu Leu Pro Asp Leu Ala Ala Lys Ala Ser Pro
        995                 1000                1005
Ala Ala Ser Ala Leu Ile Arg Thr Leu Gly Lys Gln Leu Asn Val Asn
        1010                1015                1020
Arg Arg Glu Ile Leu Ile Asn Asn Phe Lys Tyr Ile Phe Ser His Leu
1025                1030                1035                1040
Val Cys Ser Cys Ser Lys Asp Glu Leu Glu Arg Ala Leu His Tyr Leu
                1045                1050                1055
Lys Asn Glu Thr Glu Ile Glu Leu Gly Ser Leu Leu Arg Gln Asp Phe
                1060                1065                1070
Gln Gly Leu His Asn Glu Leu Leu Leu Arg Ile Gly Glu His Tyr Gln
        1075                1080                1085
Gln Val Phe Asn Gly Leu Ser Ile Leu Ala Ser Phe Ala Ser Ser Asp
        1090                1095                1100
```

```
Asp Pro Tyr Gln Gly Pro Arg Asp Ile Ile Ser Pro Glu Leu Met Ala
1105                1110                1115                1120

Asp Tyr Leu Gln Pro Lys Leu Leu Gly Ile Leu Ala Phe Phe Asn Met
            1125                1130                1135

Gln Leu Leu Ser Ser Val Gly Ile Glu Asp Lys Lys Met Ala Leu
        1140                1145                1150

Asn Ser Leu Met Ser Leu Met Lys Leu Met Gly Pro Lys His Val Ser
        1155                1160                1165

Ser Val Arg Val Lys Met Met Thr Thr Leu Arg Thr Gly Leu Arg Phe
    1170                1175                1180

Lys Asp Asp Phe Pro Glu Leu Cys Cys Arg Ala Trp Asp Cys Phe Val
1185                1190                1195                1200

Arg Cys Leu Asp His Ala Cys Leu Gly Ser Leu Leu Ser His Val Ile
            1205                1210                1215

Val Ala Leu Leu Pro Leu Ile His Ile Gln Pro Lys Glu Thr Ala Ala
            1220                1225                1230

Ile Phe His Tyr Leu Ile Ile Glu Asn Arg Asp Ala Val Gln Asp Phe
            1235                1240                1245

Leu His Glu Ile Tyr Phe Leu Pro Asp His Pro Glu Leu Lys Lys Ile
    1250                1255                1260

Lys Ala Val Leu Gln Glu Tyr Arg Lys Glu Thr Ser Glu Ser Thr Asp
1265                1270                1275                1280

Leu Gln Thr Thr Leu Gln Leu Ser Met Lys Ala Ile Gln His Glu Asn
            1285                1290                1295

Val Asp Val Arg Ile His Ala Leu Thr Ser Leu Lys Glu Thr Leu Tyr
        1300                1305                1310

Lys Asn Gln Glu Lys Leu Ile Lys Tyr Ala Thr Asp Ser Glu Thr Val
        1315                1320                1325

Glu Pro Ile Ile Ser Gln Leu Val Thr Val Leu Leu Lys Gly Cys Gln
1330                1335                1340

Asp Ala Asn Ser Gln Ala Arg Leu Leu Cys Gly Glu Cys Leu Gly Glu
1345                1350                1355                1360

Leu Gly Ala Ile Asp Pro Gly Arg Leu Asp Phe Ser Thr Thr Glu Thr
        1365                1370                1375

Gln Gly Lys Asp Phe Thr Phe Val Thr Gly Val Glu Asp Ser Ser Phe
        1380                1385                1390

Ala Tyr Gly Leu Leu Met Glu Leu Thr Arg Ala Tyr Leu Ala Tyr Ala
        1395                1400                1405

Asp Asn Ser Arg Ala Gln Asp Ser Ala Ala Tyr Ala Ile Gln Glu Leu
    1410                1415                1420

Leu Ser Ile Tyr Asp Cys Arg Glu Met Glu Thr Asn Gly Pro Gly His
1425                1430                1435                1440

Gln Leu Trp Arg Arg Phe Pro Glu His Val Arg Glu Ile Leu Glu Pro
            1445                1450                1455

His Leu Asn Thr Arg Tyr Lys Ser Ser Gln Lys Ser Thr Asp Trp Ser
        1460                1465                1470

Gly Val Lys Lys Pro Ile Tyr Leu Ser Lys Leu Gly Ser Asn Phe Ala
        1475                1480                1485

Glu Trp Ser Ala Ser Trp Ala Gly Tyr Leu Ile Thr Lys Val Arg His
    1490                1495                1500

Asp Leu Ala Ser Lys Ile Phe Thr Cys Cys Ser Ile Met Met Lys His
1505                1510                1515                1520

Asp Phe Lys Val Thr Ile Tyr Leu Leu Pro His Ile Leu Val Tyr Val
```

```
                    1525                1530                1535
Leu Leu Gly Cys Asn Gln Glu Asp Gln Gln Glu Val Tyr Ala Glu Ile
            1540                1545                1550
Met Ala Val Leu Lys His Asp Asp Gln His Thr Ile Asn Thr Gln Asp
            1555                1560                1565
Ile Ala Ser Asp Leu Cys Gln Leu Ser Thr Gln Thr Val Phe Ser Met
            1570                1575                1580
Leu Asp His Leu Thr Gln Trp Ala Arg His Lys Phe Gln Ala Leu Lys
1585                1590                1595                1600
Ala Glu Lys Cys Pro His Ser Lys Ser Asn Arg Asn Lys Val Asp Ser
            1605                1610                1615
Met Val Ser Thr Val Asp Tyr Glu Asp Tyr Gln Ser Val Thr Arg Phe
            1620                1625                1630
Leu Asp Leu Ile Pro Gln Asp Thr Leu Ala Val Ala Ser Phe Arg Ser
            1635                1640                1645
Lys Ala Tyr Thr Arg Ala Val Met His Phe Glu Ser Phe Ile Thr Glu
            1650                1655                1660
Lys Lys Gln Asn Ile Gln Glu His Leu Gly Phe Leu Gln Lys Leu Tyr
1665                1670                1675                1680
Ala Ala Met His Glu Pro Asp Gly Val Ala Gly Val Ser Ala Ile Arg
            1685                1690                1695
Lys Ala Glu Pro Ser Leu Lys Glu Gln Ile Leu Glu His Glu Ser Leu
            1700                1705                1710
Gly Leu Leu Arg Asp Ala Thr Ala Cys Tyr Asp Arg Ala Ile Gln Leu
            1715                1720                1725
Glu Pro Asp Gln Ile Ile His Tyr His Gly Val Val Lys Ser Met Leu
            1730                1735                1740
Gly Leu Gly Gln Leu Ser Thr Val Ile Thr Gln Val Asn Gly Val His
1745                1750                1755                1760
Ala Asn Arg Ser Glu Trp Thr Asp Glu Leu Asn Thr Tyr Arg Val Glu
            1765                1770                1775
Ala Ala Trp Lys Leu Ser Gln Trp Asp Leu Val Glu Asn Tyr Leu Ala
            1780                1785                1790
Ala Asp Gly Lys Ser Thr Thr Trp Ser Val Arg Leu Gly Gln Leu Leu
            1795                1800                1805
Leu Ser Ala Lys Lys Arg Asp Ile Thr Ala Phe Tyr Asp Ser Leu Lys
            1810                1815                1820
Leu Val Arg Ala Glu Gln Ile Val Pro Leu Ser Ala Ala Ser Phe Glu
1825                1830                1835                1840
Arg Gly Ser Tyr Gln Arg Gly Tyr Glu Tyr Ile Val Arg Leu His Met
            1845                1850                1855
Leu Cys Glu Leu Glu His Ser Ile Lys Pro Leu Phe Gln His Ser Pro
            1860                1865                1870
Gly Asp Ser Ser Gln Glu Asp Ser Leu Asn Trp Val Ala Arg Leu Glu
            1875                1880                1885
Met Thr Gln Asn Ser Tyr Arg Ala Lys Glu Pro Ile Leu Ala Leu Arg
            1890                1895                1900
Arg Ala Leu Leu Ser Leu Asn Lys Arg Pro Asp Tyr Asn Glu Met Val
1905                1910                1915                1920
Gly Glu Cys Trp Leu Gln Ser Ala Arg Val Ala Arg Lys Ala Gly His
            1925                1930                1935
His Gln Thr Ala Tyr Asn Ala Leu Leu Asn Ala Gly Glu Ser Arg Leu
            1940                1945                1950
```

```
Ala Glu Leu Tyr Val Glu Arg Ala Lys Trp Leu Trp Ser Lys Gly Asp
        1955                1960                1965

Val His Gln Ala Leu Ile Val Leu Gln Lys Gly Val Glu Leu Cys Phe
    1970                1975                1980

Pro Glu Asn Glu Thr Pro Pro Glu Gly Lys Asn Met Leu Ile His Gly
1985                1990                1995                2000

Arg Ala Met Leu Leu Val Gly Arg Phe Met Glu Glu Thr Ala Asn Phe
            2005                2010                2015

Glu Ser Asn Ala Ile Met Lys Lys Tyr Lys Asp Val Thr Ala Cys Leu
        2020                2025                2030

Pro Glu Trp Glu Asp Gly His Phe Tyr Leu Ala Lys Tyr Tyr Asp Lys
    2035                2040                2045

Leu Met Pro Met Val Thr Asp Asn Lys Met Glu Lys Gln Gly Asp Leu
2050                2055                2060

Ile Arg Tyr Ile Val Leu His Phe Gly Arg Ser Leu Gln Tyr Gly Asn
2065                2070                2075                2080

Gln Phe Ile Tyr Gln Ser Met Pro Arg Met Leu Thr Leu Trp Leu Asp
            2085                2090                2095

Tyr Gly Thr Lys Ala Tyr Glu Trp Glu Lys Ala Gly Arg Ser Asp Arg
        2100                2105                2110

Val Gln Met Arg Asn Asp Leu Gly Lys Ile Asn Lys Val Ile Thr Glu
    2115                2120                2125

His Thr Asn Tyr Leu Ala Pro Tyr Gln Phe Leu Thr Ala Phe Ser Gln
2130                2135                2140

Leu Ile Ser Arg Ile Cys His Ser His Asp Val Phe Val Val Leu
2145                2150                2155                2160

Met Glu Ile Ile Ala Lys Val Phe Leu Ala Tyr Pro Gln Gln Ala Met
            2165                2170                2175

Trp Met Met Thr Ala Val Ser Lys Ser Ser Tyr Pro Met Arg Val Asn
        2180                2185                2190

Arg Cys Lys Glu Ile Leu Asn Lys Ala Ile His Met Lys Lys Ser Leu
    2195                2200                2205

Glu Lys Phe Val Gly Asp Ala Thr Arg Leu Thr Asp Lys Leu Leu Glu
2210                2215                2220

Leu Cys Asn Lys Pro Val Asp Gly Ser Ser Ser Thr Leu Ser Met Ser
2225                2230                2235                2240

Thr His Phe Lys Met Leu Lys Lys Leu Val Glu Ala Thr Phe Ser
            2245                2250                2255

Glu Ile Leu Ile Pro Leu Gln Ser Val Met Ile Pro Thr Leu Pro Ser
        2260                2265                2270

Ile Leu Gly Thr His Ala Asn His Ala Ser His Glu Pro Phe Pro Gly
    2275                2280                2285

His Trp Ala Tyr Ile Ala Gly Phe Asp Asp Met Val Glu Ile Leu Ala
2290                2295                2300

Ser Leu Gln Lys Pro Lys Lys Ile Ser Leu Lys Gly Ser Asp Gly Lys
2305                2310                2315                2320

Phe Tyr Ile Met Met Cys Lys Pro Lys Asp Asp Leu Arg Lys Asp Cys
            2325                2330                2335

Arg Leu Met Glu Phe Asn Ser Leu Ile Asn Lys Cys Leu Arg Lys Asp
        2340                2345                2350

Ala Glu Ser Arg Arg Arg Glu Leu His Ile Arg Thr Tyr Ala Val Ile
    2355                2360                2365

Pro Leu Asn Asp Glu Cys Gly Ile Ile Glu Trp Val Asn Asn Thr Ala
2370                2375                2380
```

Gly Leu Arg Pro Ile Leu Thr Lys Leu Tyr Lys Glu Lys Gly Val Tyr
2385                2390                2395                2400

Met Thr Gly Lys Glu Leu Arg Gln Cys Met Leu Pro Lys Ser Ala Ala
            2405                2410                2415

Leu Ser Glu Lys Leu Lys Val Phe Arg Glu Phe Leu Leu Pro Arg His
        2420                2425                2430

Pro Pro Ile Phe His Glu Trp Phe Leu Arg Thr Phe Pro Asp Pro Thr
    2435                2440                2445

Ser Trp Tyr Ser Ser Arg Ser Ala Tyr Cys Arg Ser Thr Ala Val Met
2450                2455                2460

Ser Met Val Gly Tyr Ile Leu Gly Leu Gly Asp Arg His Gly Glu Asn
2465                2470                2475                2480

Ile Leu Phe Asp Ser Leu Thr Gly Glu Cys Val His Val Asp Phe Asn
                2485                2490                2495

Cys Leu Phe Asn Lys Gly Glu Thr Phe Glu Val Pro Glu Ile Val Pro
            2500                2505                2510

Phe Arg Leu Thr His Asn Met Val Asn Gly Met Gly Pro Met Gly Thr
        2515                2520                2525

Glu Gly Leu Phe Arg Arg Ala Cys Glu Val Thr Met Arg Leu Met Arg
    2530                2535                2540

Asp Gln Arg Glu Pro Leu Met Ser Val Leu Lys Thr Phe Leu His Asp
2545                2550                2555                2560

Pro Leu Val Glu Trp Ser Lys Pro Val Lys Gly His Ser Lys Ala Pro
                2565                2570                2575

Leu Asn Glu Thr Gly Glu Val Val Asn Glu Lys Ala Lys Thr His Val
            2580                2585                2590

Leu Asp Ile Glu Gln Arg Leu Gln Gly Val Ile Lys Thr Arg Asn Arg
        2595                2600                2605

Val Thr Gly Leu Pro Leu Ser Ile Glu Gly His Val His Tyr Leu Ile
    2610                2615                2620

Gln Glu Ala Thr Asp Glu Asn Leu Leu Cys Gln Met Tyr Leu Gly Trp
2625                2630                2635                2640

Thr Pro Tyr Met

<210> SEQ ID NO 4
<211> LENGTH: 8265
<212> TYPE: DNA
<213> ORGANISM: Homo sapiens

<400> SEQUENCE: 4
gcctccacac ggctccgtcg ggcgccgcgc tcttccggca gcggtacgtt tggagacgcc        60
gggaacccgc gttggcgtgg ttgactagtg cctcgcagcc tcagcatggg ggaacatggc       120
ctggagctgg cttccatgat ccccgccctg cgggagctgg gcagtgccac accagaggaa       180
tataatacag ttgtacagaa gccaagacaa attctgtgtc aattcattga ccggatactt       240
acagatgtaa atgttgttgc tgtagaactt gtaaagaaaa ctgactctca gccaacctcc       300
gtgatgttgc ttgatttcat ccagcatatc atgaaatcct ccccacttat gtttgtaaat       360
gtgagtggaa gccatgagcg caaaggcagt tgtattgaat tcagtaattg gatcataacg       420
agacttctgc ggattgcagc aactcccctcc tgtcatttgt tacacaagaa aatctgtgaa       480
gtcatctgtt cattattatt tcttttttaaa agcaagagtc ctgctatttt tggggtactc       540
acaaaagaat tattcaaact ttttgaagac ttggttttacc tccatagaag aaatgtgatg       600
ggtcatgctg tggaatggcc agtggtcatg agccgatttt taagtcaatt agatgaacac       660

```
atgggatatt tacaatcagc tcctttgcag ttgatgagta tgcaaaattt agaatttatt      720
gaagtcactt tattaatggt tcttactcgt attattgcaa ttgtgttttt tagaaggcaa      780
gaactcttac tttggcagat aggttgtgtt ctgctagagt atggtagtcc aaaaattaaa      840
tccctagcaa ttagcttttt aacagaactt tttcagcttg gaggactacc agcacaacca      900
gctagcactt ttttcagctc attttttggaa ttattaaaac accttgtaga aatggatact      960
gaccaattga aactctatga agagccatta tcaaagctga taaagacact atttcccttt     1020
gaagcagaag cttatagaaa tattgaacct gtctatttaa atatgctgct ggaaaaactc     1080
tgtgtcatgt ttgaagacgg tgtgctcatg cggcttaagt ctgatttgct aaaagcagct     1140
ttgtgccatt tactgcagta tttccttaaa tttgtgccag ctgggtatga atctgcttta     1200
caagtcagga aggtctatgt gagaaatatt tgtaaagctc ttttggatgt gcttggaatt     1260
gaggtagatg cagagtactt gttgggccca ctttatgcag ctttgaaaat ggaaagtatg     1320
gaaatcattg aggagattca atgccaaact caacaggaaa acctcagcag taatagtgat     1380
ggaatatcac ccaaaaggcg tcgtctcagc tcgtctctaa acccttctaa aagagcacca     1440
aaacagactg aggaaattaa acatgtggac atgaaccaaa agagcatatt atggagtgca     1500
ctgaaacaga aagctgaatc ccttcagatt tcccttgaat acagtggcct aaagaatcct     1560
gttattgaga tgttagaagg aattgctgtt gtcttacaac tgactgctct gtgtactgtt     1620
cattgttctc atcaaaacat gaactgccgt actttcaagg actgtcaaca taaatccaag     1680
aagaaacctt ctgtagtgat aacttggatg tcattggatt tttacacaaa agtgcttaag     1740
agctgtagaa gtttgttaga atctgttcag aaactggacc tggaggcaac cattgataag     1800
gtggtgaaaa tttatgatgc tttgatttat atgcaagtaa acagttcatt tgaagatcat     1860
atcctggaag atttatgtgg tatgctctca cttccatgga tttattccca ttctgatgat     1920
ggctgtttaa agttgaccac atttgccgct aatcttctaa cattaagctg taggatttca     1980
gatagctatt caccacaggc acaatcacga tgtgtgtttc ttctgactct gtttccaaga     2040
agaatattcc ttgagtggag aacagcagtt tacaactggg ccctgcagag ctcccatgaa     2100
gtaatccggg ctagttgtgt tagtggattt tttatcttat tgcagcagca gaattcttgt     2160
aacagagttc ccaagattct tatagataaa gtcaaagatg attctgacat tgtcaagaaa     2220
gaatttgctt ctatacttgg tcaacttgtc tgtactcttc acggcatgtt ttatctgaca     2280
agttctttaa cagaaccttt ctctgaacac ggacatgtgg acctcttctg taggaacttg     2340
aaagccactt ctcaacatga atgttcatct tctcaactaa aagcttctgt ctgcaagcca     2400
ttccttttcc tactgaaaaa aaaaatacct agtccagtaa aacttgcttt catagataat     2460
ctacatcatc tttgtaagca tcttgatttt agagaagatg aaacagatgt aaaagcagtt     2520
cttggaactt tattaaattt aatggaagat ccagacaaag atgttagagt ggctttagt     2580 ggaaatatca agcacatatt ggaatccttg gactctgaag atggatttat aaaggagctt     2640
tttgtcttaa gaatgaagga agcatataca catgcccaaa tatcaagaaa taatgagctg     2700
aaggatacct tgattcttac aacaggggat attggaaggg ccgcaaaagg agatttggta     2760
ccatttgcac tcttacactt attgcattgt ttgttatcca agtcagcatc tgtctctgga     2820
gcagcataca cagaaattag agctctggtt gcagctaaaa gtgttaaact gcaaagtttt     2880
ttcagccagt ataagaaacc catctgtcag ttttttggtag aatcccttca ctctagtcag     2940
atgacagcac ttccgaatac tccatgccag aatgctgacg tgcgaaaaca agatgtggct     3000
caccagagag aaatggcttt aaatacgttg tctgaaattg ccaacgtttt cgactttcct     3060
```

```
gatcttaatc gttttcttac taggacatta caagttctac tacctgatct tgctgccaaa    3120
gcaagccctg cagcttctgc tctcattcga actttaggaa acaattaaa tgtcaatcgt     3180 agagagattt taataaacaa cttcaaatat attttttctc atttggtctg ttcttgttcc    3240
aaagatgaat tagaacgtgc ccttcattat ctgaagaatg aaacagaaat tgaactgggg    3300
agcctgttga gacaagattt ccaaggattg cataatgaat tattgctgcg tattggagaa    3360
cactatcaac aggttttaa tggtttgtca atacttgcct catttgcatc cagtgatgat     3420
ccatatcagg gcccgagaga tatcatatca cctgaactga tggctgatta tttacaaccc    3480
aaattgttgg gcattttggc ttttttaac atgcagttac tgagctctag tgttggcatt     3540
gaagataaga aaatggcctt gaacagtttg atgtctttga tgaagttaat gggacccaaa    3600
catgtcagtt ctgtgagggt gaagatgatg accacactga gaactggcct tcgattcaag    3660
gatgattttc ctgaattgtg ttgcagagct tgggactgct tgttcgctg cctggatcat     3720 gcttgtctgg gctcccttct cagtcatgta atagtagctt tgttacctct tatacacatc    3780
cagcctaaag aaactgcagc tatcttccac tacctcataa ttgaaaacag ggatgctgtg    3840
caagattttc ttcatgaaat atattttta cctgatcatc cagaattaaa aaagataaaa    3900
gccgttctcc aggaatacag aaaggagacc tctgagagca ctgatcttca gacaactctt    3960
cagctctcta tgaaggccat tcaacatgaa atgtcgatg ttcgtattca tgctcttaca     4020
agcttgaagg aaaccttgta taaaaatcag gaaaaactga taaagtatgc aacagacagt    4080
gaaacagtag aacctattat ctcacagttg gtgacagtgc ttttgaaagg ttgccaagat    4140
gcaaactctc aagctcggtt gctctgtggg gaatgtttag gggaattggg ggcgatagat    4200
ccaggtcgat tagatttctc aacaactgaa actcaaggaa aagattttac atttgtgact    4260
ggagtagaag attcaagctt tgcctatgga ttattgatgg agctaacaag agcttacctt    4320
gcgtatgctg ataatagccg agctcaagat tcagctgcct atgccattca ggagttgctt    4380
tctatttatg actgtagaga gatggagacc aacggcccag gtcaccaatt gtggaggaga    4440
tttcctgagc atgttcggga aatactagaa cctcatctaa ataccagata caagagttct    4500
cagaagtcaa ccgattggtc tggagtaaag aagccaattt acttaagtaa attgggtagt    4560
aactttgcag aatggtcagc atcttgggca ggttatctta ttacaaaggt tcgacatgat    4620
cttgccagta aaattttcac ctgctgtagc attatgatga agcatgattt caaagtgacc    4680
atctatcttc ttccacatat tctggtgtat gtcttactgg gttgtaatca agaagatcag    4740
caggaggttt atgcagaaat tatggcagtt ctaaagcatg acgatcagca taccataaat    4800
acccaagaca ttgcatctga tctgtgtcaa ctcagtacac agactgtgtt ctccatgctt    4860
gaccatctca cacagtgggc aaggcacaaa tttcaggcac tgaaagctga gaaatgtcca    4920
cacagcaaat caaacagaaa taaggtagac tcaatggtat ctactgtgga ttatgaagac    4980
tatcagagtg taacccgttt tctagacctc ataccccagg atactctggc agtagcttcc    5040
tttcgctcca aagcatacac acgagctgta atgcactttg aatcatttat tacagaaaag    5100
aagcaaaata ttcaggaaca tcttggattt ttacagaaat tgtatgctgc tatgcatgaa    5160
cctgatggag tggccggagt cagtgcaatt agaaaggcag aaccatctct aaaagaacag    5220
atccttgaac atgaaagcct tggcttgctg agggatgcca ctgcttgtta tgacagggct    5280
attcagctag aaccagacca gatcattcat tatcatggtg tagtaaagtc catgttaggt    5340
cttggtcagc tgtctactgt tatcactcag gtgaatggag tgcatgctaa caggtccgag    5400
tggacagatg aattaaacac gtacagagtg gaagcagctt ggaaattgtc acagtgggat    5460
```

```
ttggtggaaa actatttggc agcagatgga aaatctacaa catggagtgt cagactggga    5520
cagctattat tatcagccaa aaaagagat atcacagctt tttatgactc actgaaacta     5580
gtgagagcag aacaaattgt acctctttca gctgcaagct tgaaagagg ctcctaccaa     5640 cgaggatatg aatatattgt gagattgcac atgttatgtg agttggagca tagcatcaaa   5700
ccacttttcc agcattctcc aggtgacagt tctcaagaag attctctaaa ctgggtagct   5760
cgactagaaa tgacccagaa ttcctacaga gccaaggagc ctatcctggc tctccggagg   5820
gctttactaa gcctcaacaa agaccagat tacaatgaaa tggttggaga atgctggctg    5880
cagagtgcca gggtagctag aaaggctggt caccaccaga cagcctacaa tgctctcctt   5940
aatgcagggg aatcacgact cgctgaactg tacgtggaaa gggcaaagtg gctctggtcc   6000
aagggtgatg ttcaccaggc actaattgtt cttcaaaaag gtgttgaatt atgttttcct   6060
gaaaatgaaa ccccacctga gggtaagaac atgttaatcc atggtcgagc tatgctacta   6120
gtgggccgat ttatggaaga aacagctaac tttgaaagca atgcaattat gaaaaaatat   6180
aaggatgtga ccgcgtgcct gccagaatgg gaggatgggc attttacct tgccaagtac    6240 tatgacaaat tgatgcccat ggtcacagac aacaaaatgg aaaagcaagg tgatctcatc   6300
cggtatatag ttcttcattt tggcagatct ctacaatatg gaaatcagtt catatatcag   6360
tcaatgccac gaatgttaac tctatggctt gattatggta caaaggcata tgaatgggaa   6420
aaagctggcc gctccgatcg tgtacaaatg aggaatgatt tgggtaaaat aaacaaggtt   6480
atcacagagc atacaaacta tttagctcca tatcaatttt tgactgcttt ttcacaattg   6540
atctctcgaa tttgtcattc tcacgatgaa gttttgttg tcttgatgga aataatagcc    6600
aaagtatttc tagcctatcc tcaacaagca atgtggatga tgcagctgt gtcaaagtca    6660 tcttatccca tgcgtgtgaa cagatgcaag gaaatcctca ataaagctat tcatatgaaa   6720
aaatccttag agaagtttgt tggagatgca actcgcctaa cagataagct tctagaattg   6780
tgcaataaac cggttgatgg aagtagttcc acattaagca tgagcactca ttttaaaatg   6840
cttaaaaagc tggtagaaga agcaacattt agtgaaatcc tcattcctct acaatcagtc   6900
atgataccta cacttccatc aattctgggt acccatgcta accatgctag ccatgaacca   6960
tttcctggac attgggccta tattgcaggg tttgatgata tggtggaaat tcttgcttct   7020
cttcagaaac caaagaagat ttcttttaaaa ggctcagatg gaaagttcta catcatgatg   7080
tgtaagccaa aagatgacct gagaaaggat tgtagactaa tggaattcaa ttccttgatt   7140
aataagtgct taagaaaaga tgcagagtct cgtagaagag aacttcatat tcgaacatat   7200
gcagttattc cactaaatga tgaatgtggg attattgaat gggtgaacaa cactgctggt   7260
ttgagaccta ttctgaccaa actatataaa gaaaagggag tgtatatgac aggaaaagaa   7320
cttcgccagt gtatgctacc aaagtcagca gctttatctg aaaaactcaa agtattccga   7380
gaatttctcc tgcccaggca tcctcctatt tttcatgagt ggtttctgag aacattccct   7440
gatcctacat catggtacag tagtagatca gcttactgcc gttccactgc agtaatgtca   7500
atggttggtt atattctggg gcttggagac cgtcatggtt aaaatattct ctttgattct   7560
ttgactggtg aatgcgtaca tgtagatttc aattgtcttt tcaataaggg agaaaccttt   7620
gaagttccag aaattgtgcc atttcgcctg actcataata tggttaatgg aatgggtcct   7680
atgggaacag agggtctttt tcgaagagca tgtgaagtta caatgaggct gatgcgtgat   7740
cagcgagagc ctttaatgag tgtcttaaag acttttctac atgatcctct tgtggaatgg   7800
agtaaaccag tgaaagggca ttccaaagcg ccactgaatg aaactggaga agttgtcaat   7860
```

```
gaaaaggcca agaccatgt tcttgacatt gagcagcgac tacaaggtgt aatcaagact    7920
cgaaatagag tgacaggact gccgttatct attgaaggac atgtgcatta ccttatacaa    7980
gaagctactg atgaaaactt actatgccag atgtatcttg gttggactcc atatatgtga    8040
aatgaaatta tgtaaaagaa tatgttaata atctaaaagt aatgcatttg gtatgaatct    8100
gtggttgtat ctgttcaatt ctaaagtaca acataaattt acgttctcag caactgttat    8160
ttctctctga tcattaatta tatgtaaaat aatatacatt cagttattaa gaaataaact    8220
gctttcttaa taaaaaaaaa aaaaaaaaaa aaaaaaaaaa aaaaa                    8265
```

<210> SEQ ID NO 5
<211> LENGTH: 2654
<212> TYPE: PRT
<213> ORGANISM: Xenopus laevis

<400> SEQUENCE: 5

```
Met Ala Thr Asp Pro Gly Leu Glu Met Ala Ser Met Ile Pro Ala Leu
 1               5                  10                  15

Arg Glu Leu Ala Ser Ala Gly Ala Glu Glu Tyr Asn Thr Thr Val Gln
             20                  25                  30

Lys Pro Arg Gln Ile Leu Cys Gln Phe Ile Asp Arg Ile Leu Thr Asp
         35                  40                  45

Val Asp Val Val Ala Val Glu Leu Ser Lys Asn Thr Asp Ser Gln Pro
     50                  55                  60

Ser Ser Val Met Leu Leu Asp Phe Ile Gln His Ile Met Lys Ser Thr
 65                  70                  75                  80

Pro Leu Met Phe Leu Ser Ala Asn Asn Gly Asp Gln Ser Ala Glu Thr
                 85                  90                  95

Asn Gln Asn Cys Val Ala Phe Ser Asn Trp Ile Ile Ser Arg Leu Leu
            100                 105                 110

Arg Ile Gly Ala Thr Pro Ser Cys Lys Ala Leu His Arg Lys Ile Ala
        115                 120                 125

Glu Val Ile Arg Ser Leu Leu Phe Leu Phe Lys Asn Lys Ser Ser Phe
    130                 135                 140

Leu Phe Gly Val Phe Thr Lys Asp Leu Leu His Leu Phe Glu Asp Leu
145                 150                 155                 160

Ile Tyr Ile His Glu Gln Asn Met Glu Lys Ser Val Val Trp Pro Val
                165                 170                 175

Thr Ile Ser Arg Phe Leu Ser Asn Ala Ser Glu Asn Gln Thr Tyr Leu
            180                 185                 190

Arg Cys Thr Gln Phe Gln Leu Leu Asn Met Gln Asn Ile Glu Pro Leu
        195                 200                 205

Glu Ser Thr Leu Leu Met Val Leu Met Asp Asn Glu His Asp Ile Ser
    210                 215                 220

Pro Val Phe Phe Gln Arg Gln Asn Leu Leu Leu Trp Gly Ile Gly Cys
225                 230                 235                 240

Ser Leu Leu Asp Tyr Gly Ser Thr Pro Leu Lys Ile Gln Ala Leu His
                245                 250                 255

Phe Leu Arg Gln Leu Ile Lys Leu Gly Gly Pro Pro Glu Gln Gly Ala
            260                 265                 270

Tyr Phe Phe Phe Ile Val Phe Phe Gly Ile Leu Thr Cys Ile Lys Asp
        275                 280                 285

Met Asp Leu Glu Glu Val Ser Leu Tyr Glu Met Pro Leu Leu Lys Leu
    290                 295                 300
```

```
Val Lys Val Leu Phe Pro Phe Glu Ser Lys Ser Tyr Leu Asn Ile Glu
305                 310                 315                 320

Pro Val Tyr Leu Asn Met Leu Leu Glu Lys Leu Ala Ala Leu Phe Asp
            325                 330                 335

Gly Gly Ile Leu Ser Asn Ile Gln Ser Ala Pro Leu Lys Glu Ala Leu
            340                 345                 350

Cys Tyr Met Val His Tyr Phe Leu Ser Ile Val Pro Pro Gly Tyr Glu
            355                 360                 365

Ser Ala Lys Glu Val Arg Glu Ala His Val Arg Cys Ile Cys Arg Ala
370                 375                 380

Phe Val Asp Val Leu Gly Leu Gln Ser Lys Gln Glu Tyr Leu Val Cys
385                 390                 395                 400

Pro Leu His Glu Ala Leu Arg Ile Glu Asn Leu Val Phe Met Gln Gln
                405                 410                 415

Gln Arg Met Gln Pro Leu Ser Thr Asp Ser Glu Gly Gly Gly Ser Ser
            420                 425                 430

Ser Ser Asp Glu Val Gln Glu Lys Arg Pro Arg Leu Ser Leu Thr Ala
            435                 440                 445

Lys Pro Leu Arg Arg Asn Thr Pro Ser Val Pro Ala Pro Val Asp Met
450                 455                 460

Lys Thr Lys Ser Ile Leu Trp Lys Ala Val Ser Ala Lys Phe Ser Ser
465                 470                 475                 480

Ile Leu Cys Lys Leu Glu Gly Asp Glu Val Thr Asp Glu Met Val
                485                 490                 495

Ser Leu Leu Glu Gly Leu Asn Thr Thr Val Arg Val Ala Ala Leu Asn
                500                 505                 510

Thr Val His Ile Phe Thr Asn Asp Ser Thr Asp Thr Asp Gln Leu Val
            515                 520                 525

Ser Asp Leu Ser Asn Thr Ser Gly Ile Gln Ser Val Glu Ile Val Pro
530                 535                 540

His Val Phe Trp Leu Ser Pro Glu Asp Ile Leu Lys Ile Leu Lys Ile
545                 550                 555                 560

Cys Arg Lys Val Leu Asp Ser Ala His Gln Arg Ala Asn Ile Asn Asp
                565                 570                 575

Ile Leu Met Lys Ile Ile Lys Ile Phe Asp Ala Ile Leu Tyr Ile His
            580                 585                 590

Ala Gly Asn Arg Leu Asn Asp Gln Thr Leu Lys Asp Leu Cys Ser Met
            595                 600                 605

Ile Ser Leu Pro Trp Leu Gln Asn His Ser Asn His Ala Ser Phe Lys
            610                 615                 620

Val Ala Ser Phe Asp Pro Thr Leu Met Thr Ile Ser Glu Arg Ile Gly
625                 630                 635                 640

Gln His Tyr Ser Pro Glu Ile Gln Ser Gln Leu Val Phe Leu Leu Cys
            645                 650                 655

Leu Phe Pro Lys Met Leu Cys Pro Glu Trp Arg Leu Ala Val Tyr Gln
                660                 665                 670

Trp Ala Leu Asp Ser Pro His Glu Ile Val Arg Ala Arg Cys Ile Lys
            675                 680                 685

Gly Phe Pro Val Leu Leu Cys Asn Val Ser Gln Gln Gly Tyr Gly Pro
            690                 695                 700

Ile Pro Lys Ile Leu Ile Asp Cys Leu Asn Asp Ala Ser Glu Leu Val
705                 710                 715                 720

Lys Lys Glu Leu Ala Asn Ser Val Gly Met Phe Ala Ser Gly Leu Ala
                725                 730                 735
```

```
Cys Gly Phe Glu Leu Gln Tyr Ser Pro Thr Ala Pro Thr Ala Ala Glu
            740                 745                 750

Ser Glu Phe Leu Cys Ser Ser Leu Thr Val Thr Ala Leu Pro Ser Ser
            755                 760                 765

Lys Leu Ser Arg Met Thr Ala Ser Ala Leu Lys Pro Phe Leu Ala Leu
            770                 775                 780

Leu Asn Arg Asn Met Pro Ser Ser Val Lys Met Ala Phe Ile Glu Asn
785                 790                 795                 800

Met Pro Met Leu Phe Ala His Leu Ser Leu Glu Lys Asp Asp Leu Asp
                805                 810                 815

Ser Arg Thr Val Ile Glu Ser Leu Leu Asn Leu Met Glu Asp Pro Asp
                820                 825                 830

Lys Asp Val Arg Thr Ala Phe Ser Gly Asn Ile Lys His Leu Leu Ala
                835                 840                 845

Cys Ala Asp Cys Glu Asp Gly Tyr Leu Lys Glu Ile Val Val Ser Arg
            850                 855                 860

Met Lys Lys Ala Tyr Thr Asp Ala Lys Met Ser Arg Asp Asn Glu Met
865                 870                 875                 880

Lys Asp Thr Leu Ile Leu Thr Thr Gly Asp Ile Gly Arg Ala Ala Lys
                885                 890                 895

Gly Glu Leu Val Pro Phe Ala Leu Leu His Leu Leu Cys Leu Leu
                900                 905                 910

Ser Lys Ser Pro Cys Val Ala Gly Ala Ser Tyr Thr Glu Ile Arg Ser
            915                 920                 925

Leu Ala Ala Lys Ser Thr Ser Leu His Ile Phe Phe Ser Gln Tyr
            930                 935                 940

Lys Lys Pro Ile Cys Gln Phe Leu Ile Glu Ser Leu His Ser Ser Gln
945                 950                 955                 960

Ala Ala Leu Leu Thr Asn Thr Pro Gly Arg Ser Ser Glu Met Gln Lys
                965                 970                 975

Gln Glu Ala Thr His His Arg Glu Ala Ala Leu Asp Ile Leu Ser Glu
            980                 985                 990

Ile Ala Asn Val Phe Asp Phe Pro Asp Leu Asn Arg Phe Leu Thr Arg
            995                 1000                1005

Thr Leu Gln Leu Leu Pro Tyr Leu Ala Ala Lys Ala Ser Pro Thr
    1010                1015                1020

Ala Ser Thr Leu Ile Arg Thr Ile Ala Lys Gln Leu Asn Val Asn Arg
1025                1030                1035                1040

Arg Glu Ile Leu Ile Asn Asn Phe Lys Tyr Ile Phe Ser His Leu Val
                1045                1050                1055

Cys Ser Cys Thr Lys Asp Glu Leu Glu Lys Ser Leu His Tyr Leu Lys
            1060                1065                1070

Asn Glu Thr Glu Ile Glu Leu Gly Ser Leu Leu Arg Gln Asp Tyr Gln
            1075                1080                1085

Gly Leu His Asn Glu Leu Leu Leu Arg Leu Gly Glu His Tyr Gln Gln
            1090                1095                1100

Val Phe Ser Gly Leu Ser Ile Leu Ala Thr Tyr Ala Ser Asn Asp Asp
1105                1110                1115                1120

Pro Tyr Gln Gly Pro Arg Asn Phe Ala Lys Pro Glu Ile Met Ala Asp
                1125                1130                1135

Tyr Leu Gln Pro Lys Leu Leu Gly Ile Leu Ala Phe Phe Asn Met His
                1140                1145                1150

Leu Leu Ser Ser Ser Ile Gly Ile Glu Asp Lys Lys Met Ala Leu Asn
```

```
                      1155                1160                1165
Ser Leu Val Ser Leu Met Lys Leu Met Gly Pro Lys His Ile Ser Ser
        1170                1175                1180

Val Arg Val Lys Met Met Thr Thr Leu Arg Thr Gly Leu Arg Tyr Lys
1185                1190                1195                1200

Glu Glu Phe Pro Gly Leu Cys Cys Ser Ala Trp Asp Leu Phe Val Arg
                1205                1210                1215

Cys Leu Asp Gln Ala Tyr Leu Gly Pro Leu Leu Ser His Val Ile Val
            1220                1225                1230

Ala Leu Leu Pro Leu Leu His Ile Gln Pro Lys Glu Thr Val Ala Val
            1235                1240                1245

Phe Arg Tyr Leu Ile Val Glu Asn Arg Asp Ala Val Gln Asp Phe Leu
            1250                1255                1260

His Glu Ile Tyr Phe Leu Pro Asp His Pro Glu Leu Lys Glu Ile Gln
1265                1270                1275                1280

Lys Val Leu Gln Glu Tyr Arg Lys Glu Thr Thr Lys Ser Thr Asp Leu
                1285                1290                1295

Gln Thr Ala Met Gln Leu Ser Ile Arg Ala Ile Gln His Glu Asn Val
            1300                1305                1310

Asp Val Arg Met His Ala Leu Thr Ser Leu Lys Glu Thr Leu Tyr Lys
            1315                1320                1325

Asn Gln Ala Lys Leu Leu Gln Tyr Ser Thr Asp Ser Glu Thr Val Glu
            1330                1335                1340

Pro Val Ile Ser Gln Leu Val Thr Val Leu Leu Ile Gly Cys Gln Asp
1345                1350                1355                1360

Ala Asn Pro Gln Ala Arg Leu Phe Cys Gly Glu Cys Leu Gly Gln Leu
                1365                1370                1375

Gly Ala Ile Asp Pro Gly Arg Leu Asp Phe Ser Pro Ser Glu Thr Gln
            1380                1385                1390

Gly Lys Gly Phe Thr Phe Val Ser Gly Val Glu Asp Ser Asp Phe Ala
            1395                1400                1405

Tyr Glu Leu Leu Thr Glu Gln Thr Arg Ala Phe Leu Ala Tyr Ala Asp
            1410                1415                1420

Asn Val Arg Ala Gln Asp Ser Ala Ala Tyr Ala Ile Gln Glu Leu Leu
1425                1430                1435                1440

Ser Ile Phe Glu Cys Lys Glu Gly Arg Thr Asp Cys Pro Gly Arg Arg
                1445                1450                1455

Leu Trp Arg Arg Phe Pro Glu His Val Gln Glu Ile Leu Glu Pro His
            1460                1465                1470

Leu Asn Thr Arg Tyr Lys Ser Ser Arg Lys Ala Val Asn Trp Ser Arg
            1475                1480                1485

Val Lys Lys Pro Ile Tyr Leu Ser Lys Leu Gly Asn Asn Phe Ala Asp
            1490                1495                1500

Trp Ser Ala Thr Trp Ala Gly Tyr Leu Ile Thr Lys Val Arg His Glu
1505                1510                1515                1520

Leu Ala Arg Arg Val Phe Ser Cys Cys Ser Ile Met Met Lys His Asp
                1525                1530                1535

Phe Lys Val Thr Ile Tyr Leu Leu Pro His Ile Leu Val Tyr Val Leu
            1540                1545                1550

Leu Gly Cys Asn Lys Glu Asp Gln Gln Glu Val Tyr Ala Glu Ile Met
            1555                1560                1565

Ala Val Leu Lys His Glu Asp Pro Leu Met Arg Arg Leu Gln Asp Ser
            1570                1575                1580
```

-continued

Ala Ser Asp Leu Ser Gln Leu Ser Thr Gln Thr Val Phe Ser Met Leu
1585                1590                1595                1600

Asp His Leu Thr Gln Trp Ala Arg Glu Lys Phe Gln Ala Leu Asn Ala
            1605                1610                1615

Glu Lys Thr Asn Pro Lys Pro Gly Thr Arg Gly Glu Pro Lys Ala Val
        1620                1625                1630

Ser Asn Glu Asp Tyr Gly Glu Tyr Gln Asn Val Thr Arg Phe Leu Asp
    1635                1640                1645

Leu Ile Pro Gln Asp Thr Leu Ala Val Ala Ser Phe Arg Ser Lys Ala
1650                1655                1660

Tyr Thr Arg Ala Leu Met His Phe Glu Ser Phe Ile Met Glu Lys Lys
1665                1670                1675                1680

Gln Glu Ile Gln Glu His Leu Gly Phe Leu Gln Lys Leu Tyr Ala Ala
            1685                1690                1695

Met His Glu Pro Asp Gly Val Ala Gly Val Ser Ala Ile Arg Lys Lys
        1700                1705                1710

Glu Ala Ser Leu Lys Glu Gln Ile Leu Glu His Glu Ser Ile Gly Leu
    1715                1720                1725

Leu Arg Asp Ala Thr Ala Cys Tyr Asp Arg Ala Ile Gln Leu Lys Pro
1730                1735                1740

Glu Glu Ile Ile His Tyr His Gly Val Val Lys Ser Met Leu Gly Leu
1745                1750                1755                1760

Gly Gln Leu Ser Thr Val Ile Thr Gln Val Asn Gly Ile Leu Asn Ser
            1765                1770                1775

Arg Ser Glu Trp Thr Ala Glu Leu Asn Thr Tyr Arg Val Glu Ala Ala
        1780                1785                1790

Trp Lys Leu Ser Gln Trp Asp Leu Val Glu Glu Tyr Leu Ser Ala Asp
    1795                1800                1805

Arg Lys Ser Thr Thr Trp Ser Ile Arg Leu Gly Gln Leu Leu Leu Ser
1810                1815                1820

Ala Lys Lys Gly Glu Arg Asp Met Phe Tyr Glu Thr Leu Lys Val Val
1825                1830                1835                1840

Arg Ala Glu Gln Ile Val Pro Leu Ser Ala Ala Ser Phe Glu Arg Gly
            1845                1850                1855

Ser Tyr Gln Arg Gly Tyr Glu Tyr Ile Val Arg Leu His Met Leu Cys
        1860                1865                1870

Glu Leu Glu His Ser Val Lys Met Phe Leu Gln Lys Pro Ser Val Glu
    1875                1880                1885

Pro Ala Val Asp Ser Leu Asn Leu Pro Ala Arg Leu Glu Met Thr Gln
1890                1895                1900

Asn Ser Tyr Arg Ala Arg Glu Pro Ile Leu Ala Val Arg Arg Ala Leu
1905                1910                1915                1920

Gln Thr Ile Asn Lys Arg Pro Asn His Ala Asp Met Ile Gly Glu Cys
            1925                1930                1935

Trp Leu Gln Ser Ala Arg Val Ala Arg Lys Ala Gly His His Gln Thr
        1940                1945                1950

Ala Tyr Asn Ala Leu Leu Asn Ala Gly Glu Ser Arg Leu Ser Glu Leu
    1955                1960                1965

Asn Val Glu Arg Ala Lys Trp Leu Trp Ser Lys Gly Asp Val His Gln
1970                1975                1980

Ala Leu Ile Val Leu Gln Lys Gly Ala Glu Leu Phe Leu Ser Ser Thr
1985                1990                1995                2000

Ser Ala Pro Pro Glu Gln Gln Leu Ile His Gly Arg Ala Met Leu Leu
            2005                2010                2015

-continued

Val Gly Arg Leu Met Glu Glu Thr Ala Asn Phe Glu Ser Asn Ala Val
                2020                2025                2030

Met Lys Lys Tyr Lys Asp Val Thr Ala Leu Leu Pro Glu Trp Glu Asp
                2035                2040                2045

Gly His Phe Tyr Leu Ala Lys Tyr Tyr Asp Lys Leu Met Pro Met Val
                2050                2055                2060

Thr Asp Asn Lys Met Glu Lys Gln Gly Asp Leu Ile Arg Tyr Ile Val
2065                2070                2075                2080

Leu His Phe Gly Arg Ser Leu Gln Phe Gly Asn Gln Tyr Ile Tyr Gln
                2085                2090                2095

Ser Met Pro Arg Met Leu Ser Leu Trp Leu Asp Phe Gly Ala Lys Val
                2100                2105                2110

Tyr Glu Trp Glu Lys Ala Gly Arg Ala Asp Arg Leu Gln Met Lys Asn
                2115                2120                2125

Glu Leu Met Lys Ile Asn Lys Val Ile Ser Asp His Lys Asn Gln Leu
                2130                2135                2140

Ala Pro Tyr Gln Phe Leu Thr Ala Phe Ser Gln Leu Ile Ser Arg Ile
2145                2150                2155                2160

Cys His Ser His Asp Glu Val Phe Ala Val Leu Met Glu Ile Val Ala
                2165                2170                2175

Lys Val Phe Val Ala Tyr Pro Gln Gln Ala Met Trp Met Met Thr Ala
                2180                2185                2190

Val Ser Lys Ser Ser Tyr Pro Met Arg Val Asn Arg Cys Lys Glu Ile
                2195                2200                2205

Leu Glu Lys Ala Ile His Met Lys Pro Ser Leu Gly Lys Phe Ile Gly
                2210                2215                2220

Asp Ala Thr Arg Leu Thr Asp Lys Leu Leu Glu Leu Cys Asn Lys Pro
2225                2230                2235                2240

Val Asp Gly Asn Thr Ser Thr Leu Ser Met Asn Ile His Phe Lys Met
                2245                2250                2255

Leu Lys Lys Leu Val Glu Glu Thr Thr Phe Ser Glu Ile Leu Ile Pro
                2260                2265                2270

Leu Gln Ser Val Met Ile Pro Thr Leu Pro Ser Thr Ala Gly Lys Arg
                2275                2280                2285

Asp His Ala Asp His Asp Pro Phe Pro Gly His Trp Ala Tyr Leu Ser
                2290                2295                2300

Gly Phe Asp Asp Ala Val Glu Ile Leu Pro Ser Leu Gln Lys Pro Lys
2305                2310                2315                2320

Lys Ile Ser Leu Lys Gly Ser Asp Gly Lys Ser Tyr Ile Met Met Cys
                2325                2330                2335

Lys Pro Lys Asp Asp Leu Arg Lys Asp Cys Arg Leu Met Glu Phe Asn
                2340                2345                2350

Ser Leu Ile Asn Lys Cys Leu Arg Lys Asp Ala Glu Ser Arg Arg Arg
                2355                2360                2365

Glu Leu His Ile Arg Thr Tyr Ala Val Ile Pro Leu Asn Asp Glu Cys
                2370                2375                2380

Gly Ile Ile Glu Trp Val Asn Asn Thr Ala Gly Phe Arg Asn Ile Leu
2385                2390                2395                2400

Ile Lys Leu Tyr Lys Glu Lys Gly Ile Tyr Met Gly Gly Lys Glu Leu
                2405                2410                2415

Arg Gln Cys Met Leu Pro Lys Ser Ala Pro Leu Gln Glu Lys Leu Lys
                2420                2425                2430

Val Phe Lys Glu Ala Leu Leu Pro Arg His Pro Pro Leu Phe His Glu

```
                     2435              2440              2445
Trp Phe Leu Arg Thr Phe Pro Asp Pro Thr Ser Trp Tyr Asn Ser Arg
    2450              2455              2460

Ser Ala Tyr Cys Arg Ser Thr Ala Val Met Ser Met Val Gly Tyr Ile
2465              2470              2475              2480

Leu Gly Leu Gly Asp Arg His Gly Glu Asn Ile Leu Phe Asp Ser Leu
                2485              2490              2495

Thr Gly Glu Cys Val His Val Asp Phe Asn Cys Leu Phe Asn Lys Gly
            2500              2505              2510

Glu Thr Phe Glu Val Pro Glu Ile Val Pro Phe Arg Leu Thr His Asn
        2515              2520              2525

Met Val Asn Gly Met Gly Pro Met Gly Thr Glu Gly Leu Phe Arg Arg
    2530              2535              2540

Ala Cys Glu Val Ile Met Arg Leu Met Arg Glu Gln Arg Glu Ser Leu
2545              2550              2555              2560

Met Ser Val Leu Lys Pro Phe Leu His Asp Pro Leu Val Glu Trp Ser
                2565              2570              2575

Lys Pro Ala Arg Gly Ser Ser Lys Gly Gln Val Asn Glu Thr Gly Glu
            2580              2585              2590

Val Met Asn Glu Lys Ala Lys Thr His Val Leu Asp Ile Glu Gln Arg
        2595              2600              2605

Leu Gln Gly Val Ile Lys Thr Arg Asn Arg Val Lys Gly Leu Pro Leu
    2610              2615              2620

Ser Ile Glu Gly His Val His Tyr Leu Ile Gln Glu Ala Thr Asp Glu
2625              2630              2635              2640

Asn Leu Leu Ser Gln Met Tyr Leu Gly Trp Ala Pro Tyr Met
                2645              2650

<210> SEQ ID NO 6
<211> LENGTH: 8273
<212> TYPE: DNA
<213> ORGANISM: Xenopus laevis

<400> SEQUENCE: 6
ttctagctct gggactgagc tgctaccatg gctactgacc ccggtcttga aatggcctct      60
atgatcccgg ccttgcgtga acttgccagt gccggggcag aggaatataa cacaactgtt     120
cagaaaccaa gacaaatcct tgccagtttt atagaccgga ttctgacaga tgtggacgtt     180
gttgctgtgg agcttttcaaa gaatactgat tctcagccaa gttctgtgat gttgctggat     240
tttattcaac acattatgaa atctacccca ttaatgtttc tcagtgcaaa taacggtgat     300
cagtctgctg aaaccaatca gaactgtgtt gcatttagca actggatcat ttcccggctc     360
ttacgcattg gggctacgcc aagctgcaaa gctttgcata gaaaaatcgc tgaagtcatc     420
cgctccctgc ttttctttt caaaaacaag agttcctttc tatttggtgt ttttactaaa     480
gatttattac atctctttga agatcttatc tacatacatg aacaaacat ggagaaatcc     540 gtagtttggc ctgtgaccat ttctagattt ttaagcaatg catcagaaaa ccaaacttac     600
ttaagatgca ctcaatttca gttgttgaac atgcagaaca ttgagccttt agaatccact     660
ctgctaatgg ttttgatgga taacgaacat gatatttctc cagtgttttt ccaaaggcag     720
aacctcctcc tctggggcat tgggtgctcc ctcttggact atggaagtac accactgaag     780
atacaggcat tgcattttt aagacaacta ataaaattag gtggtccacc agaacagggt     840
gcatattttt tcttcattgt gttttttggg atactaactt gtataaaaga catggattta     900
gaagaagtgt ctctttatga gatgccactg ttgaaattgg taaaggtttt gttcccattt     960
```

-continued

```
gaatcaaaat cttacctaaa cattgaacct gtctatctga atatgttgct ggagaaactt    1020
gctgctctct ttgatggagg tatcttgagt aatattcagt cagctccctt gaaagaagct    1080
ctttgctata tggtccatta cttccttagc attgtgcctc cgggctatga atctgccaaa    1140
gaagtccgag aggcacatgt tcgctgcatc tgtagagctt ttgttgatgt ccttggactt    1200
cagagcaagc aagaatactt ggtctgcccc cttcatgaag cattaagaat agaaaacctg    1260
gtgttcatgc agcagcagcg catgcagccc ctaagcacag actcagaggg tggtgggagc    1320
agcagcagcg atgaagtgca agagaaacga ccacgtttga gtctaactgc aaagcctcta    1380
agaagaaaca caccatcagt gcctgctcct gtggatatga agacaaagag catactatgg    1440
aaagcagtga gtgcgaaatt ctcctctatt ttgtgcaaac tggaaggtga cgaagttaca    1500
gatgaagaga tggtttcttt attggagggt cttaatacaa ctgtacgtgt tgctgctctc    1560
aatacagttc atatcttcac taatgattcc acagatactg atcagttagt atctgacttg    1620
agcaatactt ctggcattca gtcggtagaa atagtacctc acgttttctg gctcagtcca    1680
gaggatattc taaaaatact taaaatttgt agaaaggttc ttgattctgc acaccagaga    1740
gccaatataa atgacattct gatgaagata ataaaaatat tgatgcaat actctacatt     1800 catgcaggaa acagattaaa tgaccaaact cttaaggatt tgtgcagcat gatctcatta    1860
ccctggcttc agaatcattc aaatcatgct tcctttaaag tggcatcatt tgacccaaca    1920
ttgatgacca taagtgagcg gattggccaa cattactcac ctgaaattca gtctcaactt    1980
gttttcctcc tgtgcctgtt tccaaaaatg ttatgccctg agtggagatt agctgtgtac    2040
caatgggcat tggatagccc acatgagatt gttcgtgccc gttgcatcaa aggattccct    2100
gttcttctgt gcaatgttag ccagcagggg tatggtccaa ttcccaagat tttaatcgac    2160
tgtttgaatg atgcctctga gctggtgaag aaggagttag ccaactcagt gggtatgttt    2220
gcctccggcc ttgcttgcgg ttttgagctg caatattccc caacggcacc tactgcagca    2280
gaatctgagt tcctttgtag cagcctgaca gttactgctt taccctcatc gaaactttct    2340
cgtatgaccg cctctgcatt aaaaccattc ctggcactgc ttaatcgaaa catgccaagc    2400
tccgtcaaaa tggcatttat tgaaaatatg cccatgctgt ttgctcacct ctctcttgag    2460
aaagatgatt tggattcccg aactgtgatt gaatcattgt taaacctaat ggaggaccca    2520
gacaaggatg taaggacagc tttcagtggg aacatcaaac acctgttggc gtgtgcagac    2580
tgtgaggacg gatatctaaa ggagattgta gtctcaagga tgaaaaaagc atatacagat    2640
gccaagatgt cgcgtgacaa tgagatgaag gacactctca ttcttacaac tggggatata    2700
ggaagggcag caaaaggaga gttggtacca tttgcactgt tgcatctgct gcattgcctg    2760
ctgtctaaat ccccatgtgt ggcaggtgct tcttacacag aaatccgatc tcttgcagca    2820
gcaaagtcca ccagtctgca tatcttttt agccagtaca agaaaccgat tgtcagttc     2880 cttatagaat cgcttcactc aagccaggca gcccttctga ccaacacacc tggccgcagc    2940
agtgaaatgc agaagcagga ggcaacacat cataggaag ctgcacttga catcttatcc     3000
gaaatagcaa atgtatttga tttcccagac ttaaaccgct ttttaacgag actttgcaa    3060 cttttgcttc catatcttgc tgccaaagct agtccaacag cctctactct gataagaacg    3120
attgccaaac aacttaatgt gaatcgaagg gagatcctga tcaataactt caagtatata    3180
ttctctcact tggtttgttc ttgcacaaaa gatgagctgg aaaagtcgct tcattaccta    3240
aagaatgaaa cagaaattga gctgggtagt ttactgagac aggactacca gggactgcac    3300
aatgaactac ttttgcgcct gggtgagcac tatcagcagg tctttagtgg gctgtccata    3360
```

```
ttagcaacat atgcatccaa cgatgatcca tatcagggac ctaggaattt tgcaaagcca    3420
gaaataatgg cagattattt gcaaccaaag ctttaggaa ttttggcttt ctttaatatg    3480
cacctgttga gctccagcat tggcattgaa gacaagaaaa tggccttgaa cagtctggtt    3540
tctttaatga aactgatggg accaaagcat ataagttccg ttagggtcaa gatgatgacg    3600
accttgagaa ctggcctacg ttataaagag gaatttccgg ggctttgctg cagtgcatgg    3660
gacttgtttg ttcgctgcct ggatcaagcc tatctgggcc cgctcctcag tcatgtgatt    3720
gttgcactgt tgcctctgtt gcacatccag cctaaagaaa ctgttgctgt gttccgctat    3780
ctcatagtag agaacaggga tgctgttcag gatttccttc atgaaatata ttttctgcct    3840
gatcatccag aattgaaaga aatccagaag gttctacaag aatacaggaa agaaaccacc    3900
aaaagcacag atctgcagac agccatgcag ctgtctattc gagccattca gcatgaaaat    3960
gtggatgttc gcatgcatgc ccttactagt ctgaagaaa cactctacaa gaaccaggct    4020
aaactgttgc agtattcaac agacagtgaa actgtagaac cagttatctc ccagctggta    4080
acagttctct taattggatg ccaagatgcc aatccacaag cccgtctatt ttgtggtgaa    4140
tgccttggcc aacttggagc cattgatcct gggagattgg atttctcacc cagtgaaaca    4200
caagggaaag gttttacttt tgtttcagga gttgaagatt cagactttgc ctatgagttg    4260
ctcacagagc aaactagagc atttcttgcc tatgctgata atgtccgcgc ccaggactct    4320
gctgcctatg ctatacagga gcttctctct atcttcgagt gcaaagaagg aaggactgat    4380
tgtcctgggc gtaggctgtg gaggagattc ccagaacatg ttcaagaaat attggagcca    4440
catcttaata ctagatacaa gagttccaga aaggctgtaa actggtccag agtgaaaaag    4500
cccatttatt tgagcaagtt aggaaataac tttgcagact ggtcagcaac atgggcaggt    4560
tacctcataa ctaaggttcg acatgagctt gccaggagag ttttcagctg ttgtagtata    4620
atgatgaagc atgacttcaa agtgaccatt tatctgctcc cacatatttt ggtctatgtt    4680
ttgttgggat gtaacaaaga agatcagcaa gaggtatatg cagaaattat ggcagtgtta    4740
aagcatgaag atccactaat gcgtcggtta caggacagcg cctcagatct gagtcagctc    4800
agcacccaaa cagtcttttc aatgcttgat catcttactc agtgggcacg ggagaaattc    4860
caggcactaa atgctgagaa aacaaacccc aaaccaggaa ccagagggga accaaaggca    4920
gtgtctaatg aagactatgg agagtatcag aatgtaacaa ggttttttaga tcttataccg    4980
caggatactt tggctgttgc ttcctttcgt tccaaagctt atactagagc tctcatgcat    5040
tttgaatcct ttataatgga aaagaaacaa gaaattcagg agcaccttgg atttcttcag    5100
aaactgtatg ctgctatgca tgagccagat ggagtagctg gggtaagcgc cattcgcaag    5160
aaagaagctt ctctgaaaga acagatcttg gagcatgaaa gtattggtct gttgagagat    5220
gccactgctt gctatgatag agctattcag ctaaagcctg aggagataat tcactatcat    5280
ggggtagtga atctatgct tggtcttggc cagttgtcta ctgtaattac gcaagttaac    5340
ggcattttga atagcaggtc ggaatggaca gctgaactaa gcacatacag agtagaagca    5400
gcatggaaac tctcacagtg ggatttagtg gaggaatact tatctgcaga cagaaaatct    5460
accacatgga gcattaggct ggggcaactc ctgctttcag ctaaaaaggg ggagagagat    5520
atgtttatg aaacgctcaa agtagtccga gccgaacaaa ttgttccact gtctgctgcc    5580
agctttgaga ggggctccta ccaacgagga tatgagtaca tagtaaggtt gcacatgtta    5640
tgtgagttgg agcacagtgt aaaaatgttt cttcagaaac cttctgttga gcctgcagta    5700
gactctttaa acttgccagc acggctagaa atgacacaga attcctacag agcaagagag    5760
```

```
cccatttttgg cagttcgcag ggcactacaa acaatcaaca aaaggcctaa tcatgcagat   5820
atgattggtg agtgttggct gcaaagtgct cgagttgcgc gtaaggctgg gcatcaccag   5880
actgcttaca atgctctgct taatgctggg gagtccagac tgtctgagct caatgttgaa   5940
cgggcgaagt ggctctggtc caagggtgat gtacatcaag ctctcattgt tctccagaag   6000
ggagcagaac tgttcctgtc aagtaccagc gctccaccag aacagcagct tatccatggc   6060
agagccatgc tgctggtggg ccgtttgatg aagagactg ccaactttga aagcaacgct    6120
gtgatgaaga aatataaaga tgtaacagca ctgttgcctg aatgggaaga tggccatttt   6180
tatcttgcca agtactatga caaactcatg ccaatggtta ctgataacaa gatggagaag   6240
caaggagact tgatacgata tatagtactt cactttggaa ggtctttaca gttcggaaac   6300
caatatattt atcaatcgat gccacgtatg ctttcacttt ggctggattt tggagctaaa   6360
gtttatgaat gggaaaaagc tggtcgtgct gacagattac aaatgaaaaa tgaattgatg   6420
aaaataaata aggtcatatc tgaccataaa aaccagcttg ctccttatca gttccttaca   6480
gctttctcac agctaatctc cagaatatgt cactctcatg atgaggtgtt tgctgtgttg   6540
atggaaattg tggctaaggt gtttgtggca tacccccagc aggcaatgtg gatgatgact   6600
gctgtgtcta agtcatcata tccaatgcgt gtaaacagat gcaaagagat actcgagaag   6660
gccatacata tgaagccatc cctaggaaaa tttattggag atgcaactcg cctcactgat   6720
aaactactag agctctgcaa taagccggtg gatggaaata ctagcaccct cagtatgaat   6780
atccacttca aaatgctgaa gaaactagta gaagaaacaa catttagtga aatccttatt   6840
cctctacagt ccgtgatgat tcccacccta ccgtctactg cagggaagcg tgaccatgct   6900
gatcatgatc cattccctgg ccactgggct tacctctcag gctttgatga cgcggtagag   6960
attctgcctt ctctccagaa accaagaaaa atttctctaa agggatcaga cggtaaatca   7020
tacattatga tgtgtaaacc aaaagatgat cttagaaagg actgccggct gatggaattt   7080
aactctttaa tcaacaagtg tttacgcaaa gatgcagaat cacgaaggag agagcttcat   7140
attcgaacct atgctgtcat tccactgaat gatgaatgtg aatcataga gtgggtgaat    7200 aatactgcag gattccggaa catattgatc aagctgtaca aggaaaaagg catttacatg   7260
ggtggaaagg aactgcggca gtgtatgctt cccaagaacg caccactaca agaaaagctg   7320
aaagtcttta aggaggccct actgcctcgt cacccccccat tgttccatga atggttttta   7380
agaacatttc ctgatcctac ttcttggtat aacagcagat cagcctattg ccgttccact   7440
gctgtgatgt ctatggtagg ttacatactg ggcctagggg accgccatgg agaaaacatt   7500 cttttttgact cgcttactgg ggaatgtgtc catgtggatt ttaactgcct cttcaacaag   7560
ggtgaaacat ttgaagttcc agagatcgtc cccttccgac taacacataa catggtcaat   7620
ggtatgggcc ccatggggac ggagggactt tttcgacgtg catgtgaggt catcatgagg   7680
ttaatgagag aacagaggga gtcacttatg agtgtgctga acccttttt acatgatcct    7740 ttggtggaat ggagtaaacc agcaagaggg agtagtaaag gtcaagtcaa cgagacagga   7800
gaagtgatga atgaaaaggc caaaacacat gtgcttgaca tagagcagag gctacaaggt   7860
gtgattaaga ccaggaatcg tgtaaaggga cttccgctgt ccattgaagg acatgtccat   7920
tacctgatcc aagaagccac agatgagaac cttctcagcc agatgtactt ggggtgggct   7980
ccgtatatgt gatgctgctc atgtggaaca tctcccattc tgtcagagaa taagtacatt   8040
tgtaaataac tgtaggtgta tatttgtatg aatacattta ttatcaaatt gcaggacaaa   8100
aaaatgtcca ataggtagtt ttattttgat ggaggagtca tgcatctgtt tatataaaac   8160
```

```
attttgtata ctattttcta ttaccaccat ttatgtagcc attaattggt ttggaatact    8220
tttttgaaaa ataaatattg ttatttcttg tacgtttaaa aaaaaaaaaa aaa           8273
```

<210> SEQ ID NO 7
<211> LENGTH: 1522
<212> TYPE: PRT
<213> ORGANISM: Homo sapiens

<400> SEQUENCE: 7

```
Met Ser Arg Asn Asp Lys Glu Pro Phe Phe Val Lys Phe Leu Lys Ser
 1               5                  10                  15

Ser Asp Asn Ser Lys Cys Phe Phe Lys Ala Leu Glu Ser Ile Lys Glu
            20                  25                  30

Phe Gln Ser Glu Glu Tyr Leu Gln Ile Ile Thr Glu Glu Glu Ala Leu
        35                  40                  45

Lys Ile Lys Glu Asn Asp Arg Ser Leu Tyr Ile Cys Asp Pro Phe Ser
    50                  55                  60

Gly Val Val Phe Asp His Leu Lys Lys Leu Gly Cys Arg Ile Val Gly
65                  70                  75                  80

Pro Gln Val Val Ile Phe Cys Met His His Gln Arg Cys Val Pro Arg
                85                  90                  95

Ala Glu His Pro Val Tyr Asn Met Val Met Ser Asp Val Thr Ile Ser
            100                 105                 110

Cys Thr Ser Leu Glu Lys Glu Lys Arg Glu Glu Val His Lys Tyr Val
        115                 120                 125

Gln Met Met Gly Gly Arg Val Tyr Arg Asp Leu Asn Val Ser Val Thr
    130                 135                 140

His Leu Ile Ala Gly Glu Val Gly Ser Lys Lys Tyr Leu Val Ala Ala
145                 150                 155                 160

Asn Leu Lys Lys Pro Ile Leu Leu Pro Ser Trp Ile Lys Thr Leu Trp
                165                 170                 175

Glu Lys Ser Gln Glu Lys Lys Ile Thr Arg Tyr Thr Asp Ile Asn Met
            180                 185                 190

Glu Asp Phe Lys Cys Pro Ile Phe Leu Gly Cys Ile Ile Cys Val Thr
        195                 200                 205

Gly Leu Cys Gly Leu Asp Arg Lys Glu Val Gln Gln Leu Thr Val Lys
    210                 215                 220

His Gly Gly Gln Tyr Met Gly Gln Leu Lys Met Asn Glu Cys Thr His
225                 230                 235                 240

Leu Ile Val Gln Glu Pro Lys Gly Gln Lys Tyr Glu Cys Ala Lys Arg
                245                 250                 255

Trp Asn Val His Cys Val Thr Thr Gln Trp Phe Phe Asp Ser Ile Glu
            260                 265                 270

Lys Gly Phe Cys Gln Asp Glu Ser Ile Tyr Lys Thr Glu Pro Arg Pro
        275                 280                 285

Glu Ala Lys Thr Met Pro Asn Ser Ser Thr Pro Thr Ser Gln Ile Asn
    290                 295                 300

Thr Ile Asp Ser Arg Thr Leu Ser Asp Val Ser Asn Ile Ser Asn Ile
305                 310                 315                 320

Asn Ala Ser Cys Val Ser Glu Ser Ile Cys Asn Ser Leu Asn Ser Lys
                325                 330                 335

Leu Glu Pro Thr Leu Glu Asn Leu Glu Asn Leu Asp Val Ser Ala Phe
            340                 345                 350

Gln Ala Pro Glu Asp Leu Leu Asp Gly Cys Arg Ile Tyr Leu Cys Gly
```

```
            355                 360                 365
Phe Ser Gly Arg Lys Leu Asp Lys Leu Arg Arg Leu Ile Asn Ser Gly
        370                 375                 380

Gly Gly Val Arg Phe Asn Gln Leu Asn Glu Asp Val Thr His Val Ile
385                 390                 395                 400

Val Gly Asp Tyr Asp Asp Glu Leu Lys Gln Phe Trp Asn Lys Ser Ala
                405                 410                 415

His Arg Pro His Val Val Gly Ala Lys Trp Leu Leu Glu Cys Phe Ser
            420                 425                 430

Lys Gly Tyr Met Leu Ser Glu Glu Pro Tyr Ile His Ala Asn Tyr Gln
        435                 440                 445

Pro Val Glu Ile Pro Val Ser His Lys Pro Glu Ser Lys Ala Ala Leu
    450                 455                 460

Leu Lys Lys Lys Asn Ser Ser Phe Ser Lys Lys Asp Phe Ala Pro Ser
465                 470                 475                 480

Glu Lys His Glu Gln Ala Asp Glu Asp Leu Leu Ser Gln Tyr Glu Asn
                485                 490                 495

Gly Ser Ser Thr Val Val Glu Ala Lys Thr Ser Glu Ala Arg Pro Phe
            500                 505                 510

Asn Asp Ser Thr His Ala Glu Pro Leu Asn Asp Ser Thr His Ile Ser
        515                 520                 525

Leu Gln Glu Glu Asn Gln Ser Ser Val Ser His Cys Val Pro Asp Val
    530                 535                 540

Ser Thr Ile Thr Glu Glu Gly Leu Phe Ser Gln Lys Ser Phe Leu Val
545                 550                 555                 560

Leu Gly Phe Ser Asn Glu Asn Glu Ser Asn Ile Ala Asn Ile Ile Lys
                565                 570                 575

Glu Asn Ala Gly Lys Ile Met Ser Leu Leu Ser Arg Thr Val Ala Asp
            580                 585                 590

Tyr Ala Val Val Pro Leu Leu Gly Cys Glu Val Glu Ala Thr Val Gly
        595                 600                 605

Glu Val Val Thr Asn Thr Trp Leu Val Thr Cys Ile Asp Tyr Gln Thr
    610                 615                 620

Leu Phe Asp Pro Lys Ser Asn Pro Leu Phe Thr Pro Val Pro Val Met
625                 630                 635                 640

Thr Gly Met Thr Pro Leu Glu Asp Cys Val Ile Ser Phe Ser Gln Cys
                645                 650                 655

Ala Gly Ala Glu Lys Glu Ser Leu Thr Phe Leu Ala Asn Leu Leu Gly
            660                 665                 670

Ala Ser Val Gln Glu Tyr Phe Val Arg Lys Ser Asn Ala Lys Lys Gly
        675                 680                 685

Met Phe Ala Ser Thr His Leu Ile Leu Lys Glu Arg Gly Gly Ser Lys
    690                 695                 700

Tyr Glu Ala Ala Lys Lys Trp Asn Leu Pro Ala Val Thr Ile Ala Trp
705                 710                 715                 720

Leu Leu Glu Thr Ala Arg Thr Gly Lys Arg Ala Asp Glu Ser His Phe
                725                 730                 735

Leu Ile Glu Asn Ser Thr Lys Glu Glu Arg Ser Leu Glu Thr Glu Ile
            740                 745                 750

Thr Asn Gly Ile Asn Leu Asn Ser Asp Thr Ala Glu His Pro Gly Thr
        755                 760                 765

Arg Leu Gln Thr His Arg Lys Thr Val Val Thr Pro Leu Asp Met Asn
    770                 775                 780
```

-continued

```
Arg Phe Gln Ser Lys Ala Phe Arg Ala Val Val Ser Gln His Ala Arg
785                 790                 795                 800

Gln Val Ala Ala Ser Pro Ala Val Gly Gln Pro Leu Gln Lys Glu Pro
                805                 810                 815

Ser Leu His Leu Asp Thr Pro Ser Lys Phe Leu Ser Asp Lys Leu
            820                 825                 830

Phe Lys Pro Ser Phe Asp Val Lys Asp Ala Leu Ala Ala Leu Glu Thr
            835                 840                 845

Pro Gly Arg Pro Ser Gln Gln Lys Arg Lys Pro Ser Thr Pro Leu Ser
850                 855                 860

Glu Val Ile Val Lys Asn Leu Gln Leu Ala Leu Ala Asn Ser Ser Arg
865                 870                 875                 880

Asn Ala Val Ala Leu Ser Ala Ser Pro Gln Leu Lys Glu Ala Gln Ser
                885                 890                 895

Glu Lys Glu Glu Ala Pro Lys Pro Leu His Lys Val Val Cys Val
                900                 905                 910

Ser Lys Lys Leu Ser Lys Lys Gln Ser Glu Leu Asn Gly Ile Ala Ala
            915                 920                 925

Ser Leu Gly Ala Asp Tyr Arg Trp Ser Phe Asp Glu Thr Val Thr His
        930                 935                 940

Phe Ile Tyr Gln Gly Arg Pro Asn Asp Thr Asn Arg Glu Tyr Lys Ser
945                 950                 955                 960

Val Lys Glu Arg Gly Val His Ile Val Ser Glu His Trp Leu Leu Asp
                965                 970                 975

Cys Ala Gln Glu Cys Lys His Leu Pro Glu Ser Leu Tyr Pro His Thr
            980                 985                 990

Tyr Asn Pro Lys Met Ser Leu Asp Ile Ser Ala Val Gln Asp Gly Arg
        995                 1000                1005

Leu Cys Asn Ser Arg Leu Leu Ser Ala Val Ser Thr Lys Asp Asp
        1010                1015                1020

Glu Pro Asp Pro Leu Ile Leu Glu Glu Asn Asp Val Asp Asn Met Ala
1025                1030                1035                1040

Thr Asn Asn Lys Glu Ser Ala Pro Ser Asn Gly Ser Gly Lys Asn Asp
                1045                1050                1055

Ser Lys Gly Val Leu Thr Gln Thr Leu Glu Met Arg Glu Asn Phe Gln
            1060                1065                1070

Lys Gln Leu Gln Glu Ile Met Ser Ala Thr Ser Ile Val Lys Pro Gln
            1075                1080                1085

Gly Gln Arg Thr Ser Leu Ser Arg Ser Gly Cys Asn Ser Ala Ser Ser
        1090                1095                1100

Thr Pro Asp Ser Thr Arg Ser Ala Arg Ser Gly Arg Ser Arg Val Leu
1105                1110                1115                1120

Glu Ala Leu Arg Gln Ser Arg Gln Thr Val Pro Asp Val Asn Thr Glu
                1125                1130                1135

Pro Ser Gln Asn Glu Gln Ile Ile Trp Asp Asp Pro Thr Ala Arg Glu
            1140                1145                1150

Glu Arg Ala Arg Leu Ala Ser Asn Leu Gln Trp Pro Ser Cys Pro Thr
            1155                1160                1165

Gln Tyr Ser Glu Leu Gln Val Asp Ile Gln Asn Leu Glu Asp Ser Pro
        1170                1175                1180

Phe Gln Lys Pro Leu His Asp Ser Glu Ile Ala Lys Gln Ala Val Cys
1185                1190                1195                1200

Asp Pro Gly Asn Ile Arg Val Thr Glu Ala Pro Lys His Pro Ile Ser
                1205                1210                1215
```

Glu Glu Leu Glu Thr Pro Ile Lys Asp Ser His Leu Ile Pro Thr Pro
            1220                1225                1230

Gln Ala Pro Ser Ile Ala Phe Pro Leu Ala Asn Pro Pro Val Ala Pro
        1235                1240                1245

His Pro Arg Glu Lys Ile Ile Thr Ile Glu Glu Thr His Glu Glu Leu
    1250                1255                1260

Lys Lys Gln Tyr Ile Phe Gln Leu Ser Ser Leu Asn Pro Gln Glu Arg
1265                1270                1275                1280

Ile Asp Tyr Cys His Leu Ile Glu Lys Leu Gly Gly Leu Val Ile Glu
                1285                1290                1295

Lys Gln Cys Phe Asp Pro Thr Cys Thr His Ile Val Val Gly His Pro
            1300                1305                1310

Leu Arg Asn Glu Lys Tyr Leu Ala Ser Val Ala Ala Gly Lys Trp Val
        1315                1320                1325

Leu His Arg Ser Tyr Leu Glu Ala Cys Arg Thr Ala Gly His Phe Val
    1330                1335                1340

Gln Glu Glu Asp Tyr Glu Trp Gly Ser Ser Ile Leu Asp Val Leu
1345                1350                1355                1360

Thr Gly Ile Asn Val Gln Gln Arg Arg Leu Ala Leu Ala Ala Met Arg
                1365                1370                1375

Trp Arg Lys Lys Ile Gln Gln Arg Gln Glu Ser Gly Ile Val Glu Gly
            1380                1385                1390

Ala Phe Ser Gly Trp Lys Val Ile Leu His Val Asp Gln Ser Arg Glu
        1395                1400                1405

Ala Gly Phe Lys Arg Leu Leu Gln Ser Gly Gly Ala Lys Val Leu Pro
    1410                1415                1420

Gly His Ser Val Pro Leu Phe Lys Glu Ala Thr His Leu Phe Ser Asp
1425                1430                1435                1440

Leu Asn Lys Leu Lys Pro Asp Asp Ser Gly Val Asn Ile Ala Glu Ala
                1445                1450                1455

Ala Ala Gln Asn Val Tyr Cys Leu Arg Thr Glu Tyr Ile Ala Asp Tyr
            1460                1465                1470

Leu Met Gln Glu Ser Pro Pro His Val Glu Asn Tyr Cys Leu Pro Glu
        1475                1480                1485

Ala Ile Ser Phe Ile Gln Asn Asn Lys Glu Leu Gly Thr Gly Leu Ser
    1490                1495                1500

Gln Lys Arg Lys Ala Pro Thr Glu Lys Asn Lys Ile Lys Arg Pro Arg
1505                1510                1515                1520

Val His

<210> SEQ ID NO 8
<211> LENGTH: 5148
<212> TYPE: DNA
<213> ORGANISM: Homo sapiens

<400> SEQUENCE: 8
cgaggctcca acgagttcag aaatgtccag aaatgacaaa gaaccgtttt ttgtgaagtt     60
tttaaagtct tcagacaatt ccaaatgttt ttttaaagct ctcgagtcca taaagaatt    120 ccaatcagaa gaatatcttc agattattac agaagaagag cattgaaga taaggagaa    180 tgatagatca ctttatatct gtgaccccttt tagtggcgtt gtctttgatc acctcaaaaa    240
gcttggctgc agaattgttg gtcctcaagt agtcatattt tgtatgcacc accagcgatg    300
tgtcccaaga gccgaacatc cagtttataa tatggttatg tctgatgtaa ccatatcttg    360

```
tacaagtctg gaaaaagaaa aaagggaaga agttcataaa tatgtacaaa tgatgggcgg      420
acgagtatac agagacctta atgtatcagt aactcacctt attgcaggag aagttggtag      480
caaaaaatat ttagttgctg caaacctgaa gaaacctatt ttgcttccct cttggataaa      540
aacactttgg gagaagtcac aagagaaaaa ataactaga tatactgata taaacatgga      600
agatttcaag tgtcctattt ttcttggttg cataatctgt gtgactggct tatgtggctt      660
agacaggaaa aagttcagc aactcacagt taagcatgga ggtcaataca tgggacaatt      720
gaaaatgaat aatgtacac acctcattgt gcaagaacca aaaggtcaga agtatgagtg      780
tgccaagaga tggaatgtac actgtgtgac cacacagtgg ttttttgaca gtattgagaa      840 aggttttgt caggatgaat ccatatacaa gacagaacct agaccagaag caaagactat      900
gcccaattct tcaactccta ccagccagat caacacaatt gatagtcgta ctctttcaga      960
tgtcagcaat atttccaaca taaatgcaag ttgcgtaagt gaatcaatat gtaattcact     1020
taacagcaaa ctggagccta cacttgaaaa tctagaaaat ctggatgtca gtgcatttca     1080
agcacctgaa gatttattag atggttgtcg gatatatctt tgcggtttta gtggcagaaa     1140
gctagataaa ctgagaagac ttattaacag tggaggtgga gttcgttta accagctaaa     1200 tgaagatgta actcatgtta ttgtgggaga ttatgatgat gaattgaagc agttttggaa     1260
taaatcagcc cacaggcctc atgtagtggg agcaaagtgg ttgctagagt gtttcagtaa     1320
aggttatatg ctttctgaag aaccatatat ccatgctaat taccagccag tggaaattcc     1380
agtttcacat aagcctgaaa gtaaagcagc tcttttaaaa aagaagaaca gcagcttctc     1440
taagaaagac tttgctccta gtgaaaagca tgagcaagct gatgaagatc tgctctctca     1500
atatgaaaat ggtagctcca cagtagttga ggctaagacg tctgaagcca ggcccttaa     1560 tgattctact catgctgagc ccttgaatga ttctactcac atttctttgc aagaagaaaa     1620
ccagtcttct gtcagtcatt gtgtccctga tgttttctaca attactgaag aaggcttatt     1680
tagccaaaag agtttccttg ttttgggttt tagtaatgaa aatgaatcta acatcgcaaa     1740
catcataaaa gaaatgctg ggaaaatcat gtcccttctg agcagaactg ttgcggatta     1800
tgctgtggtt cctctgctgg ggtgtgaagt ggaagccact gtgggagaag ttgttacaaa     1860
tacatggctg gttacttgca tagactatca gactttgttt gatccaaagt cgaatcctct     1920
cttcacacca gttccagtaa tgacaggaat gactccttta gaggattgtg ttatttcatt     1980
tagccagtgt gctggagcag aaaaagagtc tttaacattc ctagcaaacc tccttggagc     2040
aagtgttcaa gaatactttg ttcgcaaatc caatgcaaag aaaggcatgt ttgccagtac     2100 tcatctata ctgaaagaac gtggtggctc taaatatgaa gctgcaaaga agtggaattt     2160
acctgccgtt actatagctt ggctgttgga gactgctaga acgggaaaga gagcagacga     2220
aagccatttt ctgattgaaa attcaactaa agaagaacga agtttggaaa cagaaataac     2280
aaatggaatc aatctaaatt cagatactgc agagcatcct ggcacacgcc tgcaaactca     2340
cagaaaaacc gtcgttacac ctttagatat gaaccgcttt cagagtaaag ctttccgtgc     2400
tgtggtctca caacatgcca gacaggtcgc agcctccca gcagtaggac aaccacttca     2460
gaaggagccc tcgttacacc tggatacacc atcaaaattc ctgtccaagg acaaactctt     2520
caagccttcc tttgatgtga aggatgcact tgcagccttg gaaactccag gacgtcccag     2580
ccaacagaaa aggaaaccga gtacgccact ctcagaagtt attgtcaaaa acttgcaact     2640
tgctttggca aatagctctc gaatgctgt cgctcttct gccagccctc aactgaaaga     2700
ggcccagtca gagaaggaag aagccccaaa gccacttcac aaagtagtgg tatgtgttag     2760
```

```
taaaaaactc agtaagaagc agagtgaact aaatgggatc gcagcctctc taggagcaga    2820
ttacaggtgg agttttgatg aaacagtgac tcatttcatc tatcaagggc ggccaaatga    2880
cactaatcgg gagtataaat ctgtaaaaga aagaggagta cacattgttt ccgagcactg    2940
gcttttagat tgtgcccaag agtgtaaaca tcttcctgaa tctctttatc cacatactta    3000
taatcccaaa atgagcttgg atatcagcgc agtgcaagat ggccggctct gtaatagtcg    3060
actactctca gctgtgtctt caacaaagga tgatgagcca gatcctttga ttttagaaga    3120
aaatgatgta gacaatatgg ccaccaataa taaagagtca gcaccatcaa atggaagtgg    3180
aaagaatgac tctaaaggag ttctgacaca gaccttagag atgagagaga actttcagaa    3240
gcagttacag gagataatgt ctgcaacatc aatagtgaaa ccccaagggc agaggacttc    3300
cctttcaaga agtggttgta acagcgcatc ttcaaccct gacagcactc gctctgctcg     3360
cagtggacga agtagagtcc tagaggcact gaggcagtct cgtcagacag tacctgatgt    3420
caacacagag ccttcccaaa atgaacagat catttgggat gaccctacag caagggagga    3480
gagagcaagg cttgccagca atttgcagtg gcctagttgt cccacacaat actctgagct    3540
tcaggttgac attcaaaact tggaggattc ccttttcaa aagcctttac atgattcaga     3600
aattgctaaa caggctgtct gtgatcctgg aaacatacgt gtgactgaag ctcccaaaca    3660
cccaatctct gaagaactgg aaactcccat aaaagacagc cacctgatcc ctacgcctca    3720
agcccccagt attgcctttc cactcgccaa ccccctgtg gctccgcacc ctagagaaaa     3780
gattataacg atagaggaga ctcatgaaga attaaaaaaa cagtacatat ttcagttatc    3840
atctctgaat cctcaagaac gtattgacta ttgtcatctg attgagaaac taggtggatt    3900
ggtgatagaa aagcagtgct ttgatccac ctgtacacac attgttgtgg gacatccact      3960
tcgaaacgag aagtatttag cctcagtggc agctgggaag tgggtgcttc atcgctccta    4020
ccttgaagcc tgcaggactg ctggacactt cgtgcaggaa gaagactatg aatggggaag    4080
tagttccata cttgatgttc tgactggaat caatgtacag caacgaagac tagcacttgc    4140
agcaatgaga tggagaaaaa aaatccagca aagacaagaa tctggcattg ttgagggagc    4200
atttagtggg tggaaggtta ttttacatgt ggatcagtct cgagaagcag gcttcaaacg    4260
ccttcttcag tcaggaggag caaaggtgct acctggtcat tctgtacctt tatttaaaga    4320
ggccacacat cttttttctg acttgaataa actgaaacca gatgactcag gagttaatat    4380
agcagaagct gctgcccaga acgtgtactg cttgagaaca gaatacattg ctgattatct    4440
catgcaggaa tcacctcctc atgtagaaaa ttactgtcta ccagaagcta tttcatttat    4500
tcagaataat aaggaacttg ggactggatt atcacaaaag aggaaagctc ctacagaaaa    4560
aaataaaatc aaacgaccta gagtacacta atcgcatcta ccctttagtt accaaacatt    4620
aaatgttttt aaaaattgaa agcctgaatg tgactgtgat agatttgggt agtaatttaa    4680
agatgagtac ctgaagaatt ctgcttcaga gtataatgat gacccttctt gagttttgaa    4740
cacctgaaat tgtaatcact gaaatattaa ctgtttctta ataaaagtt acctgaaata     4800
acaacaaaat acaactcctc agctagcttg ctgttaaacc acattgaagt ctgttaaaag    4860
atatttattt ttcttgtaaa tatctgaagc tgtagcttag tggaaatttt agcaaggtaa    4920
tggattttgc tttaaaatgt ctgccttaca aattcataac aacaagattt gtcagtcagc    4980
atttattcat gttttccctg attttatct tctccaccatt ttacctctttt taacaggagc    5040
ctgagcacaa ggtttaatga ggaagctggg gctataaata tgtgtgtata tatgtatatg    5100
tatgtttgta caaatctcca tgatgtttgc caagtttgaa tgcgcaaa                 5148
```

-continued

```
<210> SEQ ID NO 9
<211> LENGTH: 1513
<212> TYPE: PRT
<213> ORGANISM: Xenopus laevis

<400> SEQUENCE: 9
```

Met Ala Ser Ser Glu Asn Glu Pro Phe Cys Val Lys Phe Ile Lys Ser
1               5                   10                  15

Pro Glu Asn Ser Glu Tyr Phe Phe Lys Ala Tyr Glu Ala Ile Lys Gln
            20                  25                  30

Ile Gln Ser Asp Glu Ser Leu Gln Leu Thr Glu Glu Arg Glu Ala Leu
        35                  40                  45

Leu Leu Lys Glu Lys Asp Lys Ser Leu Tyr Ile Cys Asp Pro Phe Ser
50                  55                  60

Gly Ala Ala Phe Ser His Leu Lys Lys Leu Gly Cys Arg Ile Val Gly
65                  70                  75                  80

Pro Gln Val Val Ile Phe Cys Met Glu Asn Gln Arg Arg Val Pro Arg
                85                  90                  95

Ala Glu Tyr Pro Val Tyr Asn Met Ala Met Ala Asp Val Thr Ile Ser
            100                 105                 110

Cys Thr Ser Leu Asp Lys Glu Thr Arg Glu Asp Val His His Tyr Val
        115                 120                 125

Gln Ile Met Gly Gly Cys Val Tyr Arg Asp Leu Asn Val Ser Val Thr
130                 135                 140

His Leu Ile Ala Gly Glu Val Gly Ser Lys Lys Tyr Leu Val Ala Ala
145                 150                 155                 160

Ser Leu Glu Lys Pro Ile Leu Leu Pro Ser Trp Val Lys Glu Leu Trp
                165                 170                 175

Glu Lys Ser Asn Gln Arg Ile Ile Arg Tyr Ser Asp Val Asn Met Thr
            180                 185                 190

Glu Tyr Leu Cys Pro Ile Phe Arg Gly Cys Thr Ile Cys Val Thr Gly
        195                 200                 205

Leu Ser Ser Leu Asp Arg Lys Glu Val Gln Arg Leu Thr Ala Leu His
210                 215                 220

Gly Gly Glu Tyr Thr Gly Gln Leu Lys Met Asn Glu Ser Thr His Leu
225                 230                 235                 240

Ile Val Gln Glu Ala Lys Gly Gln Lys Tyr Glu Cys Ala Arg Lys Trp
                245                 250                 255

Asn Val His Cys Ile Ser Val Gln Trp Phe Phe Asp Ser Ile Glu Lys
            260                 265                 270

Gly Phe Cys Gln Asp Glu Thr Met Tyr Lys Ile Glu Pro Ala Ser Thr
        275                 280                 285

Ile Lys Ser Val Pro Asp Thr Ser Thr Pro Thr Gly Asn Ser Lys
290                 295                 300

Pro Asn Ser Arg Ala Leu Tyr Asp Val Ser Gln Ile Ser Asn Ile Ser
305                 310                 315                 320

Thr Ser Cys Val Asn Glu Ser Ala Phe Asn Ser Ala Met Ala Ser Arg
                325                 330                 335

Leu Asp Pro Pro Ala Asp Thr Leu Glu Asn Leu Asp Ile Ser Ser Leu
            340                 345                 350

Gln Ala Pro Asp Asp Leu Leu Asp Gly Cys Arg Ile Tyr Leu Cys Gly
        355                 360                 365

Phe Gly Gly Arg Lys Leu Asp Lys Leu Arg Lys Leu Ile Asn Asn Gly
370                 375                 380

```
Gly Gly Val Arg Phe Asn Gln Leu Thr Gly Asp Val Thr His Ile Ile
385                 390                 395                 400

Val Gly Glu Thr Asp Glu Leu Lys Gln Phe Leu Asn Lys Thr Gln
            405                 410                 415

His Arg Pro Tyr Val Leu Thr Val Lys Trp Leu Leu Asp Ser Phe Ala
            420                 425                 430

Lys Gly His Leu Gln Pro Glu Ile Tyr Phe His Ser Ser Tyr Gln
            435                 440                 445

Gln Thr Glu Met Pro Ser Pro Phe Glu Pro Ala Ile Asn Leu Thr Ala
    450                 455                 460

Asn Lys Met Ser Ser Thr Arg Gly Pro Leu Asn His Thr Arg Asn His
465                 470                 475                 480

Gln Ala Asp Glu Asp Leu Leu Ser Gln Tyr Thr Glu Asn Asn Ser Thr
                485                 490                 495

Leu Ile Glu Asp Glu His Pro Lys Thr Ser Asn Thr Asn Ser Ile Ser
            500                 505                 510

Gln Met Ser Met His Glu Asp Met Thr Thr Cys Thr Ser Gln Ser Gly
            515                 520                 525

Leu Ala Asp Thr Ser Thr Ile Ile Glu Gly Gly Leu Phe Ser Arg Lys
530                 535                 540

Gln Phe Met Val Leu Gly Phe Leu Glu Glu Asp Glu Ala Cys Ile Ile
545                 550                 555                 560

Asp Ile Ile Lys Lys Ser Ala Gly Lys Val Leu Ser Ser Gln Lys Arg
                565                 570                 575

Ala Ile Ala Asp Tyr Ala Val Val Pro Leu Leu Gly Cys Glu Val Glu
            580                 585                 590

Ser Thr Val Gly Glu Val Val Thr Asn Ala Trp Leu Gly Met Cys Ile
            595                 600                 605

Glu Gln Glu Lys Leu Leu Asp Pro His Ser Asn Ala Leu Phe Thr Pro
610                 615                 620

Val Pro Phe Leu Glu Gly Ser Thr Pro Leu Arg Glu Cys Val Leu Ser
625                 630                 635                 640

Val Ser Gln Phe Met Gly Ala Glu Arg Asp Ser Leu Val Tyr Leu Ala
                645                 650                 655

Gly Leu Leu Gly Ala Lys Val Gln Glu Phe Phe Val Arg Lys Ala Asn
            660                 665                 670

Pro Lys Lys Gly Met Phe Ala Ser Thr His Leu Val Leu Lys Asp Ala
            675                 680                 685

Glu Gly Ser Lys Tyr Glu Ala Ala Lys Lys Trp Asn Leu Pro Ala Val
            690                 695                 700

Thr Met Asn Trp Leu Leu Gln Cys Ala Arg Thr Gly Arg Lys Ala Asp
705                 710                 715                 720

Glu Asp Ser Tyr Leu Val Asp Asn Val Pro Glu Glu Asp Lys Asp Glu
                725                 730                 735

Ser Phe Ile Ser Gln Thr Tyr Lys Pro Gln Ala Ile Arg Leu Ser Met
            740                 745                 750

His Ala Pro Cys His Leu Glu Asn His Pro Glu Ala Leu Thr Lys Ala
            755                 760                 765

Ala Val Thr Pro Leu Asp Met Asn Arg Phe Lys Ser Lys Ala Phe Gln
770                 775                 780

Ser Val Ile Ser Gln His Asn Lys Asn Pro Gln Thr Ser Gly Gly Glu
785                 790                 795                 800

Ser Lys Val Leu Gln Arg Glu Pro Ser Leu His Leu Asp Thr Pro Ser
                805                 810                 815
```

-continued

```
Lys Phe Leu Ser Lys Asp Lys Leu Phe Lys Pro Ser Phe Asp Val Lys
            820                 825                 830

Asp Ala Leu Ala Ala Leu Glu Thr Pro Gly Gly Pro Asn Gln Lys Asn
            835                 840                 845

Arg Thr Gln Ser Thr Pro Leu Ser Glu Val Ile Gly Arg Asn Leu Gln
        850                 855                 860

Leu Ala Ile Ala Asn Ser Thr Arg Gln Thr Ala Ala Val Thr Ala Ser
865                 870                 875                 880

Pro Gln Leu Lys Ala Ala Glu Lys Glu Phe Asp Asn Ser Lys Leu
            885                 890                 895

Leu Ile Asn Val Val Ile Cys Val Ser Lys Lys Leu Ile Lys Lys Gln
            900                 905                 910

Gly Glu Leu Asn Gly Ile Ala Ala Ser Leu Gly Ala Glu Tyr Arg Trp
        915                 920                 925

Cys Phe Asp Glu Ser Val Thr His Phe Ile Tyr His Gly Arg Gln Asn
        930                 935                 940

Asp Met Ser Arg Glu Tyr Lys Ser Val Lys Glu Arg Ser Gly Ile Tyr
945                 950                 955                 960

Ile Val Ser Glu His Trp Leu Phe Ala Cys Ser Glu Gln Gln Lys Arg
            965                 970                 975

Val Pro Glu Ala Leu Tyr Pro His Thr Tyr Asn Pro Lys Met Ser Leu
        980                 985                 990

Asp Ile Ser Ala Val Gln Asp Gly Ser Tyr Thr Ala Ser Lys Phe Ser
            995                 1000                1005

Ala Asp Thr Ser Leu Gln Gln Asp Glu Asn Ser Glu Leu Gln Leu Gln
    1010                1015                1020

Gln Asn Asn Lys Phe Gly Glu Thr Ser Asp Asp Gln Val Lys Lys Ala
1025                1030                1035                1040

Ala Gly Asp Gly Asn Pro Gln Asn Pro Ser Lys Asp Val Lys Gly Ala
                1045                1050                1055

Leu Thr Gln Thr Leu Glu Met Arg Glu Asn Phe Gln Arg Gln Leu Gln
            1060                1065                1070

Glu Phe Met Ser Ala Thr Ser Val Val Lys Pro Arg Gly Ser Val Gly
        1075                1080                1085

Arg Ala Gly Phe Asp Asn Ser Pro Cys Thr Pro Glu Gly Ala Arg Ser
    1090                1095                1100

Thr Arg Asn Gly Arg Ser Arg Val Leu Glu Ala Leu Arg Gln Ser Arg
1105                1110                1115                1120

Gln Ala Met Thr Asp Leu Asn Thr Glu Pro Ser Gln Asn Glu Gln Ile
                1125                1130                1135

Ile Trp Asp Asp Pro Thr Ala Arg Glu Glu Arg Ala Lys Leu Val Ser
            1140                1145                1150

Asn Leu Gln Trp Pro Asp Ser Pro Ser Gln Tyr Ser Glu Gln Leu Gln
        1155                1160                1165

His Asn Met Asn Asp Ala Gly Gly Asn Tyr Thr Pro Ala Lys Glu Ser
    1170                1175                1180

Leu Thr Asp Ser Glu Ile Ala Glu Leu Glu Ala Cys Glu Phe Glu Pro
1185                1190                1195                1200

Lys Ser Ala Met Arg Thr Pro Val Ile Glu Asn Asn Leu Gln Ser Pro
                1205                1210                1215

Thr Lys Pro Asp His Leu Thr Pro Thr Pro Gln Ala Pro Ser Ile Ala
            1220                1225                1230

Phe Pro Leu Ala Asn Pro Pro Val Ala Pro Gln Pro Arg Glu Lys Pro
```

```
                1235            1240            1245
Val Gln Pro Phe Ser Lys Glu Glu Thr Leu Lys Glu Arg Arg Phe Gln
    1250            1255            1260
Leu Ser Ser Leu Asp Pro Gln Glu Arg Ile Asp Tyr Ser Gln Leu Ile
1265            1270            1275            1280
Glu Glu Leu Gly Gly Val Ile Glu Lys Gln Cys Phe Asp Pro Ser
            1285            1290            1295
Cys Thr His Ile Val Val Gly His Pro Leu Arg Asn Glu Lys Tyr Leu
        1300            1305            1310
Ala Ser Met Ala Ala Gly Lys Trp Val Leu His Arg Ser Tyr Leu Glu
        1315            1320            1325
Ala Cys Arg Ala Ala Lys Arg Phe Ile Gln Glu Asp Tyr Glu Trp
        1330            1335            1340
Gly Ser Ile Ser Ile Leu Ser Ala Val Thr Asn Ile Asn Pro Gln Gln
1345            1350            1355            1360
Arg Met Leu Ala Glu Ala Ala Met Arg Trp Arg Lys Lys Leu Gln Gly
            1365            1370            1375
Ile Lys Gln Asn Met Gly Ile Ala Glu Gly Ala Phe Ser Gly Trp Lys
        1380            1385            1390
Val Ile Leu Asn Val Asp Gln Thr Lys Glu Pro Gly Phe Lys Arg Leu
        1395            1400            1405
Leu Gln Ser Gly Gly Ala Lys Val Phe Ala Gly His Ser Ser Pro Leu
    1410            1415            1420
Phe Lys Glu Ala Ser His Leu Phe Ala Asp Phe Ser Lys Leu Lys Pro
1425            1430            1435            1440
Asp Glu Pro Arg Val Asn Val Ala Glu Ala Ala Gln Gly Val Asn
            1445            1450            1455
Cys Leu Lys Pro Glu Tyr Ile Ala Asp Tyr Leu Met Lys Glu Leu Pro
        1460            1465            1470
Pro Pro Met Asn Asn Tyr Cys Leu Pro Asp Ala Ile Pro Tyr Val Arg
        1475            1480            1485
Val Thr Gly Thr Gly Leu Ser Arg Lys Arg Lys Thr Ser Gly Asp Val
    1490            1495            1500
Ser Asp Val Lys Arg Ser Arg His Tyr
1505            1510

<210> SEQ ID NO 10
<211> LENGTH: 5078
<212> TYPE: DNA
<213> ORGANISM: Xenopus laevis

<400> SEQUENCE: 10
caccacgggt cgtcatttcc gtcagtggcc ggacactgta ggaagcaata ggagatttgg      60
cgcgaatgac aaattggtcc cccagaaacc ggctccagtt aaaatggctt cgagtgaaaa     120
cgagccattt tgtgtgaaat ttatcaagtc tcctgaaaat tctgaatact tcttcaaagc     180
ttatgaggca atcaagcaaa ttcagtctga tgaatctctt cagctaacag aagaaagaga     240
ggcacttctc ttaaaagaaa aagacaaatc tctctacatt tgtgatcctt tcagtggtgc     300
tgcatttagc catctgaaaa agcttggctg taggatagtt ggcccacaag ttgtcatctt     360
ttgcatggag aatcaaagac gcgttcctcg tgctgaatac cctgtctaca atatggcaat     420
ggctgatgtg acaatatctt gcaccagcct cgataaagaa actagggaag atgtgcatca     480
ttatgtacaa atcatgggag ctgtgtgtta cagggatctt aatgtttctg tcacacacct     540
aattgctggt gaagtgggca gtaaaaaata cctggtggct gcaagtctgg agaagcccat     600
```

```
tcttcttcct tcttgggtga agaattatg ggaaaaatca aatcagagga ttattcgata    660
cagtgatgta aacatgacag aatatttgtg ccccatattt cgtggttgta ctatatgtgt    720
aactggatta agcagtttag acagaaagga ggtgcaacgt cttacagctc tgcatggagg    780
agagtacaca gggcagctta agatgaatga atcaacacat cttattgtcc aagaggctaa    840
aggccagaaa tatgagtgtg ccagaaagtg aatgtacac tgtatctcgg ttcaatggtt    900
cttcgacagt attgaaaaag gattctgtca agatgaaaca atgtataaaa ttgagcctgc    960
ttctaccata aaatctgtgc cagatacatc cactcctaca ggtggcaata gcaaaccaaa   1020
tagtcgggcc ctttatgatg tcagccagat ttccaatata agtacaagct gtgttaacga   1080
atctgctttt aactccgcaa tggccagcag actggatcct ccagcagata cccttgaaaa   1140
cttggatatt agttcattac aagctccaga tgacctactc gatggctgcc ggatatatct   1200
gtgcgggttt gggggaagaa agttggacaa gctaagaaag ctaatcaaca atggagggg    1260 tgtgaggttt aatcagctta caggagatgt aacccacatt attgttggag aaactgatga   1320
agaactgaag cagttttaa acaaaacaca acacagacct tatgtgttaa ctgtaaaatg    1380
gctgctggac agctttgcaa aaggacatct gcaacctgag gaaatatatt ttcattcaag    1440
ctatcaacaa actgagatgc cttcaccatt tgagcctgcc attaatttaa ctgctaataa    1500
gatgagtagt acacgagggc tctgaacca tactcgcaac catcaggcag atgaggacct    1560
gctgtctcag tacacagaaa ataactccac gttaattgaa gatgagcatc ctaaaacctc    1620
taataccaac agcatttccc aaatgagcat gcatgaagac atgaccactt gtacgagcca    1680
aagtggtttg gccgatacat ccactataat tgaaggaggt ttattcagcc gaaaacaatt    1740
tatggtgctg gcttttttgg aagaagatga ggcatgcatt atagacataa taagaagag    1800 cgctggcaag gtgctttcat ctcagaaaag agccattgct gattatgctg tagtacccct    1860
actgggttgt gaagtggaat ctacagttgg agaggttgtg accaacgctt ggctgggcat    1920
gtgtatagaa caagagaagc tattagaccc acattcaaat gctctttta cacctgtgcc    1980 atttttggaa ggtagcacac cactgcggga gtgtgtgctt tctgtcagcc aatttatggg    2040
tgctgaaagg gattcattag tttacttggc cggtttgctt ggagcaaaag tacaagagtt    2100
ttttgtgcgg aaagccaatc caaaaaaggg catgtttgcc agtacacact tagtacttaa    2160
agatgctgaa gggtcaaaat acgaagcagc caaaaagtgg aatttgccag cagtgacaat    2220
gaactggcta ttgcagtgtg ccagaactgg cagaaaagca gatgaagatt cttaccttgt    2280
tgataatgtt cctgaagaag ataaagatga agtttcata agtcagacat acaaacccca    2340
agcaatcagg ctatcaatgc atgcaccatg ccatctagaa aatcacccgg aagccctgac    2400
gaaagctgca gttaccccac ttgacatgaa ccggtttaag agcaaagcat tcagtctgt    2460 tatttcacag cataacaaga atccacaaac atcggtggg gaaagcaaag ttcttcagag    2520
agaaccatct ttgcatcttg atacaccatc aaaatttctg tccaaggaca aacttttcaa    2580
accctccttt gatgttaagg atgctcttgc agctctggaa acacctggag gtcctaacca    2640
aaaaaacagg acacagagca ctcccttgtc tgaagttatt ggtaggaatc tgcagctggc    2700
tattgcgaac agcacgcgtc agactgctgc agttactgca agccctcagc taaaggcagc    2760
agaaaagaaa gagttttgaca actccaagct actgattaat gtcgttatat gcgtgagcaa    2820
gaagctaatt aaaaaacaag gtgaactgaa tggcattgca gcctcacttg gagcagaata    2880
cagatggtgc ttcgatgaaa gtgtgacgca ttttatctac cacggacgac aaaatgacat    2940
gagccgagaa tacaaatctg tgaaagaacg aagtggcatc tacatcgttt ctgaacactg    3000
```

```
gctattcgct tgttcagaac agcagaagag agtacccgag gctctctatc cccatacata    3060
taatcctaaa atgagcttgg atatcagtgc tgttcaagat ggatcctaca cagccagcaa    3120
attctccgca gacacctctc ttcagcagga tgagaatagt gaattacagc ttcagcagaa    3180
taataaattt ggggagactt ctgatgatca ggttaaaaaa gcagctggtg atggaaaccc    3240 tcaaaccct tcaaaagacg ttaaaggagc tctaactcag actttagaga tgagagaaaa     3300
ttttcagcgg cagctacagg agttcatgtc tgcaacttca gtggtaaagc ctagggctc     3360 tgtgggtaga gctggctttg ataattcccc ttgtacacct gaaggggcac gttctcacg     3420 taatggaaga agcagagttt ggaagcact aagacagtcc aggcaggcta tgacagacct     3480
caatacagag ccatcgcaga atgagcaaat catttgggat gatcccactg ccagagaaga    3540
aagagcaaag ctggtcagca atctacagtg gcccgacagt ccctcccagt actctgaaca    3600
gcttcagcat aatatgaatg atgctggagg aaattataca ccagcaaagg aatctttaac    3660
agattctgaa atagcagaat ggaagcctg tgaattcgag cctaaatcag ctatgagaac     3720
tcctgtgata gagaataatt tgcagtctcc aaccaaaccg gatcatctca cccctacccc    3780
acaagctccg agcattgctt ttccacttgc caaccctcca gtggcaccac aacctagaga    3840
aaagcctgtg caaccatttt caaaggagga aactttaaag gagcgtcgat tccagctatc    3900
ttcattagac cctcaagaac gaattgatta ctcacagctt attgaggaac taggggagt     3960 ggtgatagaa aagcaatgtt ttgatccaag ctgcacacac atcgttgtgg gtcatcctct    4020
tcgtaatgaa aaatatttgg cctcaatggc tgcaggaaaa tgggtactgc acaggtcata    4080
tctggaagcc tgcagagctg caaaacgatt catacaggag gaggactatg aatggggaag    4140
catatccata ctgagtgctg tgaccaacat aaatccacag caaaggatgc tggcagaggc    4200
tgcaatgaga tggaggaaga agctgcaagg aataaagcaa aatatgggta tcgccgaggg    4260
tgcattcagt ggctggaaag taattttaaa tgtcgaccaa acaaaggaac ctggtttcaa    4320
acgtctgctc cagtcaggag gtgcaaaggt atttgctggc cattcttctc ctctgtttaa    4380
agaagcaagc cacctctttg ctgacttcag caaactgaaa cccgatgagc cagagtaaa    4440 tgtggcagag gctgcagcac aaggagtaaa ctgcctgaaa ccagagtata ttgccgacta    4500
cctcatgaag gagctacctc cgcccatgaa caattactgc ctcccagatg caattccata    4560
tgtccgggtt acagggactg ggctttcgcg caaaaggaaa acctctggag acgtctctga    4620
tgttaagaga tcacggcatt actgagagag tgagattgaa gagctagaga aaaaggcagc    4680
agcttggtaa tgccaactat gtagcactac tctttgtgac aaaatgttat gtactctgtc    4740
atgtctgtta atttatatgg aaatcggttt tttcatgtca aatactatgt agatatgtac    4800
acaaataaca ttccctgtat tttatatact tctatgtgtc cgtgcccaa tatatgtgaa     4860 atacgtttca taccctccct gttcattggg tgcagttacc gcccagttat ttgtacactt    4920
gtataatagg caacctttt tactctact attgtcattc ccttattgct cctgtccaac      4980
taacagtgga taggcaatat tgaatgaaat gttatttct tttttctttt aatagtactg     5040
tttttgagta tatgttaaaa tataataaat ctaaacac                            5078
```

<210> SEQ ID NO 11
<211> LENGTH: 6
<212> TYPE: PRT
<213> ORGANISM: Artificial Sequence
<220> FEATURE:
<223> OTHER INFORMATION: nuclear localization sequence

<400> SEQUENCE: 11

```
Lys Lys Lys Arg Lys Val
1               5

<210> SEQ ID NO 12
<211> LENGTH: 204
<212> TYPE: PRT
<213> ORGANISM: Xenopus laevis

<400> SEQUENCE: 12

Asp Ile Ser Ala Val Gln Asp Gly Ser Tyr Thr Ala Ser Lys Phe Ser
1               5                   10                  15

Ala Asp Thr Ser Leu Gln Gln Asp Glu Asn Ser Glu Leu Gln Leu Gln
            20                  25                  30

Gln Asn Asn Lys Phe Gly Glu Thr Ser Asp Asp Gln Val Lys Lys Ala
        35                  40                  45

Ala Gly Asp Gly Asn Pro Gln Asn Pro Ser Lys Asp Val Lys Gly Ala
    50                  55                  60

Leu Thr Gln Thr Leu Glu Met Arg Glu Asn Phe Gln Arg Gln Leu Gln
65                  70                  75                  80

Glu Phe Met Ser Ala Thr Ser Val Val Lys Pro Arg Gly Ser Val Gly
                85                  90                  95

Arg Ala Gly Phe Asp Asn Ser Pro Cys Thr Pro Glu Gly Ala Arg Ser
            100                 105                 110

Thr Arg Asn Gly Arg Ser Arg Val Leu Glu Ala Leu Arg Gln Ser Arg
        115                 120                 125

Gln Ala Met Thr Asp Leu Asn Thr Glu Pro Ser Gln Asn Glu Gln Ile
    130                 135                 140

Ile Trp Asp Asp Pro Thr Ala Arg Glu Glu Arg Ala Lys Leu Val Ser
145                 150                 155                 160

Asn Leu Gln Trp Pro Asp Ser Pro Ser Gln Tyr Ser Glu Gln Leu Gln
                165                 170                 175

His Asn Met Asn Asp Ala Gly Gly Asn Tyr Thr Pro Ala Lys Glu Ser
            180                 185                 190

Leu Thr Asp Ser Glu Ile Ala Glu Leu Glu Ala Cys
        195                 200

<210> SEQ ID NO 13
<211> LENGTH: 201
<212> TYPE: PRT
<213> ORGANISM: Homo sapiens

<400> SEQUENCE: 13

Asp Ile Ser Ala Val Gln Asp Gly Arg Leu Cys Asn Ser Arg Leu Leu
1               5                   10                  15

Ser Ala Val Ser Ser Thr Lys Asp Asp Glu Pro Asp Pro Leu Ile Leu
            20                  25                  30

Glu Glu Asn Asp Val Asp Asn Met Ala Thr Asn Asn Lys Glu Ser Ala
        35                  40                  45

Pro Ser Asn Gly Ser Gly Lys Asn Asp Ser Lys Gly Val Leu Thr Gln
    50                  55                  60

Thr Leu Glu Met Arg Glu Asn Phe Gln Lys Gln Leu Gln Glu Ile Met
65                  70                  75                  80

Ser Ala Thr Ser Ile Val Lys Pro Gln Gly Gln Arg Thr Ser Leu Ser
                85                  90                  95

Arg Ser Gly Cys Asn Ser Ala Ser Ser Thr Pro Asp Ser Thr Arg Ser
            100                 105                 110
```

```
Ala Arg Ser Gly Arg Ser Arg Val Leu Glu Ala Leu Arg Gln Ser Arg
        115                 120                 125

Gln Thr Val Pro Asp Val Asn Thr Glu Pro Ser Gln Asn Glu Gln Ile
    130                 135                 140

Ile Trp Asp Asp Pro Thr Ala Arg Glu Glu Arg Ala Arg Leu Ala Ser
145                 150                 155                 160

Asn Leu Gln Trp Pro Ser Cys Pro Thr Gln Tyr Ser Glu Leu Gln Val
                165                 170                 175

Asp Ile Gln Asn Leu Glu Asp Ser Pro Phe Gln Lys Pro Leu His Asp
            180                 185                 190

Ser Glu Ile Ala Lys Gln Ala Val Cys
            195                 200

<210> SEQ ID NO 14
<211> LENGTH: 206
<212> TYPE: PRT
<213> ORGANISM: Gallus gallus

<400> SEQUENCE: 14

Asp Ile Ser Ala Val Gln Asp Phe Arg Pro Ser Ser Ser Ser Glu Leu
1               5                   10                  15

Pro Pro Thr Gly Lys Pro Ala Glu Glu Asn Glu Ile Ile Ala Val Asp
            20                  25                  30

Glu Asp Asp Ala Glu Asp Asp Leu Thr Thr Asp Gln Ile Lys Glu Thr
        35                  40                  45

Ala Gly Thr Gly Glu Glu His Asn Gly Ile Ser Glu Ser Lys Gly Val
    50                  55                  60

Leu Thr Gln Ala Leu Glu Met Arg Glu Asn Phe Gln Arg Gln Leu Gln
65                  70                  75                  80

Glu Ile Met Ser Ala Thr Ser Ile Val Lys Pro Gln Gly Gln Arg Gly
                85                  90                  95

Ser Leu Ser Arg Asn Ser Phe Asp Ser Ser Pro Ala Thr Pro Asp Ser
            100                 105                 110

Ala Arg Ser Val Arg Asn Gly Arg Ser Arg Ala Leu Glu Ala Leu Arg
        115                 120                 125

Gln Ser Arg Gln Ala Phe Thr Asp Ile Asn Thr Glu Pro Ser Gln Ser
    130                 135                 140

Glu Gln Ile Ile Trp Asp Asp Pro Thr Ala Arg Glu Glu Arg Ala Arg
145                 150                 155                 160

Leu Val Ser Asn Phe Gln Trp Pro Asn Ser Pro Ser Gln Tyr Thr Glu
                165                 170                 175

Gln Ala Gln Ser Asn Val Asn Arg Asn Thr Asp Glu Ser Thr Phe Lys
            180                 185                 190

Gly Ser Ile Ala Asp Ala Glu Ile Ala Gly Ile Val Val Pro
        195                 200                 205

<210> SEQ ID NO 15
<211> LENGTH: 209
<212> TYPE: PRT
<213> ORGANISM: Danio rerio

<400> SEQUENCE: 15

Thr Met Ser Gln Met Ala Asp Ser Thr Gln Arg Ser Pro Pro Ser Ala
1               5                   10                  15

Thr Pro Arg Thr Arg Leu Arg Ala Phe Ala Glu Asn Glu Glu Thr Arg
            20                  25                  30

Leu Gly Pro Asp Asp Asp Ile Thr Asp Val Ser Thr Pro Asn Gln Ser
```

```
                35                  40                  45
Thr Val Gly Asp Pro Glu Lys Tyr Gln Thr Ile Ser Thr Asp Lys Lys
    50                  55                  60

Asn Leu Thr Glu Thr Leu Glu Met Arg Glu Ser Leu Gln Arg Gln Leu
65                  70                  75                  80

Gln Glu Ile Met Ser Ala Thr Lys Leu Thr Asn Gly Arg Arg Gly Ser
                85                  90                  95

Trp Arg Leu Ala Lys Thr Gly Pro Gly Pro Gly Leu Asp Ser His Thr
            100                 105                 110

Pro Asp Ser Leu Gly Arg Met Ser Arg Arg Ser Arg Asn Leu Lys Ala
            115                 120                 125

Ile Arg Met Ser Arg Gln Val Cys Val Asp Leu Asn Thr Glu Pro Ser
        130                 135                 140

Gln Ser Glu Gln Ile Val Trp Asp Asp Pro Thr Ala Arg Glu Glu Arg
145                 150                 155                 160

Ala Lys Leu Ala Asp Asn Leu Gln Trp Pro Gly Ser Pro Ser Gln His
                165                 170                 175

Ser Glu Pro Leu Ala Leu Val Pro Pro Pro His Ser Asp His Thr Thr
            180                 185                 190

Asn Gly Arg Asp Ser Met Thr Asp Ser Glu Leu Val Glu Met Ala Ala
            195                 200                 205

Phe
```